(12) United States Patent
Riesenberg et al.

(10) Patent No.: US 12,173,309 B2
(45) Date of Patent: Dec. 24, 2024

(54) COMPOUNDS FOR INCREASING GENOME EDITING EFFICIENCY

(71) Applicant: Max-Planck-Gesellschaft zur Förderung der Wissenschaften e.V., Munich (DE)

(72) Inventors: Stephan Riesenberg, Jena (DE); Tomislav Maricic, Leipzig (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 206 days.

(21) Appl. No.: 16/603,377

(22) PCT Filed: Apr. 10, 2018

(86) PCT No.: PCT/EP2018/059173
§ 371 (c)(1),
(2) Date: Oct. 7, 2019

(87) PCT Pub. No.: WO2018/189186
PCT Pub. Date: Oct. 18, 2018

(65) Prior Publication Data
US 2020/0392540 A1 Dec. 17, 2020

(30) Foreign Application Priority Data

Apr. 10, 2017 (EP) ..................................... 17165784
Nov. 24, 2017 (EP) ..................................... 17203591

(51) Int. Cl.
*C12N 15/90* (2006.01)
*C12N 9/12* (2006.01)

(52) U.S. Cl.
CPC .......... *C12N 15/907* (2013.01); *C12N 9/1205* (2013.01); *C12N 2310/20* (2017.05); *C12N 2800/80* (2013.01)

(58) Field of Classification Search
CPC .............. A61K 31/165; A61K 2300/00; A61K 31/505; A61K 31/5377; A61K 31/194
See application file for complete search history.

(56) References Cited

U.S. PATENT DOCUMENTS

2014/0242702 A1* 8/2014 Chen ........................ A61P 43/00 435/468
2018/0298392 A1* 10/2018 Cotta-Ramusino ......................... C12N 15/102

FOREIGN PATENT DOCUMENTS

JP 2016509063 A 3/2016
WO 2013/188881 A1 12/2013

OTHER PUBLICATIONS

Jeyakumar et al., Phosphorylation of Thyroid Hormone Receptor-associated Nuclear Receptor Corepressor Holocomplex by the DNA-dependent Protein Kinase Enhances Its Histone Deacetylase Activity. The Journal of Biological Chemistry (2007), 282(13): 9312-9322 (Year: 2007).*
Chiang et al., CRISPR-Cas9D10A nickase-based genotypic and phenotypic screening to enhance genome editing. Scientific Reports (2016), 6:24356, pp. 1-17 (Year: 2016).*
Robert et al., Pharmacological inhibition of DNA-PK stimulates Cas9-mediated genome editing. Genome Medicine (2015) 7:93, pp. 1-11 (Year: 2015).*
Jimeno et al., Neddylation inhibits CtIP-mediated resection and regulates DNA double strand break repair pathway choice. Nucleic Acids Research (2015), 43(2): 987-999 (Year: 2015).*
I-Scel, https://www.neb.com/products/r0694-i-scei#Product%20Information [retrieved Jan. 20, 2023] (Year: 2023).*
Glanzer et al., A small molecule directly inhibits the p53 transactivation domain from binding to replication protein A. Nucleic Acids Research (2013). 41(3): 2047-2059 (Year: 2013).*
Bothmer et al., Characterization of the interplay between DNA repair and CRISPR/Cas9-induced DNA lesions at an endogenous locus. Nature Communications (2017), DOI: 10.1038/ncomms13905, published Jan. 9, 2017 (Year: 2017).*
Takayama et al, Highly efficient biallelic genome editing of human ES/IPS cells using a CRISPR/Cas9 or TALEN system. Nucleic Acids Research (2017), 45: 5198-5207, published Feb. 21, 2017 (Year: 2017).*
Frank et al., M3814: a novel investigational DNA-PK inhibitor. Proceedings of the 107th Annual Meeting of the American Association for Cancer Research; Apr. 16-20, 2016; New Orleans, LA. Philadelphia (PA): AACR; Cancer Res 2016;76(14 Suppl): Abstract nr 1658. (Year: 2016).*
Luther et al., Delivery approaches for CRISPR/Cas9 therapeutics in vivo: advances and challenges. Excerpt Opinion on Drug Delivery (2018), 15(9): 905-913 (Year: 2018).*
Shen et al., Serine/threonine protein phosphatase 6 modulates the radiation sensitivity of glioblastoma. Cell Death and Disease (2011), 2, e241 (Year: 2011).*
Vriend et al., Distinct genetic control of homologous recombination repair of Cas9-induced double-strand breaks, nicks and paired nicks. Nucleic Acid Research (2016), 44(11): 5204-5217 and Supplemental Material (Year: 2016).*
Ran et al., Double Nicking by RNA-Guided CRISPR Cas9 for Enhanced Genome Editing Specificity. Cell (2013), 1380-1389 (Year: 2013).*
Korn and Krausz, Cell-based high-content screening of small-molecule libraries. Current Opinion in Chemical Biology (2007), 11: 503-510 (Year: 2007).*
Iyama and Wilson, DNA repair mechanisms in dividing and non-dividing cells. DNA Repair (2013), 12: 620-636 (Year: 2013).*
Fortini and Dogliotti, Mechanisms of dealing with DNA damage in terminally differentiated cells. Mutation Research (2010), 685: 38-44 (Year: 2010).*

(Continued)

*Primary Examiner* — Celine X Qian
*Assistant Examiner* — Catherine Konopka
(74) *Attorney, Agent, or Firm* — Eversheds-Sutherland (US) LLP

(57) ABSTRACT

The present invention relates to compounds, compositions and kits suitable to precise genome editing efficiency in a eukaryotic target cell or target organism.

9 Claims, 26 Drawing Sheets

Figure 1:
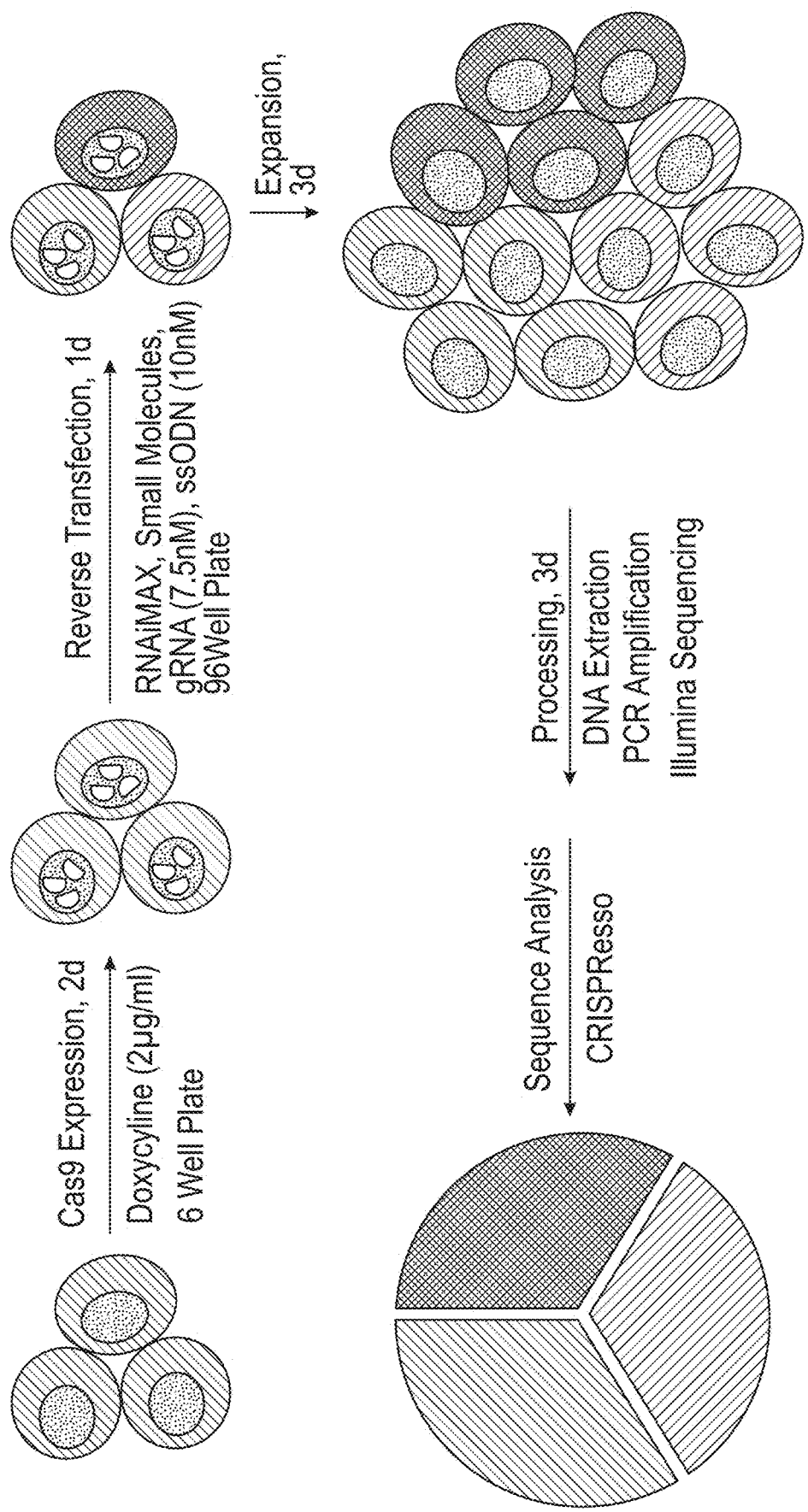

Specification includes a Sequence Listing.

(56) References Cited

OTHER PUBLICATIONS

Darzynkiewicz, Redundancy in response to DNA damage: The key to protection of genome integrity. Cell Cycle (2011), 10:3425 (Year: 2011).*

PCT International Search Report and Written Opinion for PCT Application No. PCT/EP2018/059173 mailed Sep. 12, 2018 (18 pages).

Maruyama et al., "Increasing the Efficiency of Precise Genome Editing with CRISPR-Cas9 by Inhibition of Nonhomologous End Joining," Nature Biotechnology, 2015, 33(5):538 (9 pages).

Mishra et al., "Chemical Inhibitor Targeting the Replication Protein A-DNA Interaction Increases the Efficacy of Pt-Based Chemotherapy in Lung and Ovarian Cancer," Biochemical Pharmacology, 2015, 93:25-33.

Robert et al., "Pharmacological Inhibition of DNA-PK Stimulates Cas9-Mediated Genome Editing," Genome Medicine, 2015, 7:93 (11 pages).

Shrivastav et al., "DNA-PKcs and ATM Co-Regulate DNA Double-Strand Break Repair," DNA Repair, 2009, 8:920-029.

Shrivastav et al., "Regulation of DNA Double-Strand Break Repair Pathway Choice," Cell Research, 2008, 18:134-147.

Suzuki et al., "In vivo Genome Editing via CRISPR/Cas9 Mediated Homology-Independent Targetd Integration," Nature, 2016, 540 (24 pages).

Takayama et al., "Highly Efficiency Biallelic Genome Editing of Human ES/IPS Cells Using a CRISPR/Cas9 or TALEN System," Nucleic Acids Research, 2017, 45(9):5198-5207.

Takayama et al., "Supplemental Information, Highly Efficiency Biallelic Genome Editing of Human ES/IPS Cells Using a CRISPR/Cas9 or TALEN System," Nucleic Acids Research, 2017 (36 pages).

Vartak et al., "Inhibition of Nonhomologous End Joining to Increase the Specificy of CRISPR/Cas9 Genome Editing," FEBS Journal, 2015, 282:4289-4294.

Zhou et al., "The NAE Inhibitor Pevonedistat Interacts with the HDAC Inhibitor Belinostat to Target AML Cells by Disrupting the DDR," Blood, 2016, 127(18):2219-2230.

Zhou et al., "The NAE Inhibitor Pevonedistat Interacts with the HDAC Inhibitor Belinostat to Target AML Cells by Disrupting the DDR," Blood, 2016, Supplemental, 21 pages.

Vriend et al., "Distinct genetic control of homologous recombination repair of Cas9-induced double-strand breaks, nicks and paired nicks" (2016), Nucleic Acids Research, vol. 44, No. 11, pp. 5204-5217.

Vriend et al., Supplementary Figures, 10 pages, From Reference 1, Nuc Acids Res 44(11), published 2016.

Jimeno et al., "Neddylation inhibits CtIP-mediated resection and regulates DNA double strand break repair pathway choice" (2015), Nucleic Acids Research, vol. 43, No. 2, pp. 987-999.

Jimeno et al., Supplementary Figures, 7 pages, From Reference 3, Nuc Acids Res 43(2), published 2015.

Glanzer et al., "A small molecule directly inhibits the p53 transactivation domain from binding to replication protein A" (2013), Nucleic Acids Research, vol. 41, No. 3, pp. 2047-2059.

Glanzer et al., Supplementary Figures, 4 pages. From Reference 5, Nuc Acids Res 41 (3), published 2013.

Office Action of May 17, 2022 in Japanese Application No. 2019-555112, 7 pages.

Partial European Search Report for EP Application No. 17165784.4 mailed Aug. 1, 2017 (22 pages).

Extended European Search Report for EP Application No. 17165784.4 mailed Nov. 7, 2017 (14 pages).

Pelascini et al., "Histone Deacetylase Inhibition Rescues Gene Knockout Levels Achieved with Integrase-Defective Lentiviral Vectors encoding Zinc-Finger Nucleases," Human Gene Therapy Methods, 2013, 24:399-411.

Office Action of Nov. 29, 2022 in Japanese Application No. 2019-555112, 9 pages.

Sascha Venturelli, et al. "Resveratrol as a Pan-HDAC Inhibitor Alters the Acetylation Status of Jistone Proteins in Human-Derived Hepatoblastoma Cells", PLOS One, Aug. 30, 2013, vol. 8, 12 pages, e73097.

Japanese Office Action in corresponding JP Application No. 052030/2023, dated May 14, 2024, 6 pages.

Neal et al., "Inhibition of homologous recombination by DNA-dependent protein kinase requires kinase activity, is titratable, and is modulated by autophosphorylation," Mol Cell Biol, 31(8), 2011, pp. 1719.

* cited by examiner

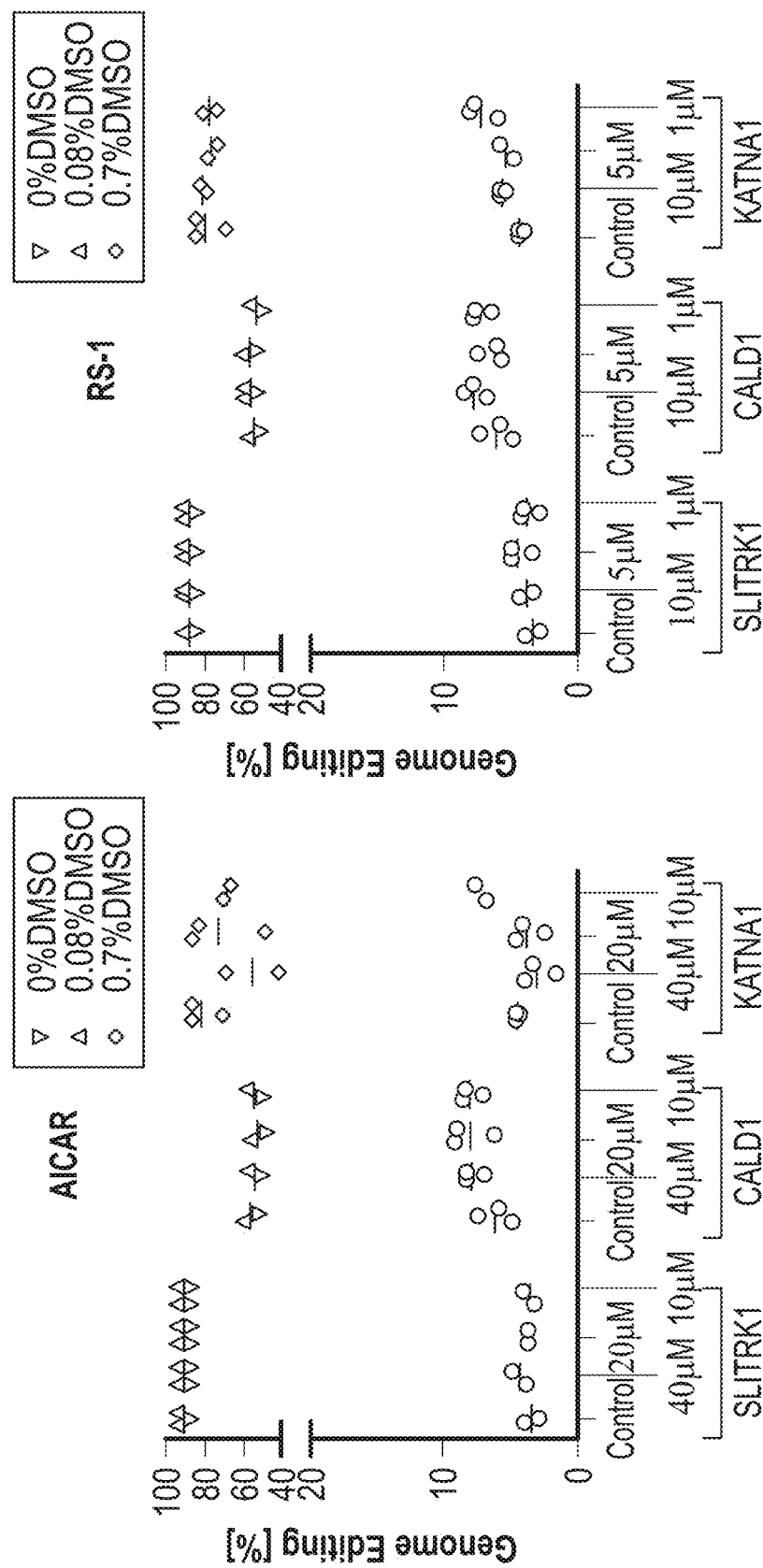

Long-term Genotoxicity
5× (1 Day Passaging with Mock or CRISPY mix, and RNAiMax; 3 Days Recovery)

| Sample | Metaphases | Band Number | Gray Shades | Healthy Karyotype (46,XX) |
|---|---|---|---|---|
| Mock (Bulk) | 20 | 400 | 3 | 20/20 |
| Crispy (Bulk) | 25 | 450 | 3 | 25/25 |
| Mock Clone 1 | 25 | 400 | 3 | 21/25 (4 Polyploid) |
| Mock Clone 2 | 25 | 400 | 3 | 25/25 |
| Mock Clone 3 | 25 | 400 | 3 | 25/25 |
| Mock Clone 4 | 25 | 400 | 3 | 25/25 |
| Mock Clone 5 | 25 | 400 | 3 | 25/25 |
| CRISPY Clone 1 | 25 | 400 | 3 | 25/25 |
| CRISPY Clone 2 | 25 | 400 | 3 | 25/25 |
| CRISPY Clone 3 | 25 | 400 | 3 | 25/25 |
| CRISPY Clone 4 | 25 | 400 | 3 | 22/25 (3 Polyploid) |
| CRISPY Clone 5 | 25 | 400 | 3 | 25/25 |

FIG. 7B

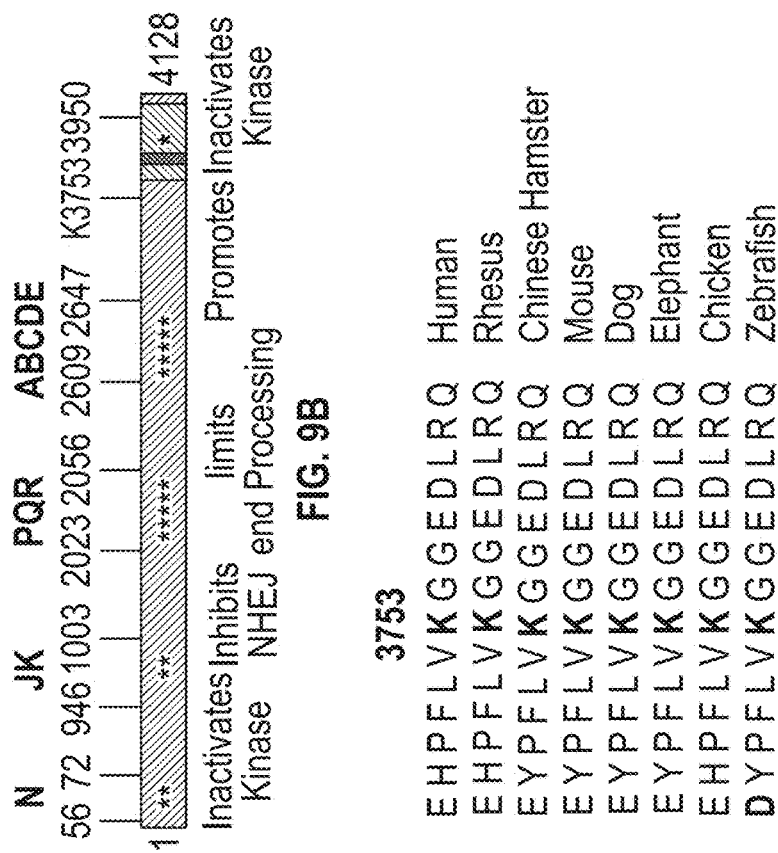
FIG. 9B
FIG. 9C
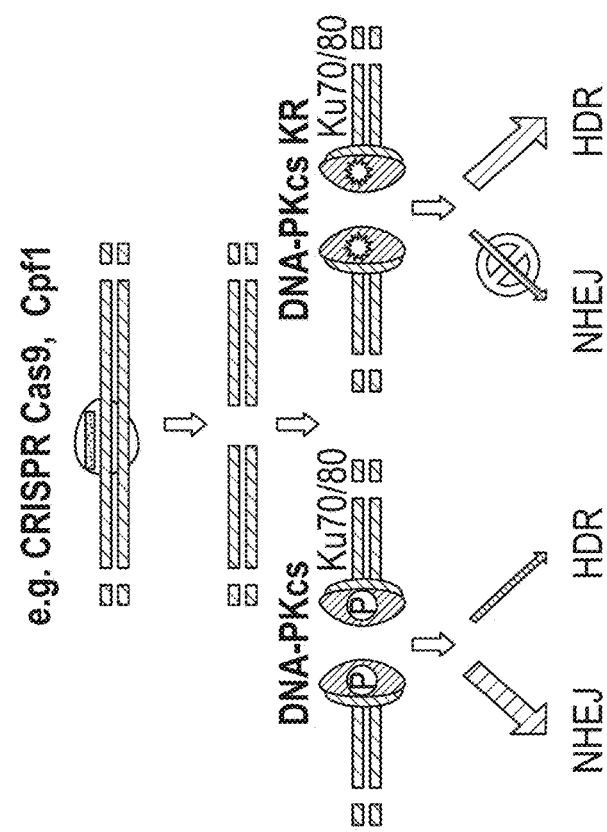
FIG. 9A

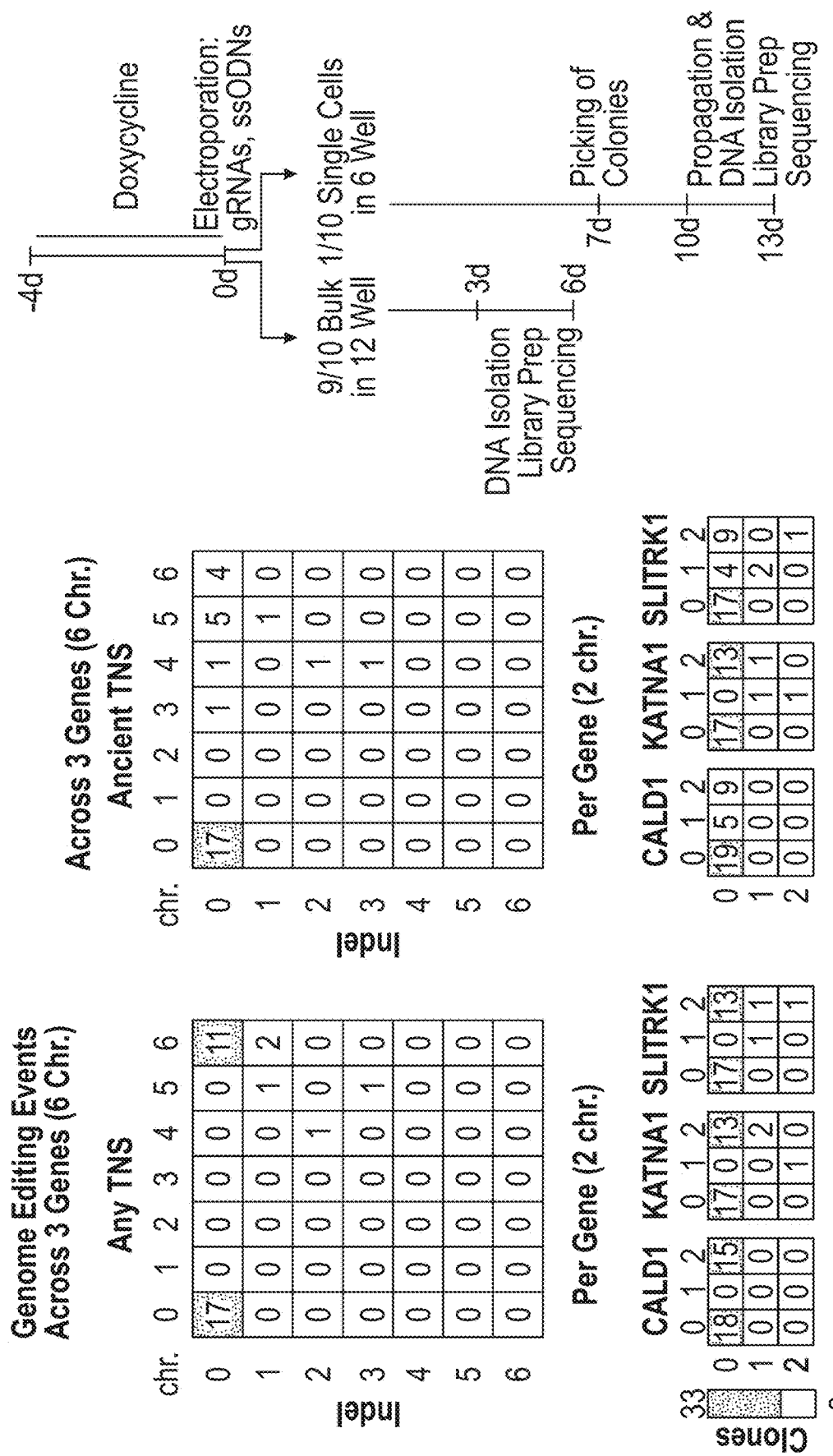

COMPOUNDS FOR INCREASING GENOME EDITING EFFICIENCY

CROSS REFERENCE TO RELATED APPLICATIONS

This application claims the priority benefit of PCT/EP2018/059173 filed on Apr. 10, 2018 which claims priority benefit of European Patent Application Nos. 17165784.4 and 17203591.7, filed Apr. 10, 2017 and Nov. 24, 2017, respectively. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Oct. 13, 2022, is named 18744-0125_SL.txt and is 17,440 bytes in size.

The present invention relates to compounds, compositions and kits suitable to increase precise genome editing efficiency in a eukaryotic target cell or target organism.

CRISPR is a bacterial nuclease immune system against viral DNA, which has been adopted to accurately cut chromosomal DNA sequences in eukaryotic cells. Such DNA breaks are repaired by two competing pathways: Non-homologous-End-Joining (NHEJ) or Homology directed Repair (HDR).

In NHEJ, the first proteins to bind to the DNA ends are Ku70/Ku80, followed by DNA protein kinase catalytic subunit (DNA-PKcs) (Shrivastav et al. 2008). The kinase phosphorylates itself and other downstream effectors at the repair site. Recruitment and phosphorylation of several proteins like Artemis result in end-processing ligation by ligase IV (LIG4), X-ray repair cross-complementing protein 4 (XRCC4) and Non-homologous end-joining factor 1 (XLF) (Dueva, Iliakis 2013).

If this canonical NHEJ pathway is repressed, an alternative NHEJ pathway (A-NHEJ) becomes active (Nussenzweig, Nussenzweig 2007). It requires Poly(ADP-ribose)-Polymerase 1 (PARP-1), Werner syndrome ATP-dependent (WRN) helicase and DNA ligase 3 (LIG3) or DNA ligase I (LIG1) amongst other proteins. Binding of the MRN-complex (Mre11, Rad50 and Nbs1) complex to the double strand break (DSB) initiates HDR (Shrivastav et al. 2008). Along with other proteins like DNA endonuclease RBBP8 (CtIP), Bloom helicase (BLM) and Exonuclease 1 (EXO1), terminal nucleotides in the 5' ends are removed, generating long 3' single-stranded DNA (ssDNA) overhangs on both sides of the break of the DNA (Dueva, Iliakis 2013). These tails are then coated and stabilized by the Replication protein A (RPA) complex, followed by breast cancer 2 (BRCA2) assisted generation of a Rad51 nucleoprotein filament (Shrivastav et al. 2008). Rad52 facilitates replacement of RPA bound to ssDNA with Rad51 and promotes ssDNA annealing (Grimme et al. 2010). Strand invasion with the donor DNA and subsequent DNA synthesis by a polymerase finally results in precisely repaired DNA. The protein kinase ataxia-telangiectasia mutated (ATM) plays a major role in HDR, as it phosphorylates at least 12 repair proteins (Shrivastav et al. 2008).

NHEJ of CRISPR Cas9-induced DSBs is error prone and frequently introduces insertions and deletions (indels) at the cut site. It is therefore useful for knocking out a targeted gene. In contrast, HDR allows precise repair of a DSB by using a homologous donor DNA sequence. If this donor sequence is provided in the experiment and carries mutations, these will be introduced into the genome.

A requirement for a DSB introduced by Cas9 is an NGG sequence (PAM site) in DNA. Targeting of Cas9 is determined by a bound guide RNA (gRNA) which is complementary to 20 nucleotides adjacent to the PAM site. However, the Cas9 nuclease may also cut the genome at sites that carry sequence similarity to those targeted by the gRNA (Fu et al. 2013). Those off-target double stranded cuts mean that unwanted mutations can appear elsewhere in the genome together with the desired mutation.

One strategy to reduce such off-target cuts is to use a mutated Cas9 that introduces single-stranded nicks instead of DSBs such as Cas9 D10A (Shen et al. 2014). Using two gRNAs to introduce two nicks on opposite DNA strands in close proximity to each other will result in a DSB at the desired locus while reducing the risk of two off-target nicks occurring elsewhere in the genome close enough to cause a DSB. Another strategy is to use Cpf1 (Zetsche et al. 2015). This nuclease introduces a staggered cut near a T-rich PAM site and has been shown to produce less off-target effects (Kim et al. 2016)(Kleinstiver et al. 2016).

In current approaches, precise genome editing (PGE) efficiencies, especially for targeted nucleotide substitutions in stem cells, are usually low, ranging from 0.5-15% (Yu et al. 2015)(Gonzalez et al. 2014). Several researchers addressed the low rate of precise genome editing by trying to promote HDR or decrease NHEJ.

Cell cycle synchronization to G2/M phase was shown to increase PGE with single stranded oligodeoxynucleotide (ssODN) donors in HEK293T cells (from 26% to 38%), human primary neonatal fibroblasts (from undetectable to 0.6%) and human embryonic stem cells (hESCs) (from undetectable to 1.6%) (Lin et al. 2014) and with double stranded oligodeoxynucleotide (dsODN) donors in hESCs (from 7 to 41% after sorting)(Yang et al. 2016), since homologous recombination is restricted to this phase and its proteins are upregulated.

Also, improved efficiency was achieved by suppressing key proteins like Ku70/80 and ligase IV with siRNA (from 5 to 25%) or co-expression of adenovirus type 5 proteins 4E1B55K and E4orf6 (from 5 to 36%) in HEK293/TLR cells using dsODN donors (Chu et al. 2015). E1B55K and E4orf6 proteins mediate the ubiquitination and proteosomal degradation of LIG4 among other targets.

A common strategy to increase genome editing has been the use of small molecules. The small molecule ligase IV inhibitor SCR7 has been claimed to block NHEJ and to increase the efficiency of PGE (from 5 to 22.7%) in mouse embryos (Maruyama et al. 2015). Other researchers described similar increase in HEK293/TLR cells, a marginal but significant increase in HEK293A, or found no significant effect in mouse embryos, rabbit embryos and human stem cells (Chu et al. 2015)(Pinder et al. 2015)(Song et al. 2016)(Yang et al. 2016)(Zhang et al. 2017). Recently, Greco et al. reanalysed the structure and inhibitory properties of SCR7 (Greco et al. 2016). They conclude that SCR7 and its derivates are neither selective nor potent inhibitors of human LIG4.

Pharmacological inhibition of DNA-PK, a key protein complex in the NHEJ-pathway, by the small molecules NU7441, KU-0060648 and NU7026 was shown to reduce the frequency of NHEJ and to increase PGE in HEK293/TLR cells (from 1.9 to 3.8%), HEK293 (3 to 7.6%) and human induced pluripotent stem cells (hiPSCs) (from 13 to 16%) with dsODN donors and in mouse embryonic fibroblasts (from 3 to 10%) with ssODN donors (Robert et al. 2015)(Suzuki et al. 2016)(Zhang et al. 2017).

Also, a single small molecule enhancing homologous recombination with CRISPR-Cas9 has been described. The RAD51 stimulatory compound RS-1 increased PGE in rabbit embryos (from 4.4 to 26.1%), HEK293A cells (from 3.5 to 21%) and U2OS cells (from 1.9 to 2.4%)(Song et al. 2016)(Pinder et al. 2015), but not in hiPSCs (Zhang et al., 2017), all with dsODN donors. No effect of RS-1 on PGE efficiency was found in porcine fetal fibroblasts using ssODN donors (Wang et al. 2016).

Furthermore, using a library screen of around 4000 small molecules, Yu et al. found the β3-adrenergic receptor agonist L755507 to increase PGE in hiPSCs (from 0.35 to 3.13%) using ssODN and using dsODN donors in mouse ESCs (from 17.7 to 33.3%), while the repair pathway target of that molecule is not known (Yu et al. 2015). Others did not find significant stimulation of PGE by L755507 in HEK293A cells or hiPSCs (Pinder et al. 2015)(Zhang et al. 2017). Pinder et al. compared SCR7, RS-1 and L755507 singly and together and found no additive effect when adding SCR7 and L755507 together with RS-1 compared to RS-1 alone.

From the overview of the current state-of-the art of small molecules that enhance CRIPR-Cas9 genome editing we learn that inhibitors of DNA-PK may increase PGE in CRISPR-Cas9 genome editing, but that the effects of SCR7, L755507 and RS-1 were not consistent between cell lines and loci. We also learn that previously tested combinations of small molecules did not show an additive effect.

The present inventors have found that certain compounds, particularly when applied as a combination of two or more different compounds increase precise genome editing efficiency. In particular, the inventors have found that compounds selected from inhibitors of histone deacetylase (HDAC) inhibitors of NEDD8 activating enzyme (NAE), inhibitors of DNA-dependent Protein Kinase (DNA-PK) in particular of its catalytic subunit (DNA-PKcs), and inhibitors of replication protein A (RPA) and combinations of compounds selected from these different classes of inhibitors, are capable of increasing genome editing efficiency. The compounds and combinations thereof are suitable both in non-medical applications, e.g. as research tool or in medical applications, e.g. for in vivo or ex vivo use.

Further, the present inventors have found that a DNA-PKcs which is catalytically inactive, but structurally intact, increases precise genome editing efficacy, independently from the presence of compounds as indicated above. This effect is found in a plurality of different systems for genome editing and thus is broadly applicable.

In a first aspect, the invention relates to a compound which is an inhibitor of histone deacetylase (HDAC), in the following designated as compound (I), for use in genome editing.

HDAC inhibitors are known as cytostatic agents for inhibiting tumor cell proliferation by inducing cell cycle arrest, differentiation and/or apoptosis. HDAC inhibitors usually act by binding to the zinc-containing catalytic domain of HDACs. They may be classified according to the chemical moiety that binds to the zinc ion. Examples of suitable classes of HDAC inhibitors are:

(1) Hydroxamate compounds,
(2) Cyclic tetrapeptides and depsipeptides which bind to the zinc ion via a thiol group,
(3) Benzamide compounds,
(4) Electrophilic ketones and
(5) Aliphatic acid compounds.

HDAC inhibitors are reviewed e.g. by Khan & La Thangue (Immunol. Cell Biol. 90 (2012), 85-94) and Falkenberg & Johnstone (Nature Rev. Drug Discovery 13 (2014) 673-691), herein incorporated by reference.

According to the present invention, HDAC inhibitors are preferably selected from synthetic non-nucleosidic compounds, e.g. small molecules having a molecular mass of 1500 Da or less or 1000 Da or less. Specific examples of HDAC inhibitors are selected from Trichostatin A, Vorinostat, Entinostat, Panobinostat, Mocetinostat, Belinostat, Romidepsin, MC1568, Tubastatin A HCl, Givinostat, LAQ824, CUDC-101, Quisinostat 2HC1, Pracinostat, PCI-34051, Droxinostat, PCI-24781, RGFP966, AR-42, Rocilinostat, Valproic acid, C1994, CUDC-907, Tubacin, M344, Resminostat, RG2833, Divalproex Sodium, Scriptaid, Phenylbutyrate, Tubastatin A, CAY10603, Nexturastat A, BG45, LMK-235, Santacruzamate A, BRD73954, HPOB, TMP269, Tasquinimod and 4SC-202 as well as salts or solvates thereof, in particular pharmaceutically acceptable salts or solvates thereof.

A preferred compound (I) is Trichostatin A including salts and solvates thereof.

In a second aspect, the present invention relates to a compound which is an inhibitor of NEDD8 activating enzyme (NAE), in the following designated as compound (II), for use in genome editing.

NAE inhibitors are known as anti-tumor agents as reviewed e.g. by Nawrocki et al. (Exp Opin Investing Drugs 21(2012), 1564-1573) or as antiviral agents as reviewed e.g. by Le-Trilling et al. (Sci. Rep. 6 (2016), doi: 19977), herein incorporated by reference.

According to the present invention, NAE inhibitors are preferably selected from synthetic non-nucleosidic compounds, e.g. small molecules having a molecular mass of 1500 Da or less or 1000 Da or less. A preferred NAE inhibitor is MLN4924 (Pevonedistat) or any salt or solvate thereof, in particular any pharmaceutically acceptable salt or solvate thereof.

In a third aspect, the present invention relates to a compound which is an inhibitor of DNA-dependent protein kinase (DNA-PK), in particular an inhibitor of its catalytic subunit (DNA-PKcs), in the following designated as compound (Ill) for use in genome editing. DNA-PK inhibitors are known as chemotherapeutic agents as reviewed e.g. by Davidson et al. (Front. Pharmacol. 4(2013), doi: 13 3389), herein incorporated by reference.

According to the present invention, DNA-PK inhibitors are preferably selected from synthetic non-nucleosidic compounds, e.g. small molecules having a molecular mass of 1500 Da or less or 1000 Da or less. Specific examples of DNA-PK inhibitors are NU7026, NU7441, PIK-75 and PI-103 as well as salts or solvates thereof, in particular pharmaceutically acceptable salts and solvates thereof.

In a preferred embodiment, the compound (III) is NU7026 including salts and solvates thereof.

In a fourth aspect, the invention relates to a compound which is an inhibitor of Replication Protein A (RPA), in the following designated as compound (IV) for genome editing.

RPA inhibitors are known as anti-tumor agents as reviewed e.g. by Neher et al. (Mel. Cancer Ther. 10(2011), 1756-1806), herein incorporated by reference.

According to the present invention, RPA inhibitors are preferably selected from synthetic non-nucleosidic compounds, e.g. small molecules having a molecular mass of 1500 Da or less or 1000 Da or less. Specific examples of RPA inhibitors are NSC15520, TDRL-505 and NSC111847, as well as salts or solvates thereof, in particular pharmaceutically acceptable salts and solvates thereof.

A preferred embodiment of compound (IV) is NSC15520 including salts and solvates thereof.

The present inventors have found that a compound (I), a compound (II), a compound (III), or a compound (IV) increase the frequency of precise genome editing in a eukaryotic cell such as an animal, e.g. mammalian including human cell.

In particular, the inventors found that compounds (I), (II), (Ill), and/or (IV) have an additive effect when administered together. In particular, when using a combination consisting of compounds Trichostatin A, MLN4924, NSC15520, and NU7026, an increase in precise genome editing of up to 6.7 fold or almost 50% edited chromosomes was achieved, the highest genome editing efficiency of human pluripotent stem cells described to date to the inventors' knowledge. Furthermore, when using the above combination of compounds in a pluripotent stem cell with a catalytically inactive DNA protein kinase catalytic subunit, in particular the mutant K3753R, an almost complete correct genome editing with up to 82% edited chromosomes or a 19.2 fold increase is achieved. Furthermore, they achieved multiplexed precise genome editing (MPGE) on both chromosomes of three genes without selection in less than two weeks, and show MPGE for the first time in a mammalian system. A third of analyzed clones has a targeted nucleotide substitution on both chromosomes of three genes.

An especially strong additive effect of administering a combination of two or more of compounds (I), (II), (Ill), and (IV), in particular a combination of at least one compound (III) and at least one compound (I) and optionally at least one compound (II) and/or at least one compound (IV), was found together with the use of a nuclease (e.g. Cpf1) or nickase enzyme system (e.g. Cas9D10A) capable of introducing a staggered cut in a DNA double strand, e.g. a chromosomal DNA, at a desired locus.

In further experiments, a strong effect of administering a combination of at least one compound (III) and at least one compound (I) and optionally at least one compound (IV) particularly in the absence of a compound (II) was found in hematopoietic cells, e.g. T cells such as $CD4^+$ T cells or hematopoietic precursor cells, e.g. $CD34^+$ cells together with the use of a nuclease (e.g. Cpf1) or nickase enzyme system (e.g. Cas9D10A) capable of introducing a staggered cut in a DNA double strand, e.g. a chromosomal DNA, at a desired locus.

In the human embryonic kidney cell line HEK293 and the leukemic cell line K562 a strong effect was found when administering at least one compound (III) optionally with at least one compound (I) and/or at least one compound (IV), particularly in the absence of a compound (II) together with the use of a nuclease (e.g. Cpf1) or nickase enzyme system (e.g. Cas9D10A) capable of introducing a staggered cut in a DNA double strand, e.g. a chromosomal DNA, at a desired locus.

Thus, an aspect of the invention relates to a combination, e.g. a composition or a kit comprising at least two of (a) a compound (I), (b) a compound (II), (c) a compound (III), and (d) a compound (IV). A preferred embodiment is a combination wherein the compound (I) is Trichostatin A, and/or the compound (II) is MLN4924, and/or the compound (III) is NU7026, and/or the compound (IV) is NSC15520. In particular, the combination of the invention is intended for use in genome editing including multiplexed genome editing on both chromosomes both in non-medical applications and in medical applications.

The term "combination" in the context of the present invention encompasses compositions comprising at least two compounds as indicated above together in admixture optionally together with a suitable carrier, e.g. a pharmaceutically acceptable carrier. The term "combination" also encompasses kits comprising at least two compounds as indicated above in separate forms, each optionally together with a suitable carrier, e.g. a pharmaceutically acceptable carrier.

Further, the present invention relates to a combination, e.g. a composition or kit comprising (i) at least one compound (I) and at least one compound (II), (ii) at least one compound (I) and at least one compound (III), (iii) at least one compound (I) and at least one compound (IV), (iv) at least one compound (II) and at least one compound (III), (v) at least one compound (II) and at least one compound (IV), or (vi) at least one compound (III) and at least one compound (IV). Preferred compounds (I), (II), (Ill), and/or (IV) are as indicated above.

Furthermore, the present invention relates to a combination, e.g. a composition or kit comprising (i) at least one compound (I), at least one compound (II), and at least one compound (III), (ii) at least one compound (I), at least one compound (II), and at least one compound (IV), or (iii) at least one compound (II), at least one compound (III), and at least one compound (IV). Preferred compounds (I), (II), (Ill), and/or (IV) are as indicated above.

Furthermore, the present invention relates to a combination, e.g. a composition or kit comprising at least one compound (I), at least one compound (II), at least one compound (III), and at least one compound (IV). Preferred compounds (I), (II), (Ill), and/or (IV) are as indicated above.

In an especially preferred embodiment, the present invention relates to a combination comprising at least one compound (III) and at least one compound (I) and optionally at least one compound (II) and/or at least one compound (IV). In some embodiments, compound (II) is absent.

In a further especially preferred embodiment, the present invention relates to a combination comprising at least one compound (III) and at least one of a compound (I) and a compound (IV). In some embodiments, compound (II) is absent.

The combination of the present invention as described may further include one or more additional compounds. In one embodiment, the combination may include a compound for synchronizing cells in the G2/M phase such as Nocodazole and ABT-751 (Yang et al., 2016), paclitaxel (Shu et al., Apoptosis 2 (1997), 463-470), or colchicine or vincristine (Blajeski et al., J. Clin. Invest. 110 (2002), 91-95), or salts or solvates thereof. In a further embodiment, the combination may include an Alt-NHEJ inhibitor such as NSC19630 or a salt or solvate thereof, in particular together with a catalytically inactive DNA protein kinase catalytic subunit.

The combination e.g. the composition or kit of the invention is suitable for use in genome editing in a eukaryotic target cell, particularly in a eukaryotic target cell as described in the following, including an animal target cell such as a mammalian target cell, e.g. a human target cell, but also target cell from non-human animals such as mice or zebrafish including a stem cell, e.g. human stem cell, for example an embryonic stem cell or a pluripotent stem cell. In some embodiments, the target cell is a stem cell of a eukaryotic target organism, including an induced or embryonic pluripotent stem cell such as a human induced or embryonic pluripotent stem cell but also an induced or embryonic pluripotent stem cell from non-human animals. In other embodiments, the target cell is a hematopoietic cell or a hematopoietic progenitor cell. In still other embodiments, the target cell is an immortalized cell such as a cancer cell.

The combination e.g. the composition or kit of the invention is particularly suitable in a genome editing procedure which comprises introducing a staggered cut, particularly a staggered cut with 5' overhangs, into the genome of the target cell. In order to achieve this result, the target cell may comprise a mutated nickase version of CRISPR/Cas9 such as CRISPR/Cas9 D10A or CRISPR/Cas9 H840A enzymes which are mutated nickase versions of CRISPR/Cas9 or a CRISPR/Cpf1 enzyme. Alternatively, other genome editing enzymes, e.g. CRISPRs, transcription activator-like effector-based nucleases (TALENs), zinc finger nuclease proteins, Argonaute of the bacterium Thermus thermophiles (TtAgo), recombinases, or meganucleases or other enzymes may be present, particularly enzymes which provide staggered cuts in a double stranded target DNA. The present invention is also suitable together with split-fusion versions of the above enzymes, e.g. split-fusion versions of Cas9 or Cas9 D10A (Zetsche et al., 2015). The enzyme(s) may be introduced into the target cell as such, e.g. as protein or ribonucleoprotein or as nucleic acid molecule encoding the respective enzyme(s). The nucleic acid molecule may be introduced as an expression vector such as a plasmid in operative linkage with appropriate expression control elements for transient or stable expression in the target cell. Suitable transfection techniques for introducing proteins or nucleic acids into the eukaryotic target cells are well known in the art and include lipofection, electroporation, e.g. nucleofection, Ca-phosphate or virus-based methods.

In a particular embodiment, the present invention relates to the use of a combination comprising at least one compound (III) and at least one compound (I) and optionally at least one compound (II) and/or at least one compound (IV) for the genome editing in a eukaryotic target cell which is a stem cell including an induced or embryonic pluripotent stem cell such as a human induced or embryonic stem cell, wherein the genome editing procedure which comprises introducing a staggered cut, particularly a staggered cut with 5' overhangs, into the genome of the target cell. A staggered cut may be introduced into the genome of the target cell by enzymes as indicated supra.

In a further particular embodiment, the present invention relates to the use of a combination comprising of at least one compound (III) and at least one compound (I) and optionally at least one compound (IV) particularly in the absence of a compound (II) for genome editing in a eukaryotic target cell which is hematopoietic cell such as a T cell, e.g. a CD4$^+$ T cell or a hematopoietic progenitor cell such as a CD34$^+$ cell, wherein the genome editing procedure which comprises introducing a staggered cut, particularly a staggered cut with 5' overhangs, into the genome of the target cell. A staggered cut may be introduced into the genome of the target cell by enzymes as indicated supra.

In a further particular embodiment, the present invention relates to the use of a combination comprising at least one compound (III) optionally with at least one of a compound (I) and/or a compound (IV) particularly in the absence of a compound (II) for the genome editing in a eukaryotic target cell which is a mammalian immortalized cell, e.g. HEK293 or K562 wherein the genome editing procedure which comprises introducing a staggered cut, particularly a staggered cut with 5' overhangs, into the genome of the target cell. A staggered cut may be introduced into the genome of the target cell by enzymes as indicated supra.

The combination, e.g. composition or kit of the present invention may further comprise (i) a DNA protein kinase catalytic subunit (DNA-PKcs) which is catalytically inactive, but structurally intact, (ii) a nucleic acid molecule encoding the DNA protein kinase catalytic subunit of (i) and/or (iii) a eukaryotic cell comprising or capable of expressing the DNA protein kinase catalytic subunit of (i) including a split-fusion version thereof. Preferably, the catalytically inactive, but structurally intact mutant has an amino acid sequence identity to the corresponding wild-type sequence, e.g. the human sequence NP_008835.5 of at least 80%, at least 85%, at least 90%, at least 95%, or at least 99% and comprises at least one mutation compared to the wild-type sequence which results in reduced kinase activity. Suitable structurally intact and catalytically inactive mutants and tests for detecting such mutants are e.g. described by Neal et al., 2001, herein incorporated by reference.

The catalytically inactive, but structurally intact DNA-PKcs subunit may be introduced into the target cell as protein or as nucleic acid encoding the respective subunit for transient or stable expression in the target cell. This approach may be used in combination with a Knock-down of the endogenous DNA-PKcs gene in the target cell, e.g. by targeted homologous recombination or by use of RNA interference, e.g. siRNAs. Further, this approach may be used in cells without endogenous DNA-PKcs, e.g. by using a DNA-PKcs mutant from a different species, e.g. evolutionary closely related species.

In particular, the DNA-PKcs mutant comprises at least one mutation in the catalytic loop (amino acids 3919-3927) including the catalytic triade (N3927, D3922, H3924) or in the P-loop (amino acids 3729-3735) or in the adjacent region (amino acids 3736-3760) including amino acids F3946, T3950, and particularly K3753 based on the NCBI reference sequence NP_008835.5. It may also comprise a mutation leading to a truncation (e.g. Y4046*) based on the NCBI reference sequence NP_008835.5, which reduces or inactivates the kinase activity. The position of the indicated amino acids may vary in DNA-PKcs or its orthologues in other species than humans.

Even more particularly, the DNA-PKcs mutant comprises at least one mutation at position K3753, e.g. the mutation K3753R, and/or K3753H, at position D3922, e.g. the mutation D3922A, at position T3950, e.g. the mutation T3950D, and/or at position F3946, e.g. F3946D, based on the NCBI reference sequence NP_008835.5. The position of the indicated amino acids may vary in DNA-PKcs or its orthologues in other species than humans.

Further, the DNA-PKcs can comprise at least one mutation in the phosphorylation clusters, which are normally targets of its autophosphorylation function. These can include inactivating mutations, e.g. but not restricted to alanine, for the PQR cluster (S2023 and/or S2029 and/or S2041 and/or S2053 and/or S2056), and/or activating (phosphomimicking) mutations, e.g. but not restricted to aspartatic acid, for the ABCDE cluster (T2069 and/or S2612 and/or T2620 and/or S2624 and/or T2638 and/or T2647) and/or the N cluster (S56 and/or S72) and/or the JK cluster (T946 and/or S1003) based on the NCBI reference sequence NP_008835.5. The position of the indicated amino acids may vary in DNA-PKCs or its orthologues in other species than humans.

The combination, e.g. the composition or kit is suitable for use with all kinds of donor nucleic acid molecules including but not limited to single stranded molecules or double stranded DNA molecules whether amplified in vivo or in vitro or chemically synthesized. The length of the donor nucleic acid molecules is usually in the range of about 20 to 2000 nt or more, e.g. about 80 to 120 nt, 50 to 200 nt or 500 to 2000 nt. The donor nucleic acid molecules are designed to include at least one desired mutation in view of the wild type sequence which is to be introduced into the genome of the target cell by genome editing. The mutation may be a single nucleotide mutation or a mutation encompassing a plurality of nucleotides. In this context, the term mutation refers to a substitution, deletion, or insertion of single nucleotides or of a plurality of nucleotides.

The above aspects comprise a use in vivo, e.g. in isolated cells or cell clusters, but also in vitro, in cells of a target organism. The combinations can be applied in cell types and with genome editing procedures as indicated above, particularly including the use of DNA cleavage enzyme systems capable of introducing a staggered cut in a DNA double strand. This aspect also includes a use in medicine including human or veterinary medicine.

A further aspect of the present invention relates to the use of (i) a DNA protein kinase catalytic subunit which is catalytically inactive, but structurally intact, as described above, particularly the mutated subunit K3753R, (ii) a nucleic acid molecule encoding the DNA protein kinase catalytic subunit of (i) and/or (iii) a eukaryotic cell comprising or capable of expressing the DNA protein kinase catalytic subunit of (i) for genome editing in a eukaryotic target cell, particularly in a vertebrate target cell, e.g. a mammalian target cell including a rodent, a human or non-human target cell including a human stem cell.

This aspect comprises a use in vivo, e.g. in isolated cells or cell clusters, but also in vitro, in cells of a target organism. The DNA-PKcs mutants can be applied in all cell types and with all types of genome editing procedures, e.g. including the use of any DNA cleavage enzyme, e.g. enzyme systems capable of introducing a staggered cut in a DNA double strand as described above, but also other enzyme systems, e.g. enzyme systems capable of introducing a blunt ended cut. This aspect also includes a use in medicine including human or veterinary medicine.

Still a further aspect of the present invention is the use of the combination, e.g. the composition or kit comprising at least two different compounds (I), (II), (Ill), and (IV) in medicine including human or veterinary medicine. An effective dose of the compounds according to the invention, or their salts, solvates or prodrugs thereof is used, in addition to physiologically acceptable carriers, diluents and/or adjuvants for producing a pharmaceutical composition. The dose of the active compounds can vary depending on the route of administration, the age and weight of the patient, the nature and severity of the diseases to be treated, and similar factors. The daily dose can be given as a single dose, which is to be administered once, or be subdivided into two or more daily doses, and is as a rule 0.001-2000 mg. Particular preference is given to administering daily doses of 0.1-500 mg, e.g. 0.1-100 mg.

Suitable administration forms are oral, parenteral, intravenous, transdermal, topical, inhalative, intranasal and sublingual preparations. Particular preference is given to using oral, parenteral, e.g. intravenous or intramuscular, intranasal preparations, e.g. dry powder or sublingual, of the compounds according to the invention. The customary galenic preparation forms, such as tablets, sugar-coated tablets, capsules, dispersible powders, granulates, aqueous solutions, alcohol-containing aqueous solutions, aqueous or oily suspensions, syrups, juices or drops, can be used.

Solid medicinal forms can comprise inert components and carrier substances, such as calcium carbonate, calcium phosphate, sodium phosphate, lactose, starch, mannitol, alginates, gelatine, guar gum, magnesium stearate, aluminium stearate, methyl cellulose, talc, highly dispersed silicic acids, silicone oil, higher molecular weight fatty acids, (such as stearic acid), gelatine, agar agar or vegetable or animal fats and oils, or solid high molecular weight polymers (such as polyethylene glycol); preparations which are suitable for oral administration can comprise additional flavourings and/or sweetening agents, if desired.

Liquid medicinal forms can be sterilized and/or, where appropriate, comprise auxiliary substances, such as preservatives, stabilizers, wetting agents, penetrating agents, emulsifiers, spreading agents, solubilizers, salts, sugars or sugar alcohols for regulating the osmotic pressure or for buffering, and/or viscosity regulators.

Preparations for parenteral administration can be present in separate dose unit forms, such as ampoules or vials. Use is preferably made of solutions of the active compound, preferably aqueous solution and, in particular, isotonic solutions and also suspensions. These injection forms can be made available as ready-to-use preparations or only be prepared directly before use, by mixing the active compound, for example the lyophilisate, where appropriate containing other solid carrier substances, with the desired solvent or suspending agent.

Intranasal preparations can be present as aqueous or oily solutions or as aqueous or oily suspensions. They can also be present as lyophilisates which are prepared before use using the suitable solvent or suspending agent.

Inhalable preparations can present as powders, solutions or suspensions. Preferably, inhalable preparations are in the form of powders, e.g. as a mixture of the active ingredient with a suitable formulation aid such as lactose.

The preparations are produced, aliquoted and sealed under the customary antimicrobial and aseptic conditions.

The compounds of the invention may be administered alone or as a combination therapy with further active agents.

The medical use of the combination of the present invention particularly encompasses target gene therapy, e.g. the treatment of disorders associated with an undesired genotype of a patient in need of the treatment. For example, the disorder is a metabolic dysfunction or cancer. By means of the invention, cells from the patient may be subjected to a genome editing procedure in the presence of a combination as described above, thereby increasing the precise genome editing efficiency. This procedure may be carried out in vivo, i.e. by administering the combination to the patient or ex vivo with cells isolated from the patients, which are—after successful genome editing—reimplanted into the patient. The patient may be a vertebrate animal such as a mammal, preferably a human patient. Finally, the combination of the present invention is also suitable for genome editing in plant cells or plants.

Further, the invention shall be explained in more detail by the following Figures and Examples.

FIGURE LEGENDS

FIG. 1: Genome editing and analysis flowchart. iCRISPR 409-B2 iPSCs are treated with 2 μg/ml doxycycline at least for 2 days to induce Cas9 or Cas9D10A expression. Reverse transfection with RNAiMAX, gRNA (7.5 nM each), ssODN (10 nM) and the small molecules to be evaluated is carried out in a 96 well plate for 1 day. The amount of cells used gives ~80% confluency. Cells are then expanded for 3 days with regular media change. After harvest follows DNA extraction, PCR amplification of targeted loci, Illumina sequencing and CRISPResso (Pinello et al. 2016) sequence analysis for amount of indels and precise genome editing.

Figure 2:
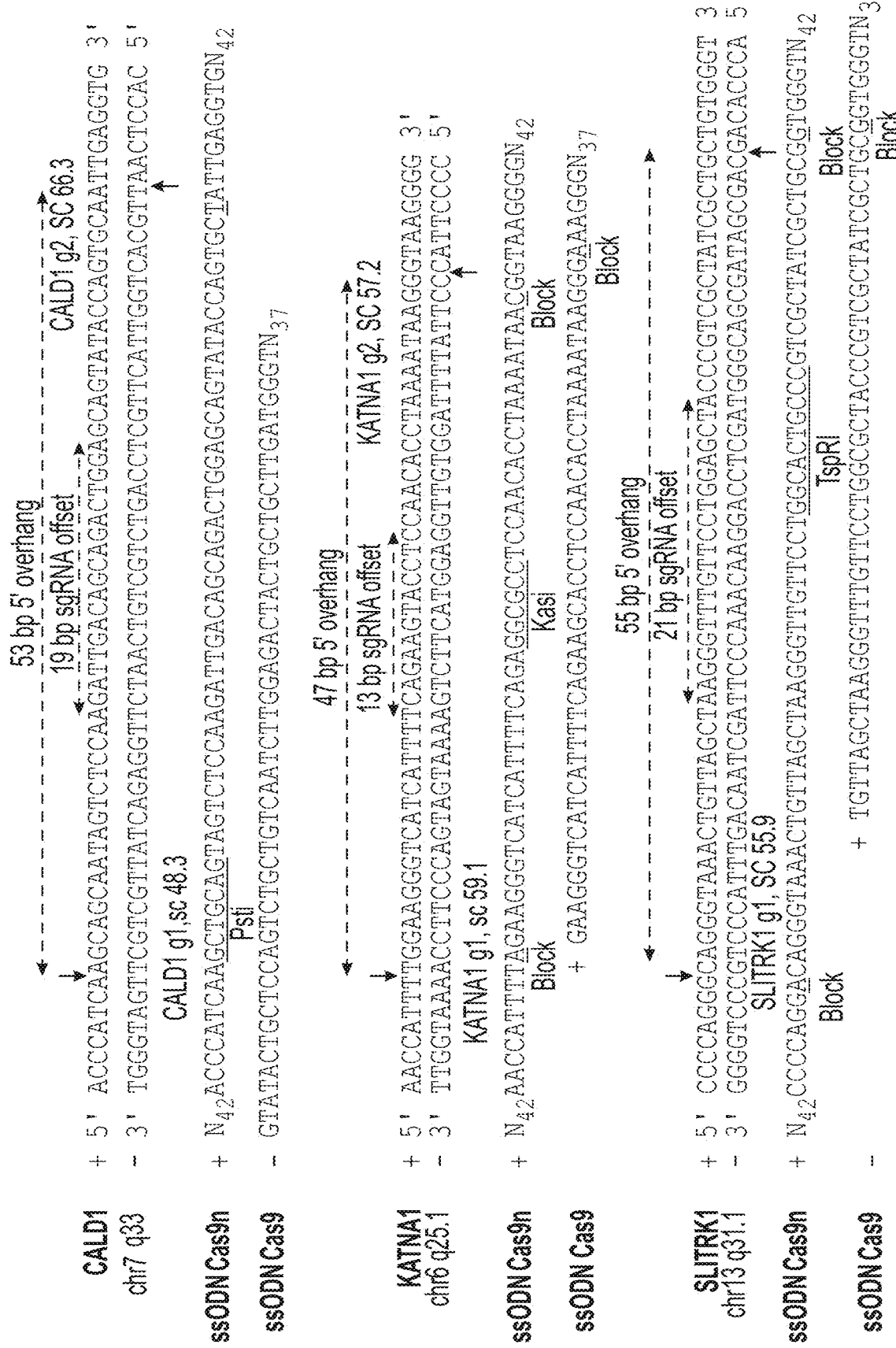

FIG. 2: Design of gRNAs and ssODN for precise genome editing (PGE) of human CALD1, KATNA1 and SLITRK1 to the ancient state of the last common ancestor of human and Neanderthal. Shown are the respective loci of CALD1, KATNA1 and SLITRK1 together with the gRNAs and their efficiency score (sc) (sgRNA scorer 1.0 Chari et al. 2015) used for DSB generation. The PAM site is grey, the target sequence is blue and the base to be changed is red. The point of nick by Cas9D10A (Cas9n) or DSB by Cas9 is indicated by an arrow. Whereas both guides are used for editing with Cas9n, CALD1 g1, KATNA1 g2 and SLITRK1 g2 are used for editing with Cas9. The respective ssODN for editing with both Cas9 variants are also shown. Desired mutation is marked green and additional mutations are orange. 'Block' indicates a Cas9-blocking mutation to prevent re-cutting oft the locus. All Cas9D10A donors have 50 nt homology arms after the nicks while all Cas9 donors are 90 nt in total with the desired mutation centered in the middle. The full sequences are shown in Table 2. FIG. 2 discloses SEQ ID NOS 50-61, respectively, in order of appearance.

FIGS. 3A-3D: First screen for solvent effect and influence of different small molecule concentrations on genome editing of CALD1, KATNA1 and SLITRK1 with iCRISPR Cas9D10A. Shown are precise genome editing (PGE) and indels with green circles (triangles) or blue diamonds, respectively. Each symbol represents a technical replicate. The respective means are shown as a black line. Each skull indicates cell death of up to 20% determined by phase contrast light microscopy. All cells died with 1 µM and 0.1 µM Trichostatin A. Concentrations chosen for further experiments are marked with turquoise.

Figure 4A:
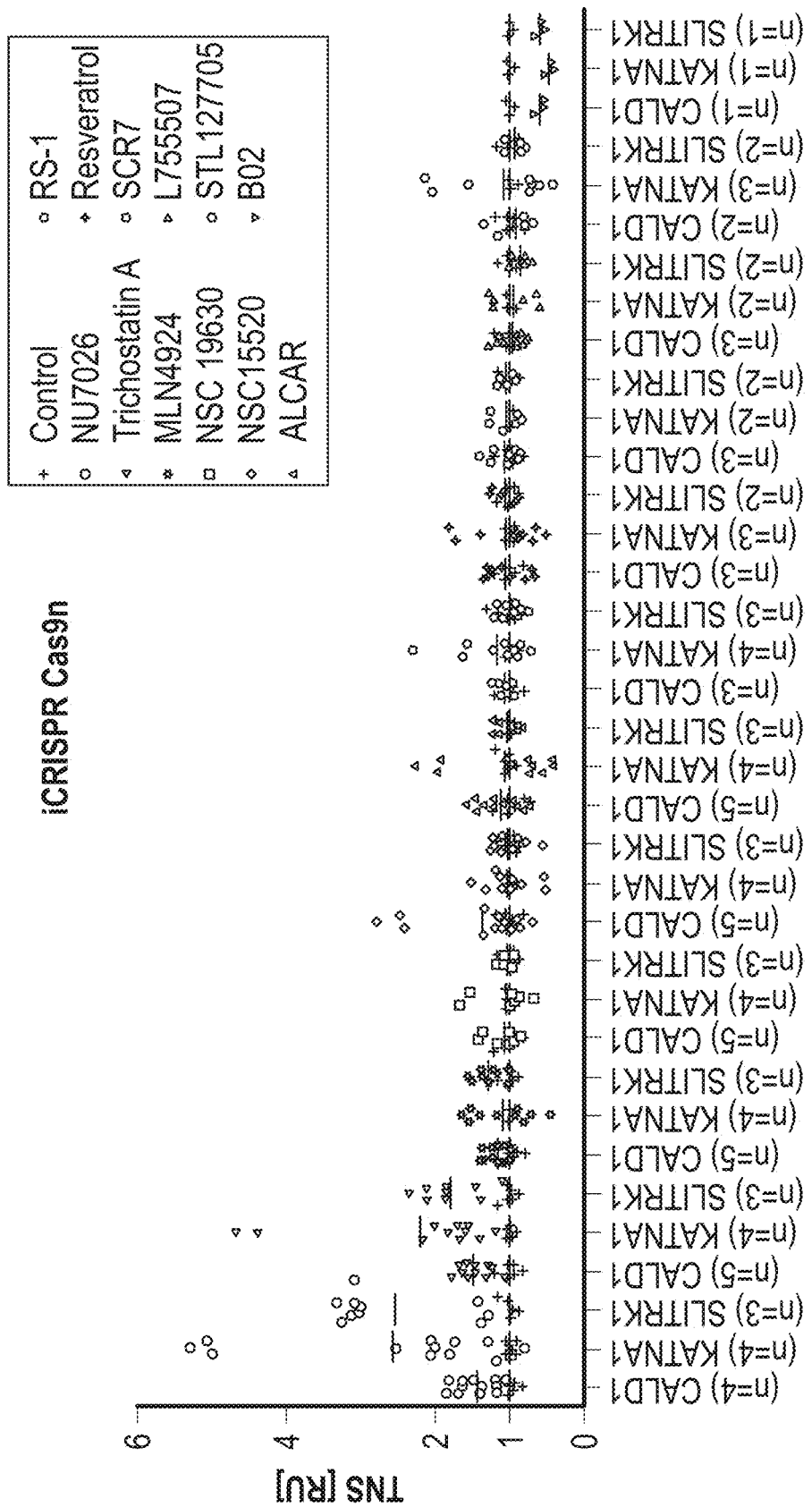

FIG. 4: Effects of small molecules on precise genome editing (PGE) efficiency in CALD1, KATNA1 and SLITRK1 with Cas9D10A and Cas9. PGE efficiency is given in relative units (RU) with the mean of controls set to 1 to account for varying efficiency in different loci. Shown are technical replicates of n independent experiments. Grey and black bars represent the mean of the control and the respective small molecule, respectively. Concentrations used were 20 µM of NU7026, 0.01 µM of Trichostatin A (TSA), 0.5 µM of MLN4924, 1 µM of NSC 19630, 5 µM of NSC 15520, 20 µM of AICAR, 1 µM of RS-1, 1 µM of Resveratrol, 1 µM of SCR7, 5 µM of L755507, 5 µM of STL127685 and 20 µM of B02.

Figure 5A:
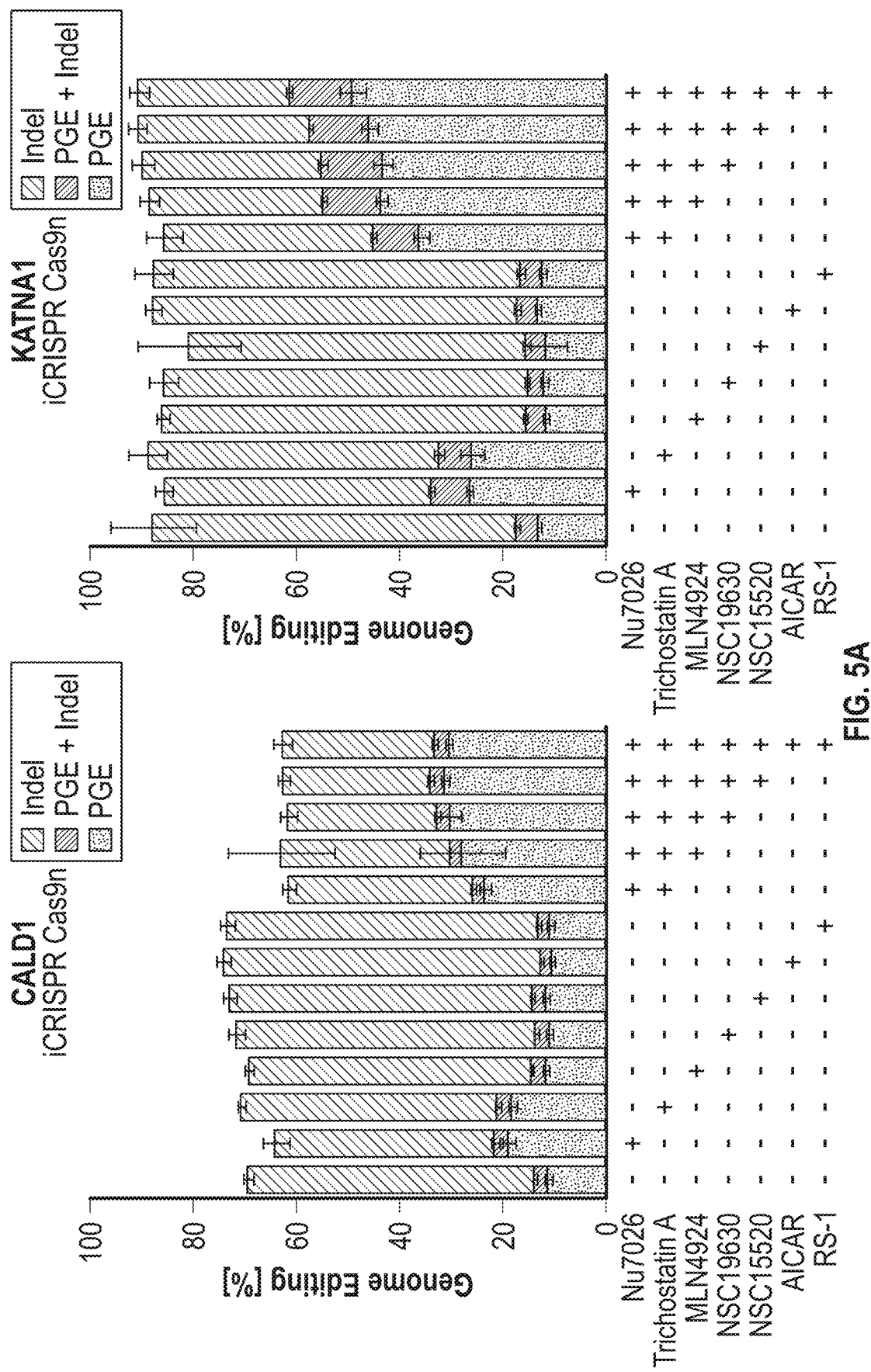
Figure 5A:
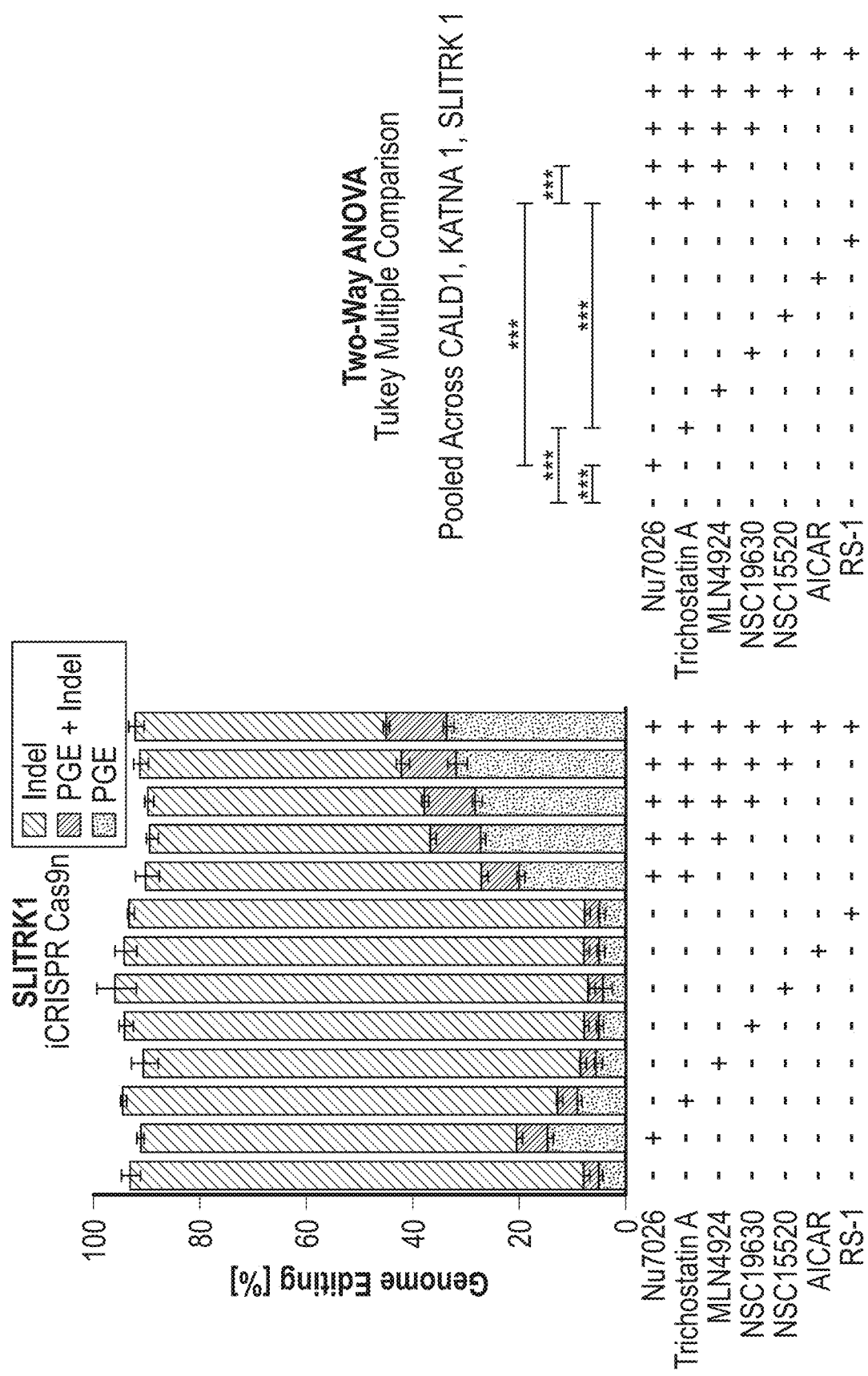
Figure 5B:
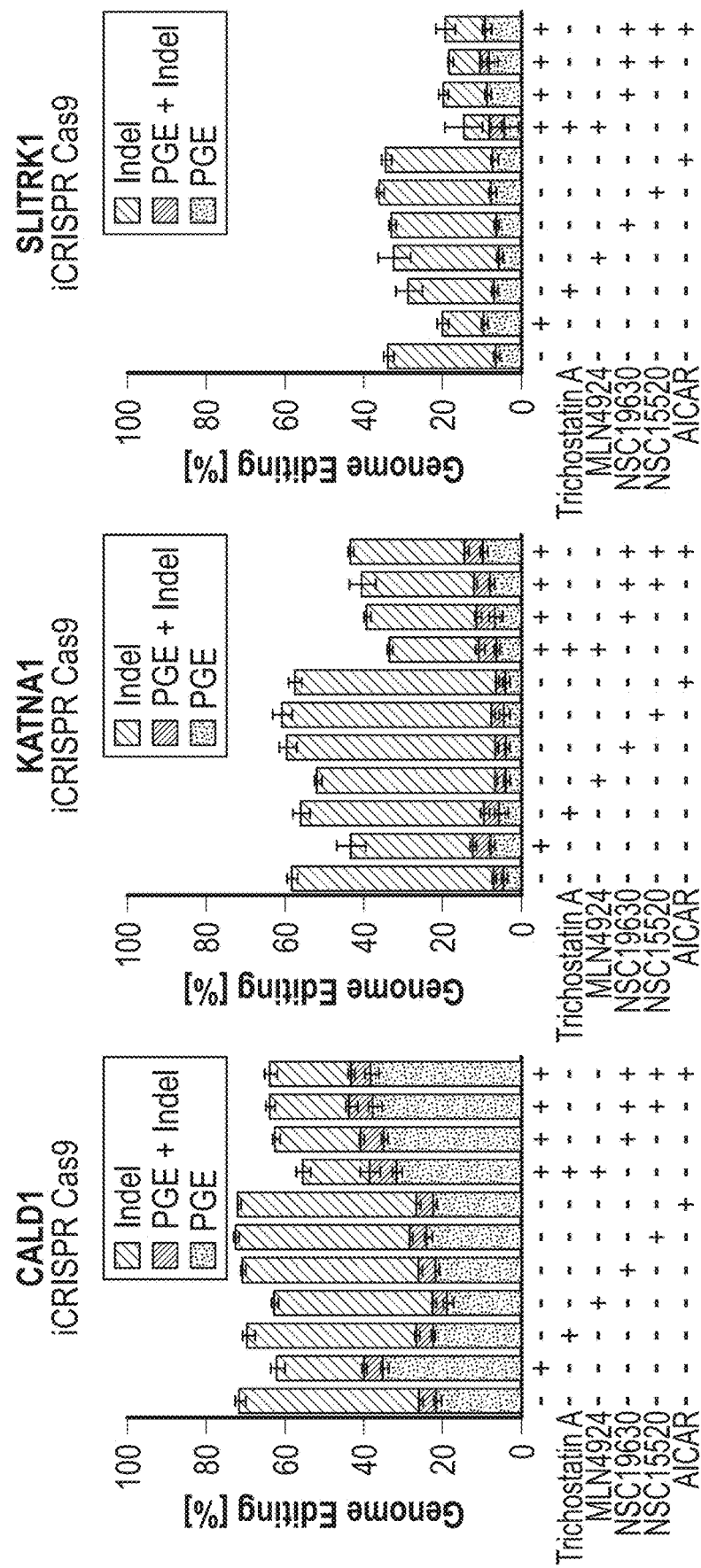
Figure 5C:
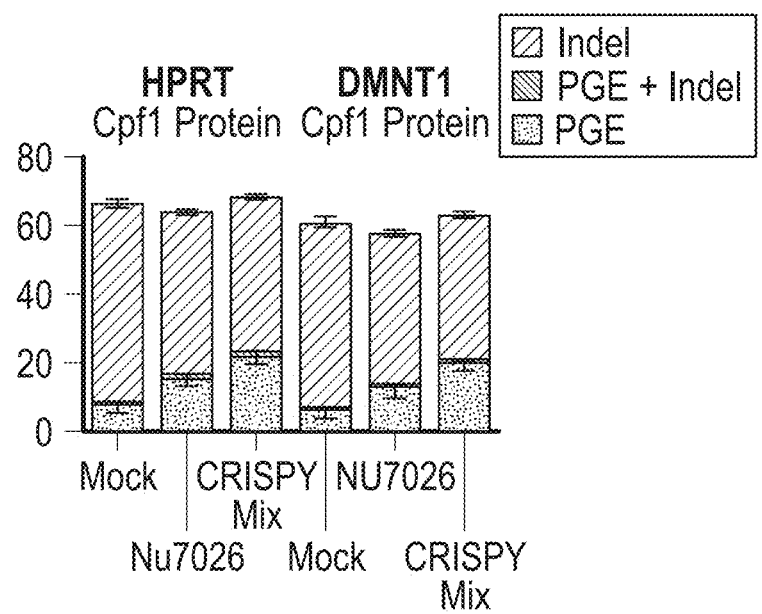
Figure 5D:
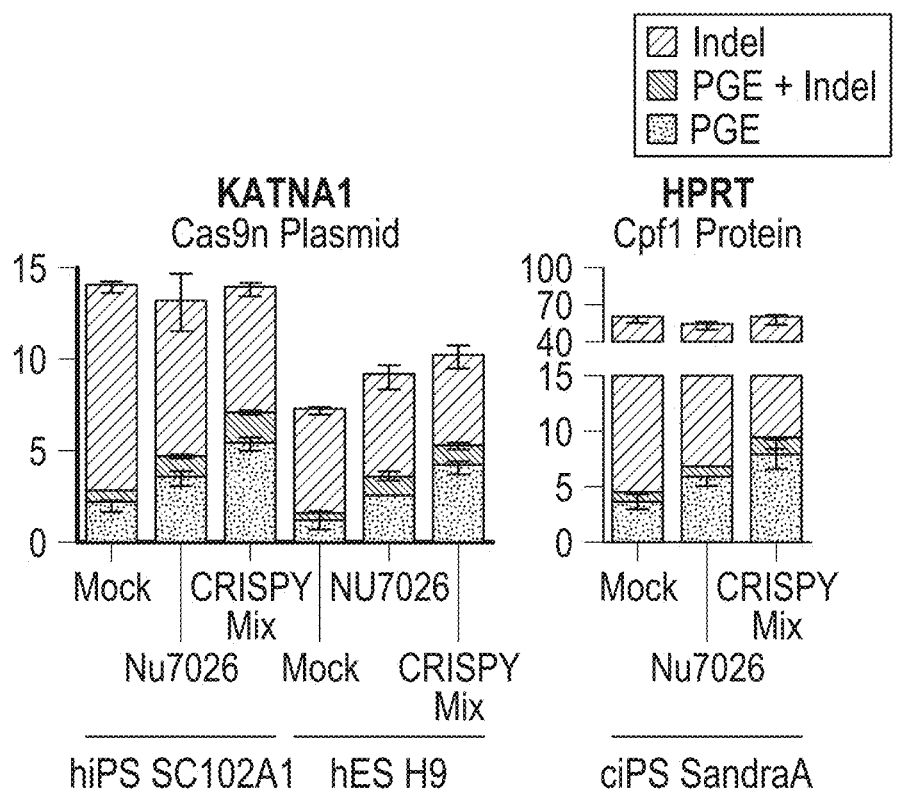

FIGS. 5A-5D: Impact of small molecule combinations on precise genome editing (PGE) efficiency in CALD1, KATNA1 and SLITRK1 with Cas9D10A and Cas9, and in HPRT and DMNT1 with Cpf1. Small molecules have an additive effect on PGE efficiency with Cas9D10A (FIG. 5A) but not with Cas9 (FIG. 5B) in the 409-B2 iCRISPR iPSC lines. PGE efficiency of HPRT and DMNT1 in 409-B2 hiPSCs with recombinant Cpf1 was increased using the CRISPY mix as well (FIG. 5C). Using the CRISPY mix, PGE efficiency was also increased in SCI 02Al hiPSCs and H9 hESCs with plasmid-delivered Cas9n-2A-GFP (GFP-FACS enriched), and in chimpanzee SandraA ciPSCs with recombinant Cpf1 (FIG. 5D). Shown are PGE, PGE+indels, and indels with green, grey or blue bars, respectively. Error bars show the standard deviation of three technical replicates for A, B and C and two technical replicates for D. Concentrations used were 20 µM of NU7026, 0.01 µM of Trichostatin A (TSA), 0.5 µM of MLN4924, 1 µM of NSC 19630, 5 µM of NSC 15520, 20 µM of AI CAR and 1 µM of RS-1. CRISPY mix indicates a small molecule mix of NU7026, TSA, MLN4924 and NSC 15520. Significances of changes in Knock-In efficiencies were determined using a two-way-ANOVA and Tukey multiple comparison pooled across the three genes CALD1, KATNA1, SLITRK1. Genes and treatments were treated as random and fixed effect, respectively. Analysis included 3 technical replicates for each gene. P values are adjusted for multiple comparison (** P≤0.01, * P≤0.001).

Figure 6A:
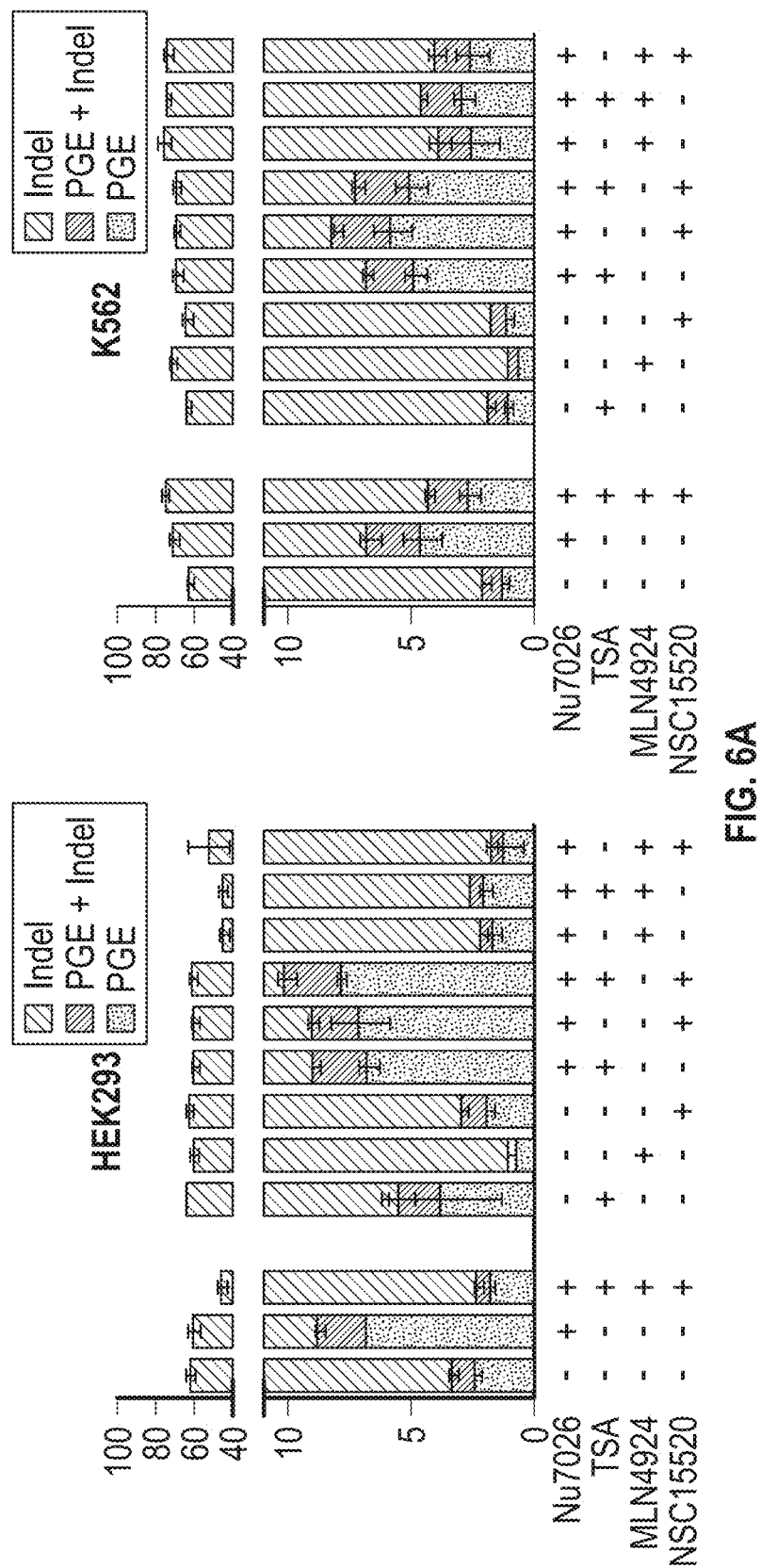
Figure 6B:
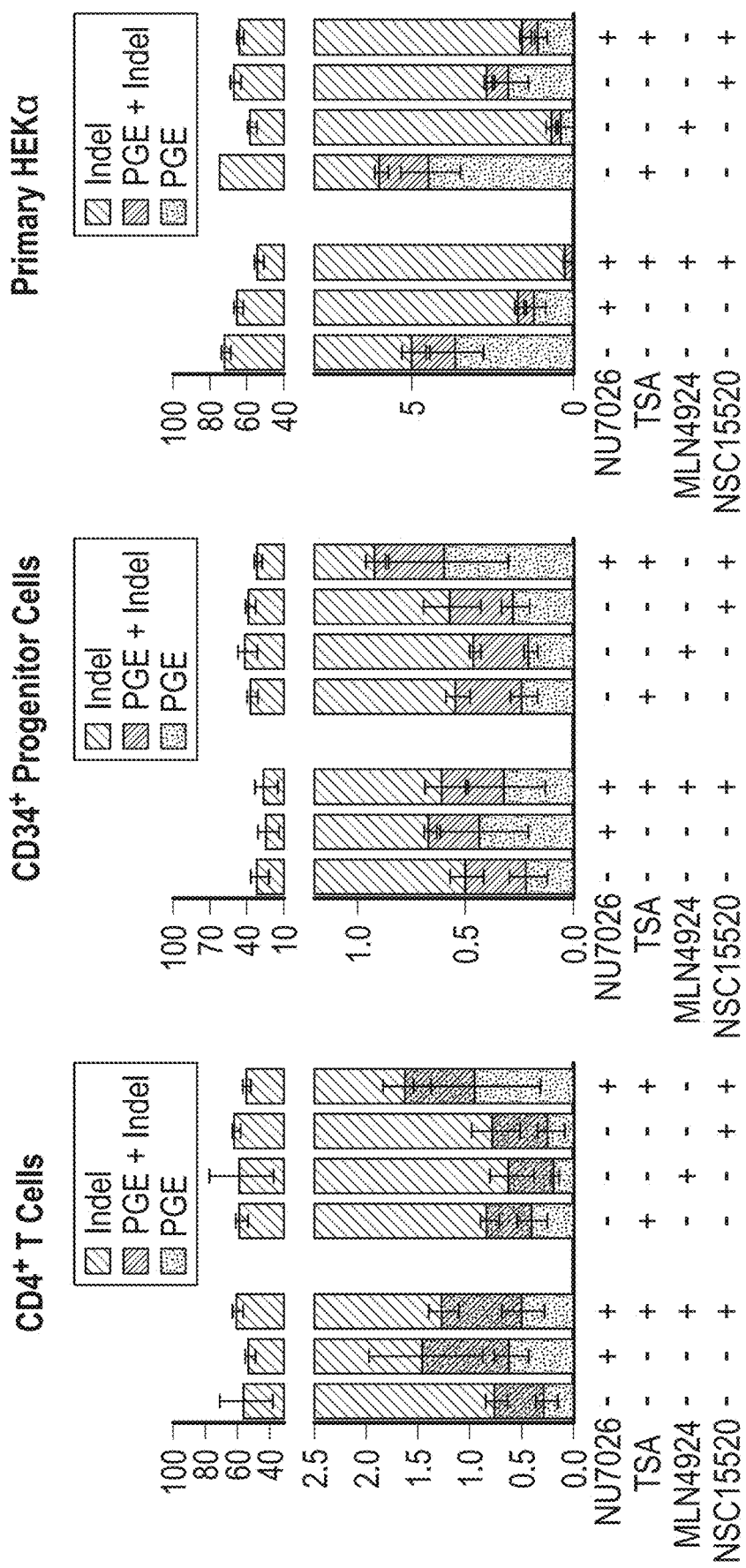

FIG. 6: Impact of the CRISPY mix and small molecule combinations on Precise Genome Editing (PGE) efficiency in HPRT with Cpf1 in non-pluripotent cell types. All possible combinations for the CRISPY mix components are shown for HEK293 and K562 cells (A). While NU7026 increases PGE efficiency, TSA and NSC15520 have no clear effect, and MLN4924 has a clear disruptive effect in those cell lines with cancer characteristics. MLN4924 has a disruptive effect on PGE efficiency in primary cells as well (B). The CRISPY mix without MLN4924 has a higher effect on PGE efficiency than NU7026 alone In $CD4^+$ T and $CD34^+$ progenitor cells. In primary Human Epidermal Keratinocytes (HEKa) also NU7026 and NSC15520 have a disruptive effect on PGE efficiency. Shown are PGE, PGE+indels, and indels with green, grey or blue bars, respectively. Error bars show the standard deviation of two independent experiments for A, and two technical replicates for each of two independent experiments for B. CRISPY mix indicates a small molecule mix of 20 µM NU7026, 0.01 µM Trichostatin A (TSA), 0.5 µM MLN4924 and 5 µM NSC 15520.

Figure 7A:
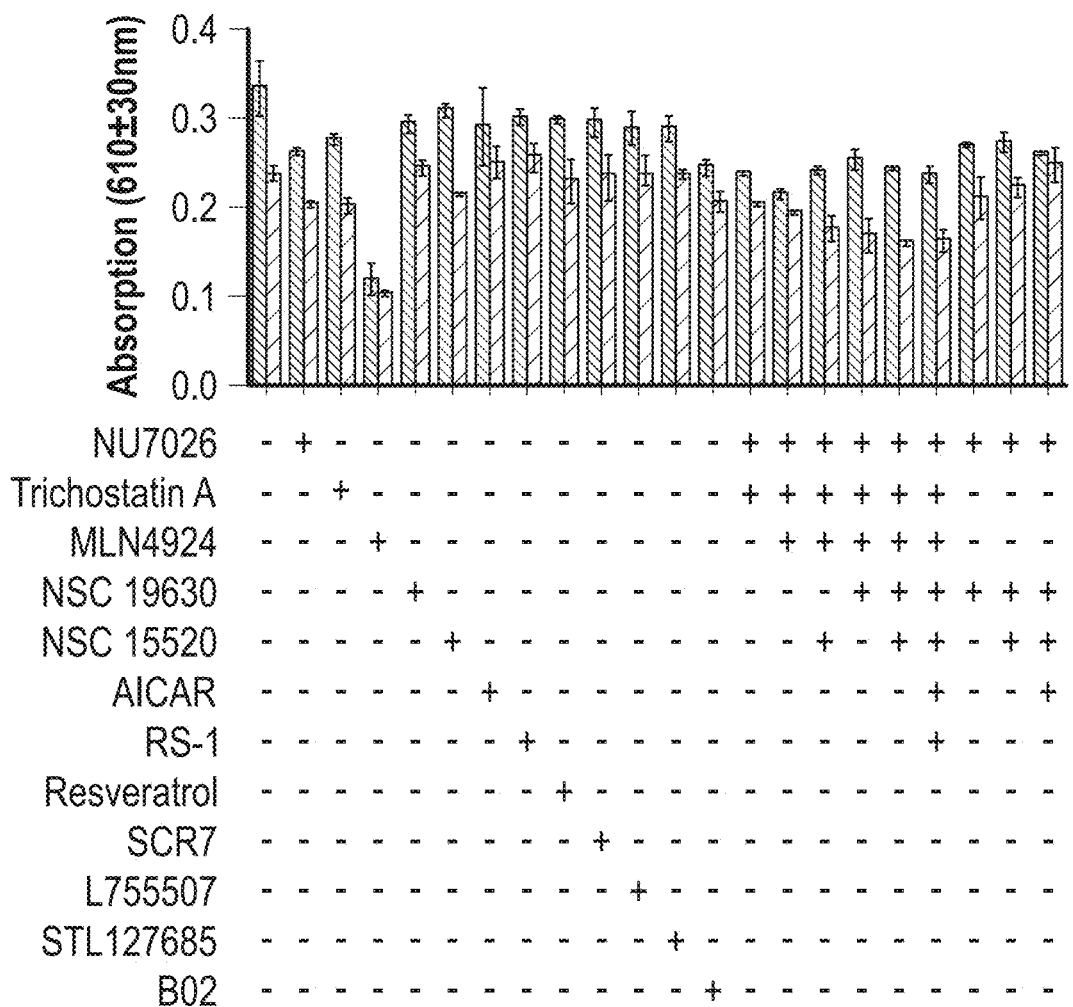

FIG. 7: Toxicity of the CRISPY mix and its components. A resazurin assay from 409-B2-iCRISPR-Cas9n cells after 24 h incubation with the small molecules and combinations from FIGS. 4 and 5, with and without RNAiMax, gRNA and ssODNs, is shown in (A). Resazurin is converted into fluorescent resorfin by cellular dehydrogenases and resulting fluorescence (Exitation: 530-570 nm, Emission: 590-620 nm) is considered as a marker for cell viability (O'Brien et al. 2000). The CRISPY mix is highlighted with black borders and is slightly toxic with no additive toxic effect of its components. Error bars show the standard deviation of two technical replicates. Karyotype analysis after 5 rounds of passaging the cells together with the CRISPY mix and mock treatment is shown in (B). At least 20 metaphases of the bulk and 5 clones of each conditions were analysed using trypsin induced giemsa staining. No numerical or large scale chromosomal aberrations, except for a small subset of metaphases from two single clones corresponding to CRISPY mix (3 of 25 metaphases polylpoid) and mock treatment (4 of 25 metaphases polyploid), were identified.

Figure 8A:
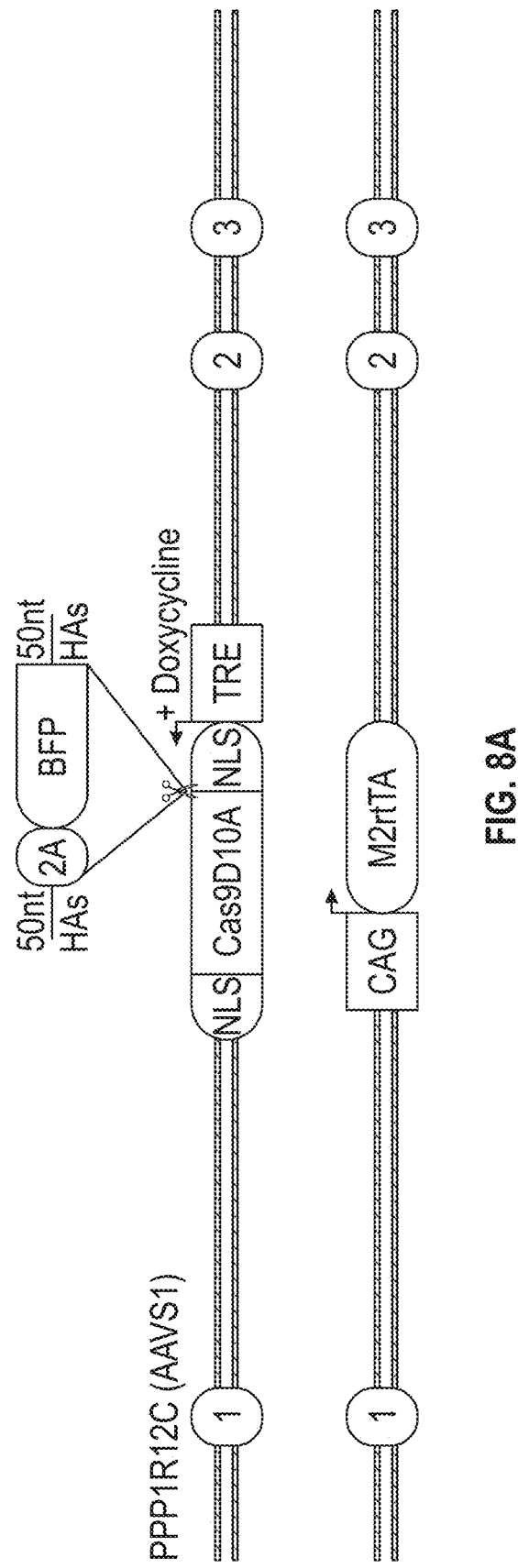

FIG. 8: Impact of the CRISPY mix and its component NU7026 on BFP insertion (ssODN) efficacy in human induced pluripotent stem cells. The design of the mtagBFP2 (Subach et al. 2011) ssODN donor and the iCRISPR system is shown in (A). We inserted a 871 nt (including 50 nt homology arms) sequence coding for a 2A-self cleaving peptide in front of a Blue Fluorescent Protein (BFP), directly after the N-terminal nuclear localization signal sequence (NLS) of the Cas9n in the heterozygous AAVS1 iCRISPR locus (409-B2 iCRISPR-Cas9n hiPSCs). If the sequence is inserted, doxycycline will lead to expression of nucleus-imported BFP. Representative images of the mock, NU7027, and CRISPY mix treatment, after 7 days of BFP expression are shown in (B) as phase contrast (PC), propidium iodide nuclei staining (PI), mtagBFP2 expression (BFP) and merge of PI and BFP. Two images (50× magnification, white size bar 200 µm) from each of three technical replicates for the respective treatments were used to quantify the percentage of cells with BFP insertion using ImageJ (C).

FIG. 9: catalytically inactive DNA-PKcs (K3753R) promotes Homology-Directed-Repair (HDR) and blocks Non-Homologous-End-Joining (NHEJ). After a Double strand Break (DSB) induced by e.g. CRISPR Cas9 or Cpf1 (light blue with gray gRNA), DNA ends are voered by Ku70/80 (orange), followed by binding of DA-PKcs (cyan), both constituting a DNA-PK complex on each DSB end (A). Autophosphorylation of DNA-PKcs leads to recruitment and activation of downstream NHEJ proteins. NHEJ outperforms HDR when DNA-PKcs is catalytically active. If DNA-PKcs is catalytically inactivated (e.g. by the K3753R mutation), autophosphorylation cannot take place and the NHEJ pathway is blocked. Kinase-inactivated DNA-PKcs leads preferential HDR repair of the DSB. The organizational structure of DNA-PKcs, with its phosphorylation clusters consisting of serines/threonines: N (residues 56 and 72), JK (residues 946 and 1003) PQR (five residues between 2023 and 2056), and ABCDE (six residues between 2609 and 2647). Some clusters activate DNA-PKcs when phosphorylated, while others disengage NHEJ or even inactive the kinase (Neal et al. 2014). Phosphorylation of the N cluster, as well as T3950, and the K3753R mutation have been shown to inactivate the kinase activity (Neal et al. 2011, Shrivastav et al. 2008, Douglas et al. 2007). DNA-PKcs and its sequence around K3753 are evolutionary conserved in vertebrates (C) (Kent et al. 2002). FIG. 9C discloses SEQ ID NOS 47, 62, 48, 63-66, and 49, respectively, in order of appearance.

FIG. 10: Catalytically inactive DNA-PKcs (K3753R) leads to almost absolute conversion of DNA double strand breaks to precise genome editing (PGE). The KR mutant leads to increased PGE compared to wildtype DNA-PKcs in 409-B2 hiPSCs, regardless of the type of double strand break introduced. Shown is increased PGE of CALD1, KATNA1, SLITRK1 and PRKDC (R3753K) with Cas9n double nicking (A), and of CALD1 with Cas9 or HPRT with Cpf1 (B). Shown are PGE, PGE+indels, and indels with green, light green or blue bars, respectively. Error bars show the standard deviation of three technical replicates for each of two independent experiments for A, and two technical replicates for B. Cells were incubated for 3 days with doxycycline to express Cas9n for double nicking of A.

FIG. 11: Efficient Multiplexed Precise Genome Editing (MPGE) of CALD1, KATNA1, and SLITRK1. Electroporation of gRNAs and ssODN DNA donors allows robust bulk precise genome editing (PGE) efficiencies for all three genes in 409-B2 hiPSCs with the DNA-PKcs KR mutation (A). Shown are PGE, PGE+indels, and indels with green, light green or blue bars, respectively. Error bars show the standard deviation of two technical replicates and cells were incubated for four days with doxycycline to express Cas9n for double nicking. The ancient mutations and silent blocking mutations are not always incorporated together in chromosomes where Targeted Nucleotide Substitution (TNS) took place and a blocking mutation distant from the other mutations can be incorporated as sole TNS (B). The double nicking guide targets (blue) and the mutations (green) for the respective genes are shown in scale. Heatmaps of genome editing events (TNS and/or indels) in chromosomes carrying CALD1, KATNA1, and SLITRK1 of 33 analysed clones are shown in (C). Most clones either remain wildtype or are precisely edited for all three genes. Heatmaps present either two chromosomes for a single gene or six chromosomes for all three genes, with incorporation of indels and incorporation of any TNS, regardless if blocking mutation or ancient mutation (left panel), or of incorporation of at least the ancient mutation (right panel). Generation of a MPGE clones is possible in less than two weeks, if single cell dilution seeding is carried out using a small portion of just electroporated cells (D). Of 56 colonies picked, 45 survived and 12 of those originated from more than one cell (based on DNA sequencing read proportions), leaving 33 clones for analysis.

Figure 12B:
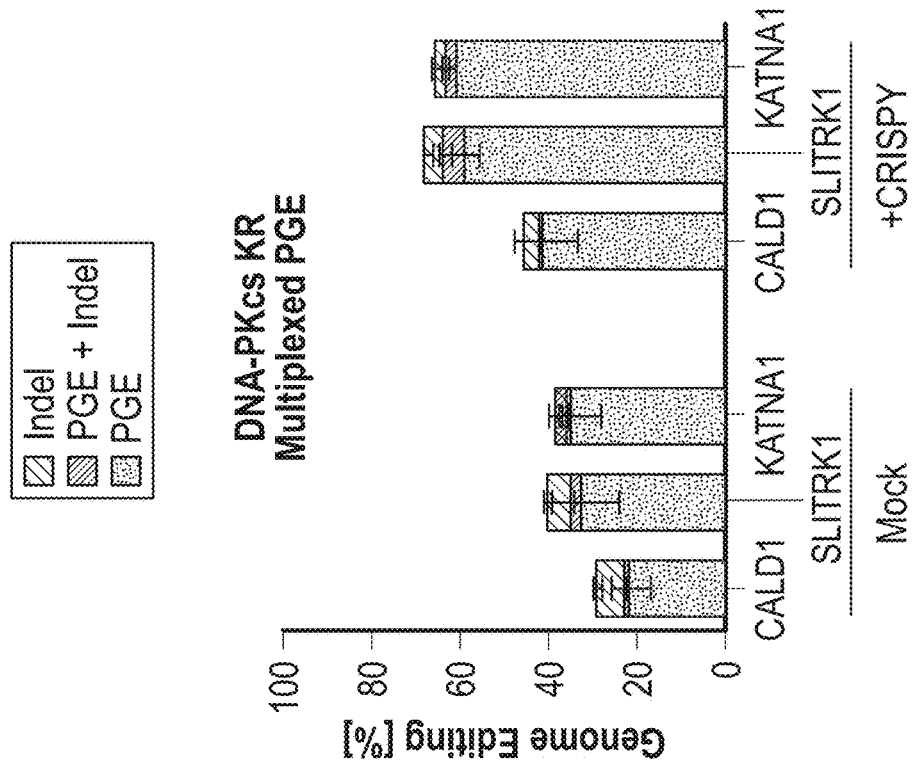
Figure 12A:
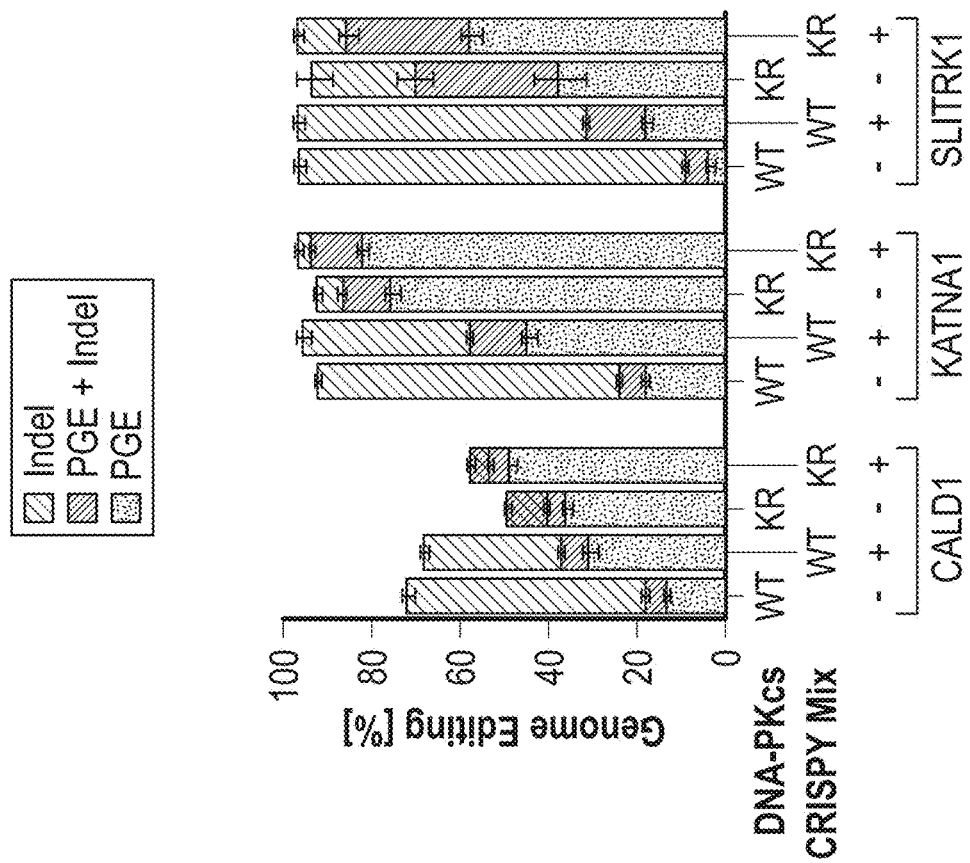

FIG. 12: Additive effect of CRISPY mix and DNA-PKcs (K3753R) on precise genome editing (PGE) efficiency in CALD1, KATNA1 and SLITRK1 with Cas9D10A. The PGE efficiency is strongly increased with the DNA-PKcs KR mutant (KR) compared to the wildtype (WT) and further increased by addition of the CRISPY mix for single genes (A), and even more for multiplexed PGE (B), where efficiencies are generally lower. Shown are PGE, PGE+indels, and indels with green, light green or blue bars, respectively. Error bars show the standard deviation of three technical replicates. CRISPY mix indicates a small molecule mix of 20 µM NU7026, 0.01 µM Trichostatin A (TSA), 0.5 µM MLN4924 and 5 µM NSC 15520. Cells were incubated for 2 days (4 days for multiplexing) with doxycycline to express Cas9n for double nicking.

Figure 13:
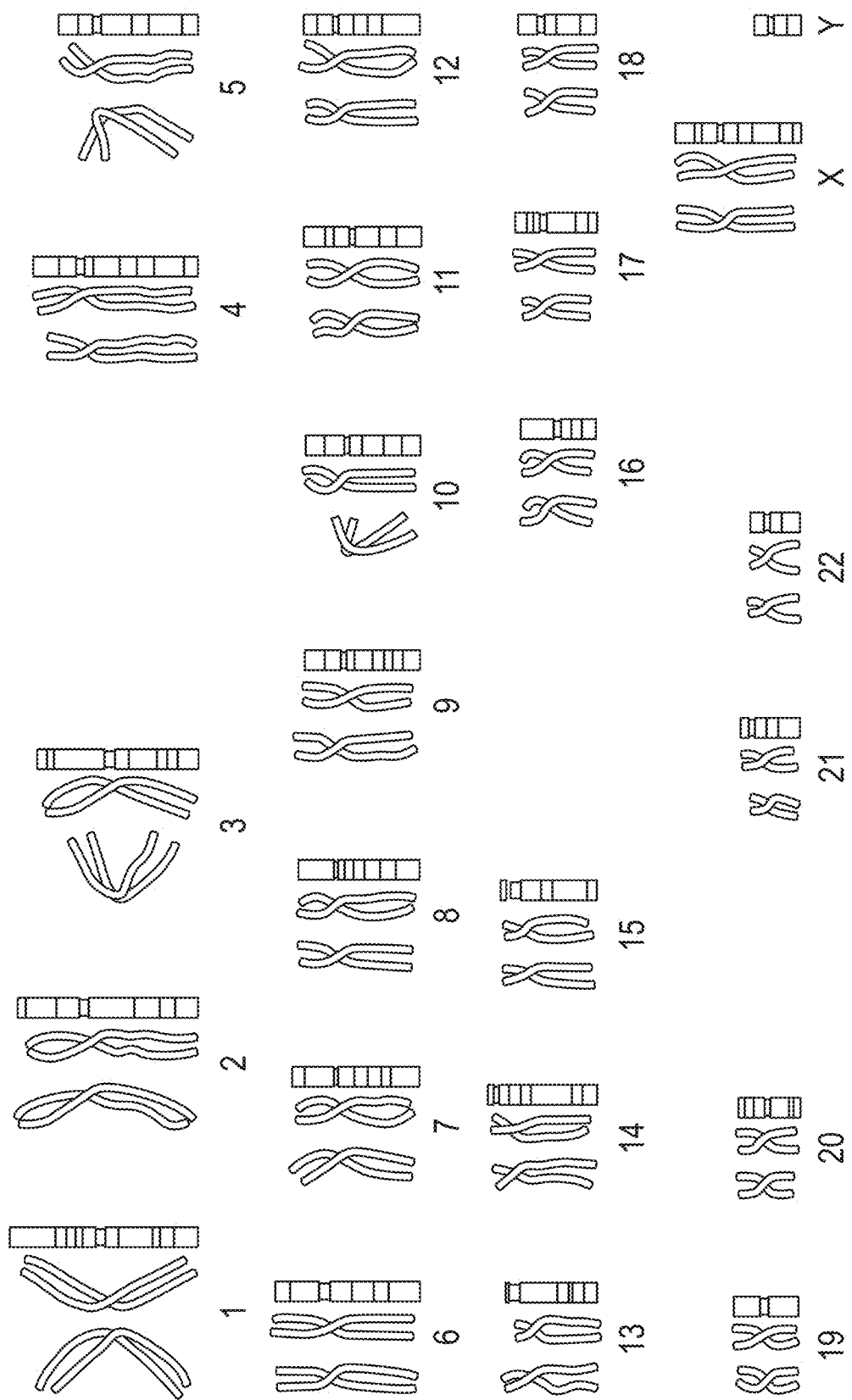

FIG. 13: Representative karyogram of 409-B2 iCRISPR hiPSCs with the DNA-PKcs KR mutation after 3 months in culture. Of 25 metaphases, analyzed by trypsin induced giemsa staining, all show a healthy karyotype (46, XX). No numerical or large scale chromosomal aberrations were identified (band number 350, gray shades 3).

METHODS

Cell Culture

Stem cell lines cultured for this project included human 409-B2 hiPSC (female, Riken BioResource Center) and SC102A1 hiPSC (male, BioCat GmbH), chimpanzee SandraA ciPSC (female, Mora-Bermúdez et al. 201637), as well as H9 hESC (female, WiCell Research Institute, Ethics permit AZ 3.04.02/0118). Stem cell lines were grown on Matrigel Matrix (Corning, 35248), and mTeSR1 (StemCell Technologies, 05851) with mTeSR1 supplement (StemCell Technologies, 05852) was used as culture media. Non-pluripotent cell types and their respective media used were: HEK293 (ECACC, 85120602) with DMEM/F-12 (Gibco, 31330-038) supplemented with 10% FBS (SIGMA, F2442) and 1% NEAA (SIGMA, M7145); K562 (ECACC, 89121407) with IMDM (ThermoFisher, 12440053) supplemented with 10% FBS; CD4+ T (HemaCare, PB04C-1) with RPMI 1640 (ThermoFisher, 11875-093) supplemented with 10% FBS, and activated with Dynabeads Human T-Activator (CD3/CD28) (ThermoFisher, 11131D); CD34+ progenitor (HemaCare, M34C-1) with StemSpan SFEM (Stemcell, 09600) supplemented with StemSpan CC110 (StemCell, 02697); and HEKa (Gibco, C0055C) with Medium 154 (ThermoFisher, M154500) and Human Keratinocyte Growth Supplement (ThermoFisher, S0015). Cells were grown at 37° C. in a humidified incubator gassed with 5% $CO_2$. Media was replaced every day for stem cells and every second day for non-pluripotent cell lines. Cell cultures were maintained 4-6 days until ~80% confluency, and subcultured at a 1:6 to 1:10 dilution. Adherent cells were dissociated using EDTA (VWR, 437012C). The media was supplemented with 10 µM Rho-associated protein kinase (ROCK) inhibitor Y-27632 (Calbiochem, 688000) after cell splitting for one day in order to increase cell survival.

Generation and Validation of iCRISPR Cell Lines

Human 409-B2 iPSCs were used to create an iCRISPR-Cas9 line as described by Gonzalez et al. (Gonzalez et al. 2014). For the production of iCRISPR-Cas9D10A line Puro- Cas9 donor was subjected to site-directed mutagenesis with the Q5 mutagenesis kit (New England Biolabs, E0554S). Primers were ordered from IDT (Coralville, USA) and are shown in Table 2. Expression of the pluripotency markers SOX2, OCT-4, TRA1-60 and SSEA4 in iCRISPR lines was validated using the PSC 4-Marker immunocytochemistry kit (Molecular Probes, A24881) (data not shown). Quantitative PCR was used to confirm doxycycline inducible Cas9 or Cas9D10A expression and digital PCR was used to exclude off-target integration of the iCRISPR cassettes (data no shown).

Small Molecules

Commercially available small molecules used in this study were NU7026 (SIGMA, T8552), TSA (SIGMA, T8552), MLN4924 (Adooq BioScience, A11260), NSC 19630 (Calbiochem, 681647), NSC 15520 (ChemBridge, 6048069), AICAR (SIGMA, A9978), RS-1 (Calbiochem, 553510), Resveratrol (Selleckchem, S1396), SCR7 (Xcess-Bio, M60082-2s), L755507 (TOCRIS, 2197), B02 (SIGMA, SML0364) and STL127685 (Vitas-M). STL127685 is a 4-fluorophenyl analog of the non-commercially available STL127705. Stocks of 15 mM (or 10 mM for NU7026) were made using dimethylsulfoxide (DMSO)(Thermo Scientific, D12345). Solubility is a limiting factor for NU7026 concentration. Suitable working solutions for different concentrations were made so that addition of each small molecule accounts for a final concentration of 0.08% (or 0.2% for NU7026) DMSO in the media. Addition of all small molecules would lead to a final concentration of 0.7% DMSO.

Design of gRNAs and ssODNs

We chose to introduce one desired mutation in three genes CALD1, KATNA1 and SLITRK1 back to the state of the last common ancestor of human and Neanderthal (Prefer et al. 2013). gRNA pairs for editing with the Cas9D10A nickase were selected to cut efficiently at a short distance from the desired mutation and from the respective partnering sgRNA. The efficiency was estimated with the sgRNA scorer 1.0 tool (Chari et al. 2015) as a percentile rank score. Donor ssODNs for nickase editing were designed to have the desired mutation and Cas9-blocking mutations to prevent re-cutting of the locus and had at least 30 nt homology arms upstream and downstream of each nick (FIG. 2). gRNA of the nickase gRNA pair that cuts closer to the desired mutation was used for Cas9 nuclease editing together with a 90 nt ssODN centered at the desired mutation and containing a Cas9-blocking mutation (FIG. 2). ssODNs for editing of HPRT and DMNT1 using Cpf1 were designed to contain a blocking mutation near the PAM site and an additional mutation near the cut. gRNAs (crRNA and tracR) and ssODN were ordered from IDT (Coralville, USA). ssODNs and crRNA targets are shown in Table 2.

Lipofection of Oligonucleotides

Cells were incubated with media containing 2 µg/ml doxycycline (Clontech, 631311) 2 days prior to lipofection. Lipofection (reverse transfection) was done using the alt-CRISPR manufacturer's protocol (IDT) with a final concentration of 7.5 nM of each gRNA and 10 nM of the respective ssODN. In brief, 0.75 µl RNAiMAX (Invitrogen, 13778075) and the respective oligonucleotides were separately diluted in 25 µl OPTI-MEM (Gibco, 1985-062) each and incubated at room temperature for 5 min. Both dilutions were mixed to yield 50 µl of OPTI-MEM including RNAiMAX, gRNAs and ssODNs. The lipofection mix was incubated for 20-30 min at room temperature. During incubation cells were dissociated using EDTA for 5 min and counted using the Countess Automated Cell Counter (Invitrogen). The lipofection mix, 100 µl containing 25.000 dissociated cells in mTeSR1 supplemented with Y-27632, 2 µg/ml doxycycline and the respective small molecule(s) to be tested were throughoutly mixed and put in one well of a 96 well covered with Matrigel Matrix (Corning, 35248). Media was exchanged to regular mTeSR1 media after 24 hours.

Oligonucleotide and Ribonucleoprotein Electroporation (Nucleofection)

The recombinant A.s. Cpf1 and S.p. Cas9 protein and electroporation enhancer was ordered from IDT (Coralville, USA) and nucleofection was done using the manufacturer's protocol, except for the following alterations. Nucleofection was done using the B-16 program (or U-14 for CD4$^+$ T cells) of the Nucleofector 2b Device (Lonza) in cuvettes for 100 µl Human Stem Cell nucleofection buffer (Lonza, VVPH-5022), or Human T Cell nucleofection buffer for CD4$^+$ T cells (Lonza, VPA-1002), and Human CD34 Cell nucleofection buffer for CD34$^+$ progenitor cells (Lonza, VPA-1003), containing 1 million cells of the respective lines, 78 pmol electroporation enhancer, 160 pmol of each gRNA (crRNA/tracR duplex for Cas9 and crRNA for Cpf1) (320 pmol for double nicking with both gRNAs for one gene), 200 pmol ssODN donor, 252 pmol CRISPR protein. For multiplexing, only gRNAs and single stranded DNA donors were electroporated, since a Cas9n expressing iCRISPR-Cas9n hiPSC line was used. Cells were counted using the Countess Automated Cell Counter (Invitrogen).

FACS-Sorting

Introduction of 2 µg plasmid DNA (pSpCas9n(BB)-2A-GFP (PX461), Addgene #48140) into cells not expressing Cas9 inducably was done using the B-16 program of the Nucleofector 2b Device (Lonza) in cuvettes for 100 µl Human Stem Cell nucleofection buffer (Lonza, VVPH-5022) containing 1 million of either SC102A1 iPSC or H9 ESC. Cells were counted using the Countess Automated Cell Counter (Invitrogen). 24 h after nucleofection cells were dissociated using Accutase (SIGMA, A6964), filtered to obtain a single cell solution, and subjected to fluorescence associated cell sorting (FACS) for GFP expressing cells. During sorting with the BD FACSAria III (Becton-Dickinson) cells were kept at 4° C. in mTeSR1 supplemented with Y-27632. 48 h after sorting cells were subjected to lipofection with sgRNAs, ssODNs and treatment with small molecules.

Illumina Library Preparation and Sequencing

Three days after lipofection cells were dissociated using Accutase (SIGMA, A6964), pelleted, and resuspended in 15 µl QuickExtract (Epicentre, QE0905T). Incubation at 65° C. for 10 min, 68° C. for 5 min and finally 98° C. for 5 min was performed to yield ssDNA as a PCR template. Primers for each targeted loci of CALD1, KATNA1 and SLITRK1 containing adapters for Illumina sequencing were ordered from IDT (Coralville, USA). PCR was done in a T100 Thermal Cycler (Bio-Rad) using the KAPA2G Robust PCR Kit (Peqlab, 07-KK5532-03) with supplied buffer B and 3 µl of cell extract in a total volume of 25 µl. The thermal cycling profile of the PCR was: 95° C. 3 min; 34×(95° 15 sec, 65° C. 15 sec, 72° C. 15 sec); 72° C. 60 sec. P5 and P7 Illumina adapters with sample specific indices were added in a second PCR reaction (Kircher et al. 2012) using Phusion HF MasterMix (Thermo Scientific, F-531L) and 0.3 µl of the first PCR product. The thermal cycling profile of the PCR was: 98° C. 30 sec; 25× (98° 10 sec, 58° C. 10 sec, 72° C. 20 sec); 72° C. 5 min. Amplifications were verified by size separating agarose gel electrophoresis using EX gels (Invitrogen, G4010-11). The indexed amplicons were purified using Solid Phase Reversible Immobilization (SPRI) beads (Meyer, Kircher 2010). Double-indexed libraries were sequenced on a MiSeq (Illumina) giving paired-end sequences of 2×150 bp. After base calling using Bustard (Illumina) adapters were trimmed using leeHom (Renaud et al. 2014).

Sequence Data Analysis

CRISPresso (Pinello et al. 2016) was used to analyse sequencing data from CRISPR genome editing experiments for percentage of wildtype, targeted nucleotide substitutions (TNS), indels and mix of TNS and indels. Parameters used for analysis were '-w 20', '--min_identity_score 70' and '--ignore_substitutions' (analysis was restricted to amplicons with a minimum of 70% similarity to the wildtype sequence and to a window of 20 bp from each gRNA; substitutions were ignored, as sequencing errors would be falsely characterized as NHEJ-events). Sequencing data from colonies after single cell seeding (FIGS. 3B and C) was further analyzed by evaluating the actual read sequences using SAMtools. Clonal colonies were differentiated from mixed colonies using sequence read proportions. Colonies were counted as clones if the clear majority of reads consisted of a single sequence (homozygous) or of two sequences of similar read count (heterozygous). Each cell was assumed to have two chromosomes, since we showed a healthy karyotype. Integrated blocking mutations, ancient mutations, as well as indels for each chromosome of the cells of a clone were noted.

Statistical Analysis

Significances of changes in TNS efficiencies were determined using a two-way-ANOVA and Tukey multiple comparison pooled across the three genes CALD1, KATNA1, SLITRK1. Genes and treatments were treated as random and fixed effect, respectively. Hence, we tested the effect of treatment against its interaction with gene (Zar 1999). Analysis included 3 technical replicates for each gene. We checked for whether the assumptions of normally distributed and homogeneous residuals were fulfilled by visual inspection of a QQ-plot (Field 2005) and residuals plotted against fitted values (Quinn & Keough 2002). These indicated residuals to be roughly symmetrically distributed but with elongated tails (i.e., too large positive and negative residuals) and no obvious deviations from the homogeneity assumption. P values are adjusted for multiple comparison. Statistical analysis was done using R.

Resazurin Assay

409-B2 iCRISPR-Cas9n hiPSCs were either seeded with or without editing reagents (RNAiMax, gRNA and ssODN donor for KATNA1 editing) as described in 'Lipofection of oligonucleotides'. The media was supplemented with small molecules or combinations of small molecules, and each condition was carried out in duplicate. After 24 h media was aspirated and 100 µl fresh media together with 10 µl resazurin solution (Cell Signaling, 11884) was added. Resazurin is converted into fluorescent resorfin by cellular dehydrogenases and resulting fluorescence (Exitation: 530-570 nm, Emission: 590-620 nm) is considered as a linear marker for cell viability (O'Brien et al. 2000). Cells were incubated with resazurin at 37° C. The redox reaction was measured every hour by absorbance readings using a Typhoon 9410 imager (Amershamn Biosciences). After 5 h the absorbance scan showed a good contrast without being saturated, and was used to quantify the absorbance using ImageJ and the 'ReadPlate' plugin. Duplicate wells with media and resazurin, but without cells, were used a blank.

Microscopy and Image Analysis

409-B2 iCRISPR-Cas9n hiPSCs were nucleofected with gRNAs and the Blue Fluorescent Protein (BFP) single stranded oligo (FIG. 8A, 330 ng) in two technical replicates for either mock, NU7026, and CRISPY mix treatment. Media was supplemented with 2 µg/ml doxycycline (Clontech, 631311) for 7 days, to allow expression of nuclear imported BFP in precisely edited cells. Then, cells were fixed with 4% formaldehyde in DPBS (ThermoFisher, A24881) for 15 min, permeablized with 1% saponin in DPBS (ThermoFisher, A24881) supplemented with 100 µg/ml RNAseA (ThermoFisher, EN0531) and 40 µg/ml propidium iodide (ThermoFisher, P3566) for 45 min at 37° C., and washed three times with DPBS. Nucleic acid intercalating propidium iodide was used to counterstain nuclei. A fluorescent microscope Axio Observer Z (Zeiss) was used to aquire two images (50× magnification), from each of three technical replicates for the respective treatments, consisting of: phase contrast, HcRed channel (BP 580-604 nm, BS 615 nm, BP 625-725 nm, 10.000 ms), and DAPI channel (BP 335-383 nm, BS 395 nm, BP 420-470 nm, 20.000 ms). Images were blinded and BFP positive nuclei were counted using the Adobe Photoshop CS5 counting tool. Propidium iodide positive nuclei were quantified using ImageJ by dividing the area of nuclei (default threshold) with the mean area of a single nucleus.

Karyotyping

Microscopic analysis of the karyotype was done after trypsin induced giemsa staining. The analysis was carried out according to international quality guidelines (ISCN 2016: An International System for Human Cytogenetic Nomenclature48) by the 'Sächsischer Inkubator für klinische Translation' (Leipzig, Germany).

Study Design

We aimed to test the precise genome editing efficiency of several small molecules in iPSCs. The compounds SCR7, L755507 and RS-1 have been indicated in the literature as potential CRISPR-Cas effectors, whereas the other test compounds have not yet been known for this purpose. The test compounds are shown in Table 1.

TABLE 1

Overview of the small molecules evaluated in this study. The protein targeted, its function, as well as its respective pathway and the function of the small molecule are shown. Literature references with an asterisk indicate the small molecule as a CRISPR-Cas effector. Abbreviations: alternative NHEJ (Alt-NHEJ), damage dependent signaling (DDS).

| Pathway | Protein | Protein function | Small molecule | Small molecule function | Reference |
|---|---|---|---|---|---|
| NHEJ | Ku70/80 | First proteins to bind to DNA ends | STL127685 | 4-fluorophenyl analog of a Ku70/80 inhibitor | Weterings et al. 2016 |
| | DNA-PK | Complex of Ku70/80 and DNA-PKcs, DNA-PKcs phosphorylates itself and downstream effectors at the repair site | NU7026 | DNA-PK inhibitor | Suzuki et al. 2016* |

TABLE 1-continued

Overview of the small molecules evaluated in this study. The protein targeted, its function, as well as its respective pathway and the function of the small molecule are shown. Literature references with an asterisk indicate the small molecule as a CRISPR-Cas effector. Abbreviations: alternative NHEJ (Alt-NHEJ), damage dependent signaling (DDS).

| Pathway | Protein | Protein function | Small molecule | Small molecule function | Reference |
|---|---|---|---|---|---|
| | Ligase IV | End-processing ligation | SCR7 | Ligase IV inhibitor | Maruyama et al. 2015* |
| Alt-NHEJ (NHEJ) | WRN helicase | DNA unwinding | NSC 19630 | WRN helicase inhibitor | Aggarwal et al. 2011 |
| HDR | CtIP | DNA end resection | MLN4924 | NAE inhibitor, inhibts neddylation of CtIP | Jimeno et al. 2015 |
| | RPA | Coating and stabilization of ssDNA | NSC15520 | Inhibits binding of RPA to p53 and RAD9 | Glanzer et al. 2011, 2013 |
| | RAD52 | ssDNA annealing | AICAR | RAD52 inhibitor | Sullivan et al. 2016 |
| | RAD51 | Strand invasion with the donor DNA | RS-1  B02 | RAD51 enhancer  RAD51 inhibitor | Song et al. 2016*  Huang et al. 2011 |
| DDS | ATM | Phosphorylates many DNA repair proteins | Resveratrol | Direct stimulatory effects on purified ATM | Lee et al. 2014 |
| | | | TSA | Histone deacetlyase inhibitor, induces phosphorylation of Ser1981 in ATM | Lee 2007 |
| ? | β3-adrenergic receptor | Involved in activation of adenylate cyclase | L755507 | β3-adrenergic receptor agonist | Yu et al. 2015* |

As a tool for analysis of effects of small molecules on HDR efficiency, we generated an iCRISPR-Cas9 and iCRISPR-Cas9D10A iPSC line that allows for doxycycline inducible Cas9 or Cas9D10A expression and efficient delivery of ssODN and guide RNAs (gRNAs) (Gonzalez et al. 2014). The genome editing and analysis flowchart is shown in FIG. 1. The design of gRNAs, ssODNs and Primers used in the editing of three example genes CALD1, KATNA1 and SLITRK1 is shown in FIG. 2 and Table 2.

TABLE 2

Oligonucleotides used in this study. gRNA (crRNA target) and single stranded DNA donors (ssODNs) for editing of CALD1, KATNA1, SLITRK1, HPRT, DMNT1, AAVS1-iCRISPR, and PRKDC, as well as primers for analysis and Q5 site-directed-mutagenesis of the Cas9 iCRISPR donor plasmid are shown. Mutations are in bold letters and ancestral mutations are underlined as well. The donors KATNA1 Cas9D10A 2 and SLITRK1 Cas9D10A 2 have different silent mutations and were used for FIG. 10-12.

| | | |
|---|---|---|
| gRNAs | CALD1 t1 | TGGAGACTATTGCTGCTTGA (SEQ ID NO. 1) |
| | CALD1 t2 | GCAGTATACCAGTGCAATTG (SEQ ID NO. 2) |
| | KATNA1 t1 | AAATGATGACCCTTCCAAAA (SEQ ID NO. 3) |
| | KATNA1 t2 | CAACACCTAAAATAAGGGTA (SEQ ID NO. 4) |
| | SLITRK1 t1 | GCTAACAGTTTACCCTGCCC (SEQ ID NO. 5) |
| | SLITRK1 t1 | ACCCGTCGCTATCGCTGCTG (SEQ ID NO. 6) |
| | HPRT t1 | GGTTAAAGATGGTTAAATGAT (SEQ ID NO. 7) |
| | DMNT1 t1 | CTGATGGTCCATGTCTGTTAC (SEQ ID NO. 8) |
| | iCRISPR BFP insertion t1 | TGTCGGCTGCTGGGACTCCG (SEQ ID NO. 9) |
| | iCRISPR BFP insertion t2 | TACAGCATCGGCCTGGCTAT (SEQ ID NO. 10) |
| | PRKDC t1 | GGTCCTCGCCACCCTTCACC (SEQ ID NO. 11) |
| | PRKDC t2 | GCGCGTGGAGCAGCTCTTCC (SEQ ID NO. 12) |

TABLE 2-continued

Oligonucleotides used in this study. gRNA (crRNA target) and single stranded DNA donors (ssODNs) for editing of CALD1, KATNA1, SLITRK1, HPRT, DMNT1, AAVS1-iCRISPR, and PRKDC, as well as primers for analysis and Q5 site-directed-mutagenesis of the Cas9 iCRISPR donor plasmid are shown. Mutations are in bold letters and ancestral mutations are underlined as well. The donors KATNA1 Cas9D10A 2 and SLITRK1 Cas9D10A 2 have different silent mutations and were used for FIG. 10-12.

|  | PRKDC t1-back | GGTCCTCGCCACCTCTCACC<br>(SEQ ID NO. 13) |
|---|---|---|
| ssODNs | CALD1 Cas9 | GTATACTGCTCCAGTCTGCTGTCAATCTTGGAGACTACTGCTGCTTGATGGG<br>TCGATTTGACACCACTGCTAAAAAAGTAAACACATACA<br>(SEQ ID NO. 14) |
|  | CALD1 Cas9D10A | TTATATGTATGTGTTTACTTTTTTAGCAGTGGTGTCAAATCGACCCATCAAG<br>CTGCAGTAGTCTCCAAGATTGACAGCAGACTGGAGCAGTATACCAGTGCTAT<br>TGAGGTGAGAATTGTCCTCAGCGTTATGGTCCTGCTGAACAGAAATAGA<br>(SEQ ID NO. 15) |
|  | KATNA1 Cas9 | GAAGGGTCATCATTTTCAGAAGCACCTCCAACACCTAAAATAAGGGAAAGGG<br>GAGAGTGAAAAGATATTAAGTTGGATTATACCAAATG<br>(SEQ ID NO. 16) |
|  | KATNA1 Cas9D10A | CTCATCTATATCCCAGGGAAAATTAGTAGCTGCCAGAACCATAACCATTTTA<br>GAAGGGTCATCATTTTCAGAGGCGCCTCCAACACCTAAAATAACGGTAAGGG<br>GAGAGTGAAAAGATATTAAGTTGGATTATACCAAATGAAGCT<br>(SEQ ID NO. 17) |
|  | KATNA1 Cas9D10A 2 | CTCATCTATATCCCAGGGAAAATTAGTAGCTGCCAGAACCATAACCATTTTA<br>GAAGGGTCATCATTTTCAGAAGCACCTCCAACACCTAAAATAACGGTAAGGG<br>GAGAGTGAAAAGATATTAAGTTGGATTATACCAAATGAAGCT<br>(SEQ ID NO. 18) |
|  | SLITRK1 Cas9 | TGTTAGCTAAGGGTTTGTTCCTGGCGCTACCCGTCGCTATCGCTGCGGTGGG<br>TCTGATTTTGATCTGCCAGTTGCCTGGGATCTTTGTAC<br>(SEQ ID NO. 19) |
|  | SLITRK1 Cas9D10A | TCATCTTTAAACCCGACCCTGGGATGTGGTCGCAGCTGCAGCCCCCAGGACA<br>GGGTAAACTGTTAGCTAAGGGTTTGTTCCTGGCACTGCCCGTCGCTATCGCT<br>GCGGTGGGTCTGATTTTGATCTGCCAGTTGCCTGGGATCTTTGTACCTCCG<br>(SEQ ID NO. 20) |
|  | SLITRK1 Cas9D10A 2 | TCATCTTTAAACCCGACCCTGGGATGTGGTCGCAGCTGCAGCCCCCAGGGCA<br>TGGTAAACTGTTAGCTAAGGGTTTGTTCCTGGCGCTACCCGTCGCTATCGCA<br>GCTGTGGGTCTGATTTTGATCTGCCAGTTGCCTGGGATCTTTGTACCTCCG<br>(SEQ ID NO. 21) |
|  | HPRT Cpf1 | GCCATTTCACATAAAACTCTTTTAGGTTATAGATGGTTAAATGAATGACAAA<br>AAAAGTAATTCACTTACAGTCTGGCTTATATCCAACAC<br>(SEQ ID NO. 22) |
|  | DMNT1 Cpf1 | TTAACATCAGTACGTTAATGTTTCCTGATCGTCCATGTCTGTTAGTCGCCTG<br>TCAAGTGGCGTGACACCGGGCGTGTTCCCCAGAGTGAC<br>(SEQ ID NO. 23) |
|  | mtagBFP-iCRISPR-Cas9n | AAAGACGATGACGATAAGATGGCCCCAAAGAAGAAGCGGAAGGTCGGTATCC<br>ACGGAGTCCCAGCAGCCGTGAGCAAGGGCGAGGAGCTGATCAAGGAGAACAT<br>GCACATGAAGCTGTACATGGAGGGCACCGTGGACAACCACCACTTCAAGTGC<br>ACCAGCGAGGGCGAGGGCAAGCCCTACGAGGGCACCCAGACCATGCGCATCA<br>AGGTGGTGGAGGGCGGCCCCCTGCCCTTCGCCTTCGACATCCTGGCCACCAG<br>CTTCCTGTACGGCAGCAAGACCTTCATCAACCACACCCAGGGCATCCCCGAC<br>TTCTTCAAGCAGAGCTTCCCCGAGGGCTTCACCTGGGAGCGCGTGACCACCT<br>ACGAGGACGGCGGCGTGCTGACCGCCACCCAGGACACCAGCCTGCAGGACGG<br>CTGCCTGATCTACAACGTGAAGATCCGCGGCGTGAACTTCACCAGTAATGGG<br>CCTGTGATGCAGAAGAAGACTCTGGGCTGGGAGGCATTCACCGAGACCCTCT<br>ATCCGGCTGATGGTGGGCTCGAGGGTCGCAACGATATGGCTTTGAAACTCGT<br>CGGAGGAAGTCACCTCATCGCAAACGCTAAAACAACCTATAGGTCTAAGAAG<br>CCCGCCAAGAACTTGAAAATGCCAGGGGTCTACTATGTAGATTACCGCTTGG<br>AACGAATTAAAGAGGCTAATAATGAGACTTACGTAGAACAACACGAGGTAGC<br>AGTCGCTCGATATTGCGACTTGCCGAGTAAGCTCGGACATAAGCTGAACGGC<br>AGTGGAGAAGGTCGGGGATCACTCCTGACGTGTGGAGATGTTGAAGAGAACC<br>CCGGCCCCGACAAGAAGTACAGCATCGGCCTGGCCATCGGCACCAACTCTGT<br>GGGCTGGGCCGTGATCACCGACGAGTACAAGGTGCCCA<br>(SEQ ID NO. 24) |
|  | PRKDC Cas9n | GCGAAGGCCCAAGCGCATCATCATCCGTGGCCATGACGAGAGGGAACACCCT<br>TTCCTGGTGAGAGGTGGCGAGGACCTGCGGCAGGACCAGCGCGTGGAGCAGC<br>TCTTCCAGGTCATGAATGGGATCCTGGCCCAAG<br>(SEQ ID NO. 25) |

TABLE 2-continued

Oligonucleotides used in this study. gRNA (crRNA target) and single stranded
DNA donors (ssODNs) for editing of CALD1, KATNA1, SLITRK1, HPRT, DMNT1, AAVS1-
iCRISPR, and PRKDC, as well as primers for analysis and Q5 site-directed-mutagenesis
of the Cas9 iCRISPR donor plasmid are shown. Mutations are in bold letters and
ancestral mutations are underlined as well. The donors KATNA1 Cas9D10A 2 and
SLITRK1 Cas9D10A 2 have different silent mutations and were used for FIG. 10-12.

| | | |
|---|---|---|
| | PRKDC-back Cas9n | GCGAAGGCCCAAGCGCATCATCATCCGTGGCCATGACGAGAGGGAACACCCT TTCCTGGTGAAGGGTGGCGAGGACCTGCGGCAGGACCAGCGCGTGGAGCAGC TCTTCCAGGTCATGAATGGGATCCTGGCCCAAG (SEQ ID NO. 26) |
| Primers | CALD1 forward | ACACTCTTTCCCTACACGACGCTCTTCCGATCTGCTAATCAGCTAGCATATG TATGAGAA (SEQ ID NO. 27) |
| | CALD1 reverse | GTGACTGGAGTTCAGACGTGTGCTCTTCCGATCTTTGGACTTGATTATTGTC CTAAGTG (SEQ ID NO. 28) |
| | KATNA1 forward | ACACTCTTTCCCTACACGACGCTCTTCCGATCTCCTGACGGCAAAGGAATAT AG (SEQ ID NO. 29) |
| | KATNA1 reverse | GTGACTGGAGTTCAGACGTGTGCTCTTCCGATCTACTGTGCTTCCTTGTATT GTTGT (SEQ ID NO. 30) |
| | SLITRK1 forward | ACACTCTTTCCCTACACGACGCTCTTCCGATCTGGGCTTCAAATCAGCCAAG (SEQ ID NO.31) |
| | SLITRK1 reverse | GTGACTGGAGTTCAGACGTGTGCTCTTCCGATCTTTTCAAGACAAATGGGCA AG (SEQ ID NO. 32) |
| | HPRT forward | ACACTCTTTCCCTACACGACGCTCTTCCGATCTGGTGAAAAGGACCCCACGAA (SEQ ID NO. 33) |
| | HPRT reverse | GTGACTGGAGTTCAGACGTGTGCTCTTCCGATCTTGGCAAATGTGCCTCTCTA CAAAT (SEQ ID NO. 34) |
| | DMNT1 forward | ACACTCTTTCCCTACACGACGCTCTTCCGATCTTGAACGTTCCCTTAGCACTC TG (SEQ ID NO. 35) |
| | DMNT1 reverse | GTGACTGGAGTTCAGACGTGTGCTCTTCCGATCTCCTTAGCAGCTTCCTCCTC C (SEQ ID NO. 36) |
| | Q5 D10A forward | TGGTGCCGATAGCCAGGCCGATG (SEQ ID NO. 37) |
| | Q5 D10A reverse | ACTCTGTGGGCTGGGCCG (SEQ ID NO. 38) |
| | PRKDC forward | ACACTCTTTCCCTACACCACGCTCTTCCGATCTCTAGCCTGTGCCCTGAGATG (SEQ ID NO. 39) |
| | PRKDC reverse | GTGACTGGAGTTCAGACGTGTGCTCTTCCGATCTGCACAACGCTATAGGTCCT CA (SEQ ID NO. 40) |

Small molecules that we chose to test for their ability to block NHEJ are SCR7, STL127685, which is a 4-fluorophenyl analog of the Ku70/80 inhibitor STL127705 (Weterings et al. 2016), and DNA-PK inhibitor NU7026 (Suzuki et al. 2016). To block Alt-NHEJ we chose WRN helicase inhibitor NSC 19630 (Aggarwal et al. 2011). The NEDD8 activating enzyme (NAE) inhibitor MLN4924 has been shown to inhibit the neddylation of CtIP, which is increasing the extend of DNA end resection at strand breaks, and therefore regulates DNA double strand break repair pathway choice to preferentially undergo HDR (Jimeno et al. 2015). DNA resection leaves ssDNA which is coated and stabilized by RPA, before undergoing homology search and recombination. We assumed increasing availability of RPA could favor HDR. Fumaropimaric acid (NSC15520) prevents the association of RPA to p53 and RAD9 (Glanzer et al. 2011) (Glanzer et al. 2013), possibly increasing the abundance of available RPA for ssDNA. RAD51 is critical for homologous recombination with double stranded DNA (dsDNA), while RAD52 is needed for annealing of ssDNA (Grimme at al. 2010). We therefore chose to test the effect of RAD52 inhibitor AICAR (Sullivan et al. 2016), RAD51 inhibitor B02 (Huang et al. 2011), and RAD51 enhancer RS-1 (Song et al. 2016) on precise genome editing efficiency. Furthermore, we included small molecules that have been described to enhance the repair protein kinase ATM. Resveratrol has been described to have a direct stimulatory effect on the catalytic efficiency of purified ATM in vitro (Lee et al. 2014). The histone deacetylase inhibitor Trichostatin A actives an ATM-dependent DNA damage signaling pathway and has been described to increase HR (Lee 2007)(Jimeno et al. 2015). Lastly, we included R3-adrenergic receptor agonist L755507 in the screen.

Results

Effect of Small Molecules on Precise Genome Editing

First we tested different concentrations of the small molecules to examine their influence on precise editing of CALD1, KATNA1 and SLITRK1 with iCRISPR Cas9D10A (FIG. 3). Consequently, we chose the respective concentration that gave the highest frequency of precise genome editing. When different concentrations had a similar effect on editing we chose the lower concentration. Effects of chosen small molecule concentrations on precise genome editing efficiency in CALD1, KATNA1 and SLITRK1 with Cas9D10A and Cas9 from repeated independent experiments are shown in FIG. 4.

Figure 4B:
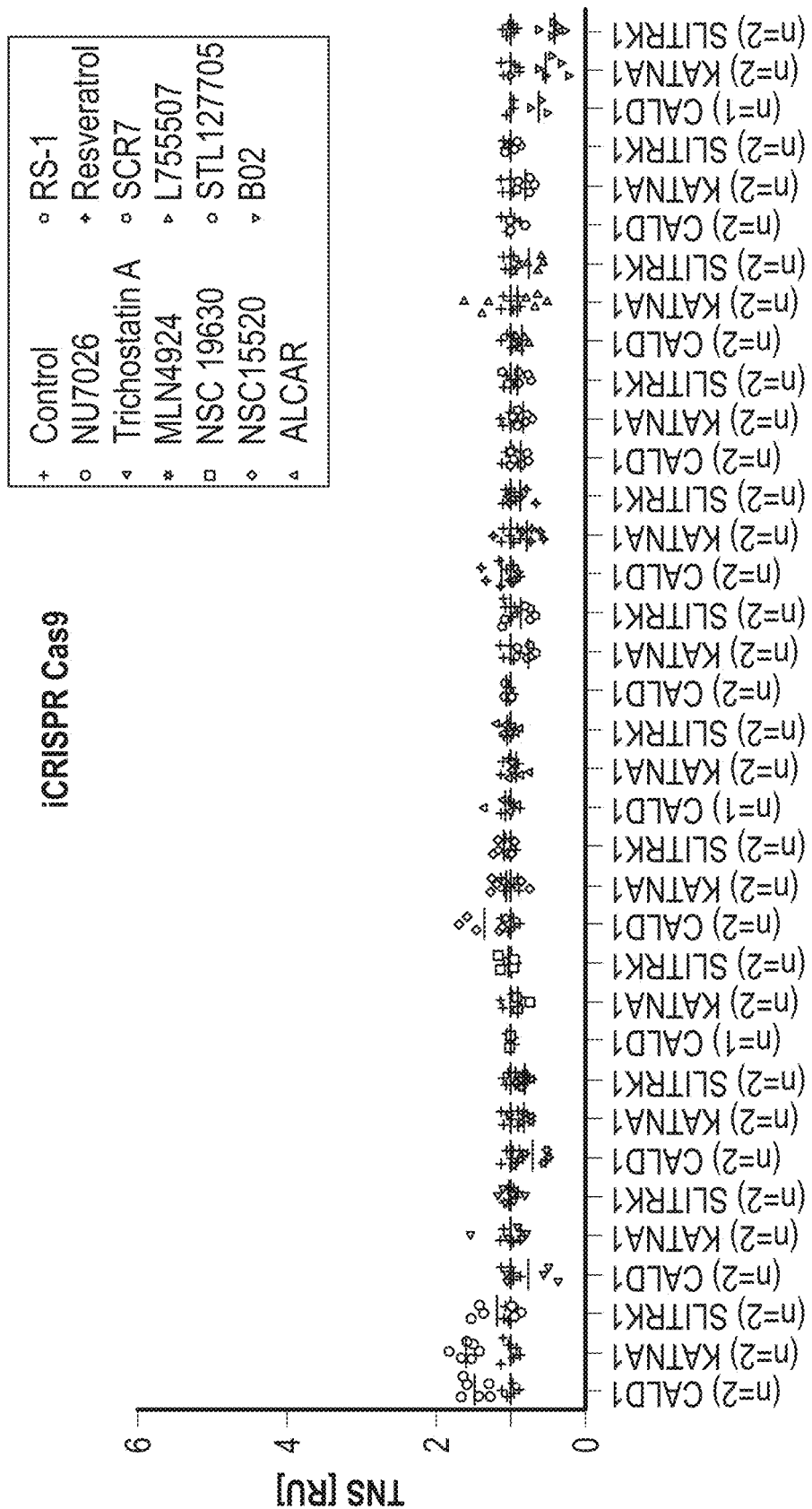

NU7026 treatment increased PGE for all three loci with Cas9D10A (FIG. 4A) and Cas9 (FIG. 4B). The mean change was 1.5-fold for CALD1, 2.6-fold for KATNA1 and 2.5-fold for SLITRK1 with Cas9D10A, and 1.5-fold for CALD1, 1.6-fold for KATNA1 and 1.2-fold for SLITRK1 with Cas9. In addition to NU7026, we found TSA and MLN4924 to have an enhancing effect on PGE frequency with Cas9D10A. TSA increased PGE 1.5-fold for CALD1, 2.2-fold for KATNA1 and 1.8-fold for SLITRK1 with Cas9D10A; interestingly no enhancing effect was found with Cas9. MLN4924 increased PGE 1.2-fold for CALD1, 1.1-fold for KATNA1 and 1.3-fold for SLITRK1 with Cas9D10A. With Cas9 there is a slight diminishing effect of MLN4924 on PGE. Treatment with NSC 15520 increased PGE of CALD1 with Cas9D10A and Cas9 1.4 fold and 1.3 fold, respectively. However, there was no effect on PGE of KATNA1 and SLITRK1. NSC 19630, AICAR, RS-1, Resveratrol, SCR7, L755507 and STL127685 showed no clear effect on PGE frequency over the three genes CALD1, KATNA1 and SLITRK1 compared to the respective controls with Cas9D10A and no effect or a diminishing effect with Cas9. B02 halved PGE in all three loci both with Cas9D10A and Cas9.

We next tested if combinations of small molecules would have an enhancing effect on PGE with Cas9D10A or Cas9. We chose small molecules that showed an increase in PGE with Cas9D10A in at least one gene and never a PGE decrease; those molecules are: NU7026, TSA, MLN4924, NSC 19630, NSC 15520, AICAR and RS-1.

Impact of small molecule combinations on editing of the tree different loci with either Cas9D10A or Cas9 are shown in FIG. 5. For editing with Cas9D10A treatment with NU7026 or PGE resulted in 2.3- or 1.8-fold higher PGE frequency than without the molecules (Tukey's pair-wise post-hoc comparisons: p<0.001) (FIG. 5A). A combination of both NU7026 and TSA resulted in 1.3 or 1.6 times higher PGE frequency than either NU7026 or TSA alone (p<0.001). Addition of MLN4924 to the mix of NU7026 and TSA lead to an additional 1.3-fold increase in PGE (p<0.01). Further addition of NSC 15520 slightly increased the mean of PGE for all loci when using Cas9D10A for editing, without reaching statistical significance. Addition of NSC 19630, AICAR and RS-1 had no measurable effect on PGE.

We conclude that the mix of small molecules that increases the frequency of PGE with Cas9D10A the most is a combination of NU7026 (20 µM), TSA (0.01 µM), MLN4924 (0.5 µM) and NSC 15520 (5 µM), which we name 'CRISPY' nickase mix. It yielded an increase of PGE of 2.8-fold (from 11 to 31%) for CALD1, 3.6-fold (from 12.8 to 45.8%) for KATNA1 and 6.7-fold (from 4.7 to 31.6%) for SLITRK1 in the iCRISPR 409-B2 iPSC line. When we used Cas9, which introduces blunt-ended DSBs, no significant effect was seen when adding other small molecules in addition to NU7026 (FIG. 5B). In contrast, the CRISPY mix together with Cpf1 ribonucleoprotein, which produces staggered DNA cuts, introduced by electroporation in 409-B2 hiPSCs increased PGE 2.9-fold for HPRT and 4.0-fold for DMNT1 (FIG. 5D). Addition of only NU7026 increased PGE 2.1-fold for HPRT and 2.4-fold for DMNT1.

To test if the CRISPY mix increases PGE in other pluripotent stem cell lines we edited the gene KATNA1 in SC102A1 hiPSCs and H9 hESCs using Cas9n plasmid electroporation, and HPRT in chimpanzee iPSCs using Cpf1 ribonucleoprotein. PGE increased 2.6-fold, 2.8-fold, and 2.3-fold, respectively, and the increase was bigger than when using NU7026 alone (FIG. 5C).

In a further experiment, the impact of the CRISPY mix and its components on targeted nucleotide substitution efficiency was tested in a plurality of non-pluripotent cell types including the immortalized human embryonic kidney cell line HEK293, the immortalized leukemic cell line K562, hematopoietic CD4$^+$ T cells and CD34$^+$ hematopoietic progenitor cells as well as primary human keratinocytes (HEKa) by electroporation of Cpf1. The results are shown in FIG. 6. It was found that the component NU7026 of the CRISPY mix is effective in the tested cell lines except in HEKa cells. In HEK293 and K562 cells, NU7026 strongly increases PGE efficiency, TSA and NSC15520 moderately increase efficiency, and MLN4924 has a clear disruptive effect in those cell lines with cancer characteristics. MLN4924 has a disruptive effect on PGE efficiency in primary cells as well. The CRISPY mix without MLN4924 has a higher effect on PGE efficiency than NU7026 alone in hematopoietic CD4$^+$ T and CD34$^+$ progenitor cells. In primary human keratinocytes (HEKa) also NU7026 and NSC15520 have a disruptive effect on PGE efficiency.

In a still further experiment, the toxicity of the CRISPY mix and its components was tested. After KATNA1 editing with Cas9n double nicking and CRISPY mix treatment for 24 h cells showed a viability of 75% compared to no small molecule treatment, with no additive toxic effect of its components (FIG. 7). Importantly, when we simulated five rounds of editing, each round consisting of passaging cells with the lipofection reagent and CRISPY mix followed with 3 days of recovery, the cells had a healthy karyotype with no numerical or large scale chromosomal aberrations as shown by trypsin-induced Giemsa staining (FIG. 13).

Figures 8B, 8C:
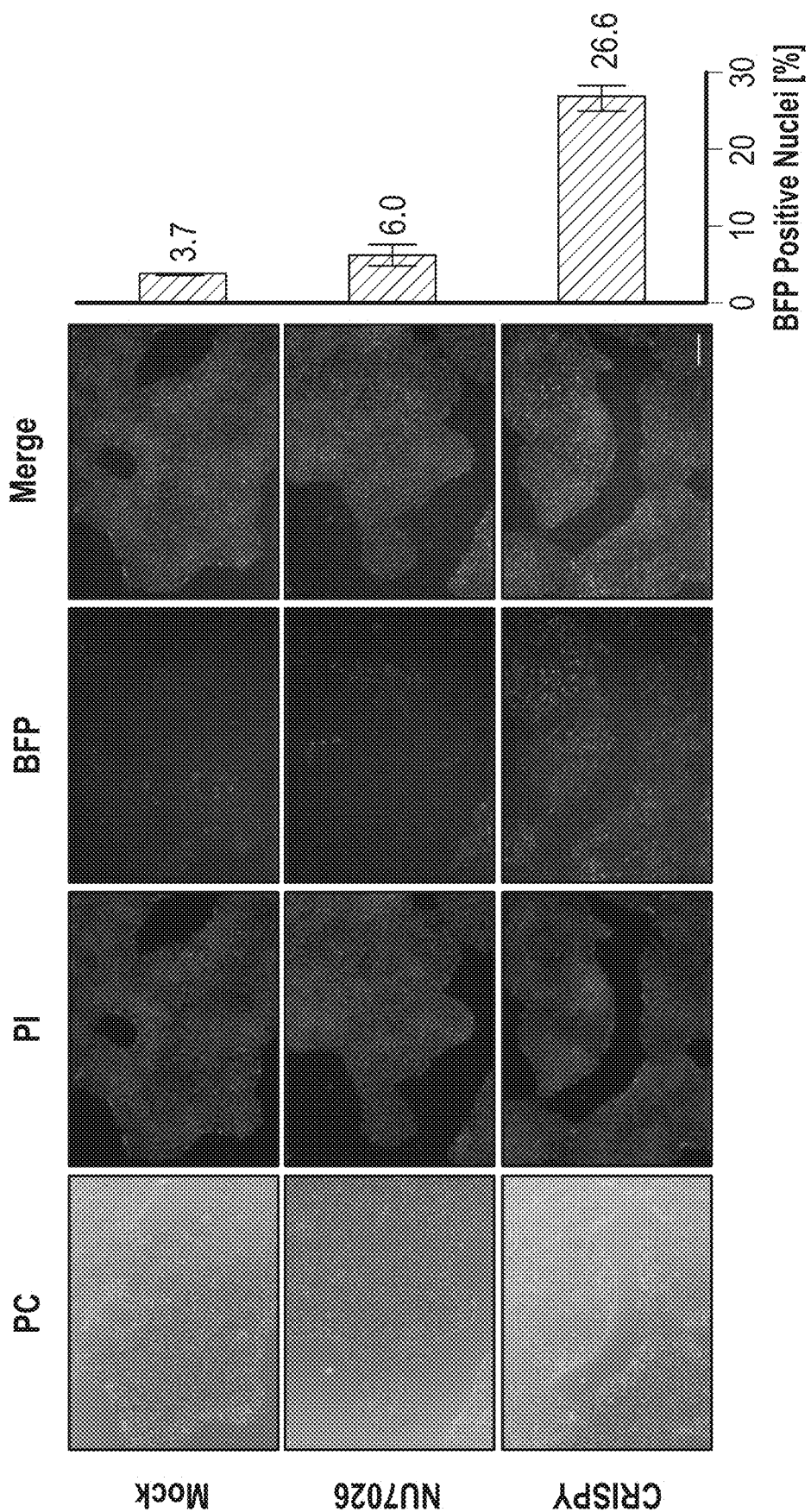

In a still further experiment, the impact of the CRISPY mix and its component NU7026 on BFP insertion (ssODN) efficiency in human induced pluripotent stem cells was tested. The results are shown in FIG. 8. We inserted a 871 nt (including 50 nt homology arms) sequence encoding a 2A-self cleaving peptide in front of an enhanced blue fluorescent protein (BFP)(Subach et al. 2011) in the AAVS1 iCRISPR locus. If the sequence is inserted, doxycycline will lead to expression of nucleus-imported BFP. Nuclei positive for BFP increased 7.1-fold (26.6%) compared to the no-CRISPY control (3.7%), while NU7026 alone lead to an increase of 1.6 fold (6%) (FIGS. 8B and C) showing that the CRISPY mix increases efficiency of insertion of a gene fragment in iPSCs.

Effects of Formulated DNA Protein Kinase Catalytic Subunit on Precise Genome Editing Mutation of K3753R near the ATP binding site abolishes the kinase activity of DNA-PKcs. In CHOV3 cells, DSB induced HDR in DNA-PKcs KR cells has been shown to be 2- to 3-fold above the elevated HDR level of DNA-PKcs null cells, and ~4- to 7-fold above cells expressing wildtype DNA-PKcs (Shrivastav et al. 2008 and 2009).

Figures 10A, 10B:
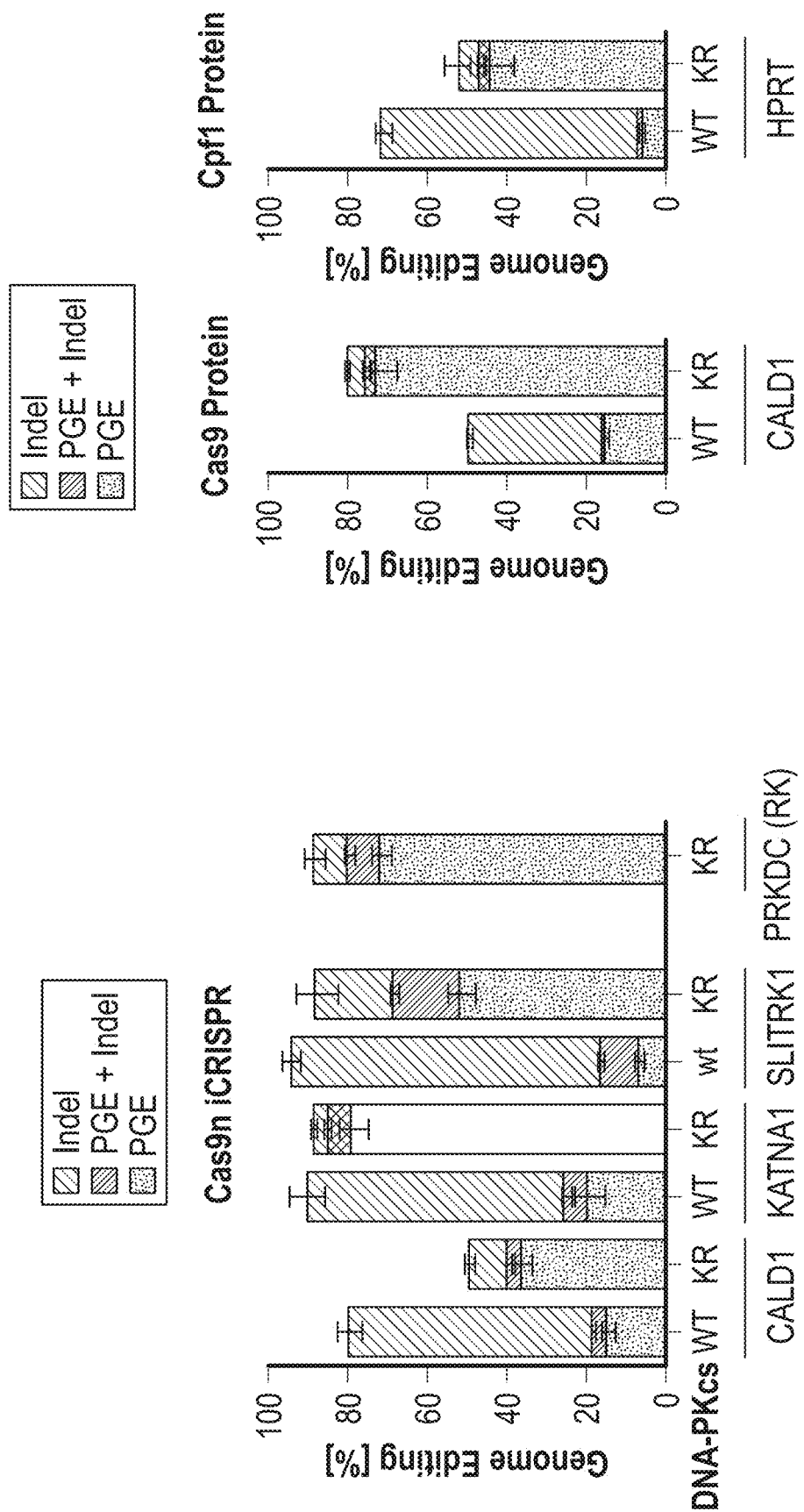

We generated an induced pluripotent stem (iPSC) line with a doxycycline inducible Cas9 nickase (iCRISPR-D10A) as described by Gonzalez et al. (2014), to achieve high efficiency of targeted DSBs with reduced off-targets (Shen et al. 2014). Using the integrated Cas9D10A, we exchanged lysine to arginine near the kinase active site of DNA-PKcs (K3752R) to inactive its kinase activity (Shrivastav et al. 2008 and 2009), while keeping the overall structure intact. To compare the efficiency of precise genome editing of using wildtype DNA-PKcs to DNA-PKcs KR, we chose to precisely edit neurite outgrowth genes CALD1, KATNA1 and SLITRK1 back to the ancestral state of the last common ancestor of human and neandertal (Prufer et al. 2014). We also explored the efficiency of reverse inactivation of PRKDC (DNA-PKcs) by exchanging R3753 back to lysine. PGE efficiencies of CALD1, KATNA1, SLITRK1 and PRKDC with iCRISPR-Cas9D10A expressing either wildtype DNA-PKcs or DNA-PKcs KR are shown in FIG. 10A. When using DNA-PKcs KR, the PGE efficiencies increase 2.5-fold (36%), 4.1-fold (78.5%), and 7.8-fold (51.1%) for CALD1, KATNA1 and SLITRK1. This corresponds to a shift of the ratio of PGE/NHEJ from 0.23, 0.29 and 0.08 to 3.49, 25.45, and 2.60, respectively. We achieve back-mutation of PRKDC in 71.4% of chromosomes. When electroporating recombinant Cas9 or Cpf1, the PGE efficiency for CALD1 or HPRT increased 4.8 fold (72.2%) or 8.3 fold (43.7%) with a shift of the ratio of PGE/NHEJ from 0.45 to 12.8 or 0.08 to 7.1. Therefore, PGE is increased by the KR line regardless of the type of DSB.

Figure 3B:
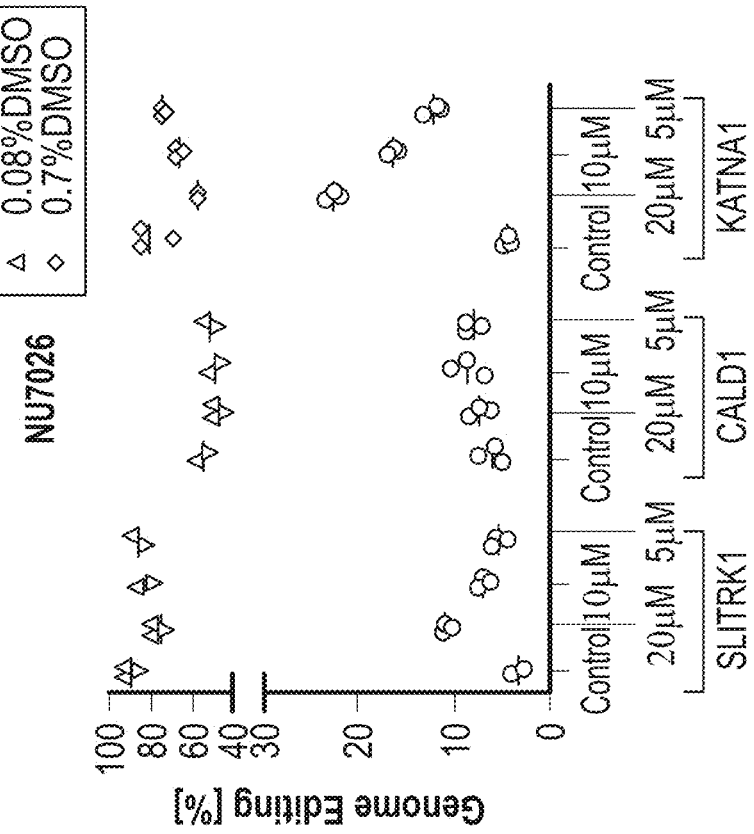
Figure 3A:
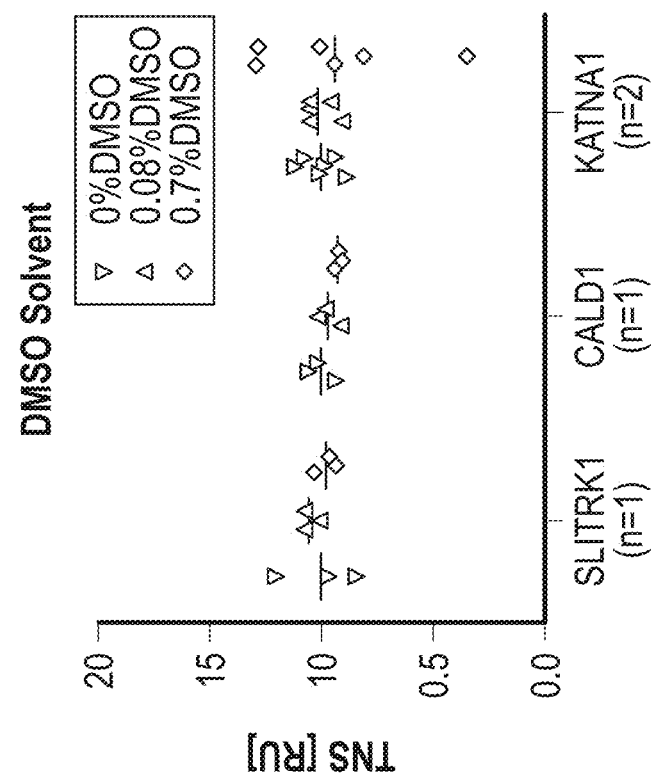
Figure 3D:
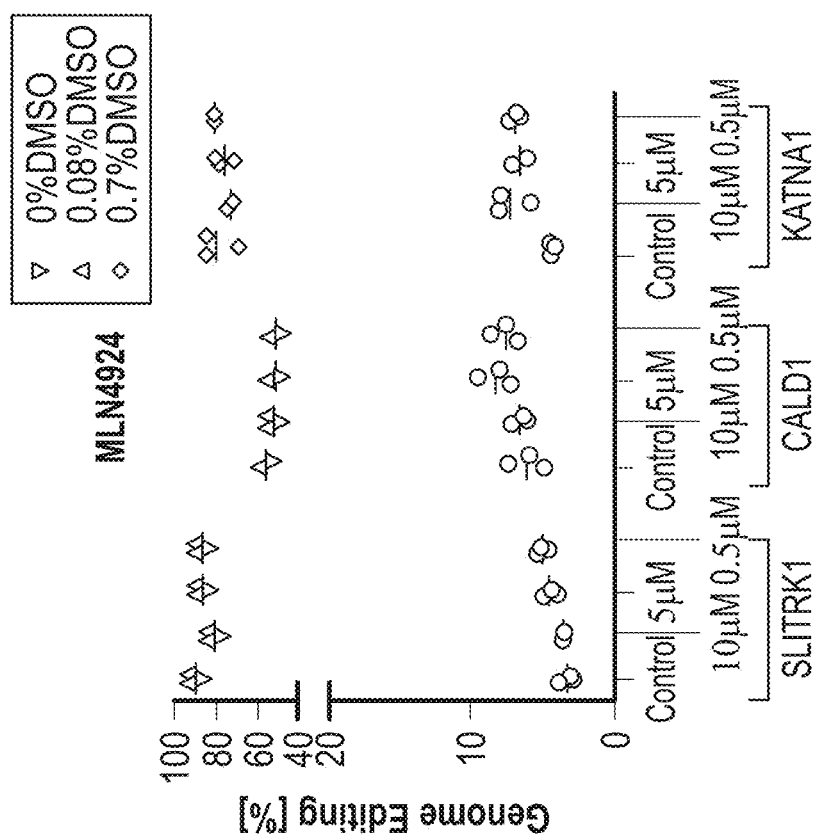
Figure 3C:
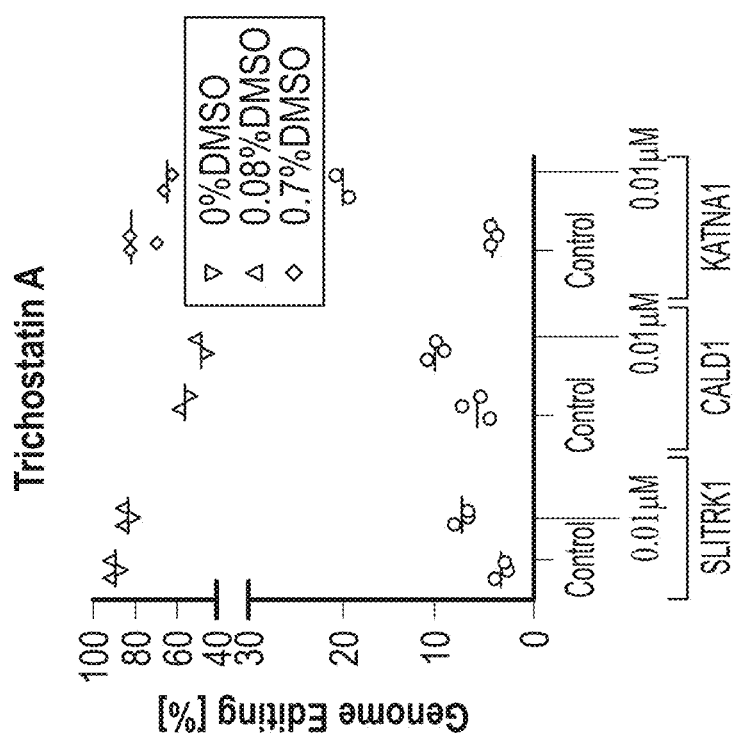
Figures 3E, 3F:
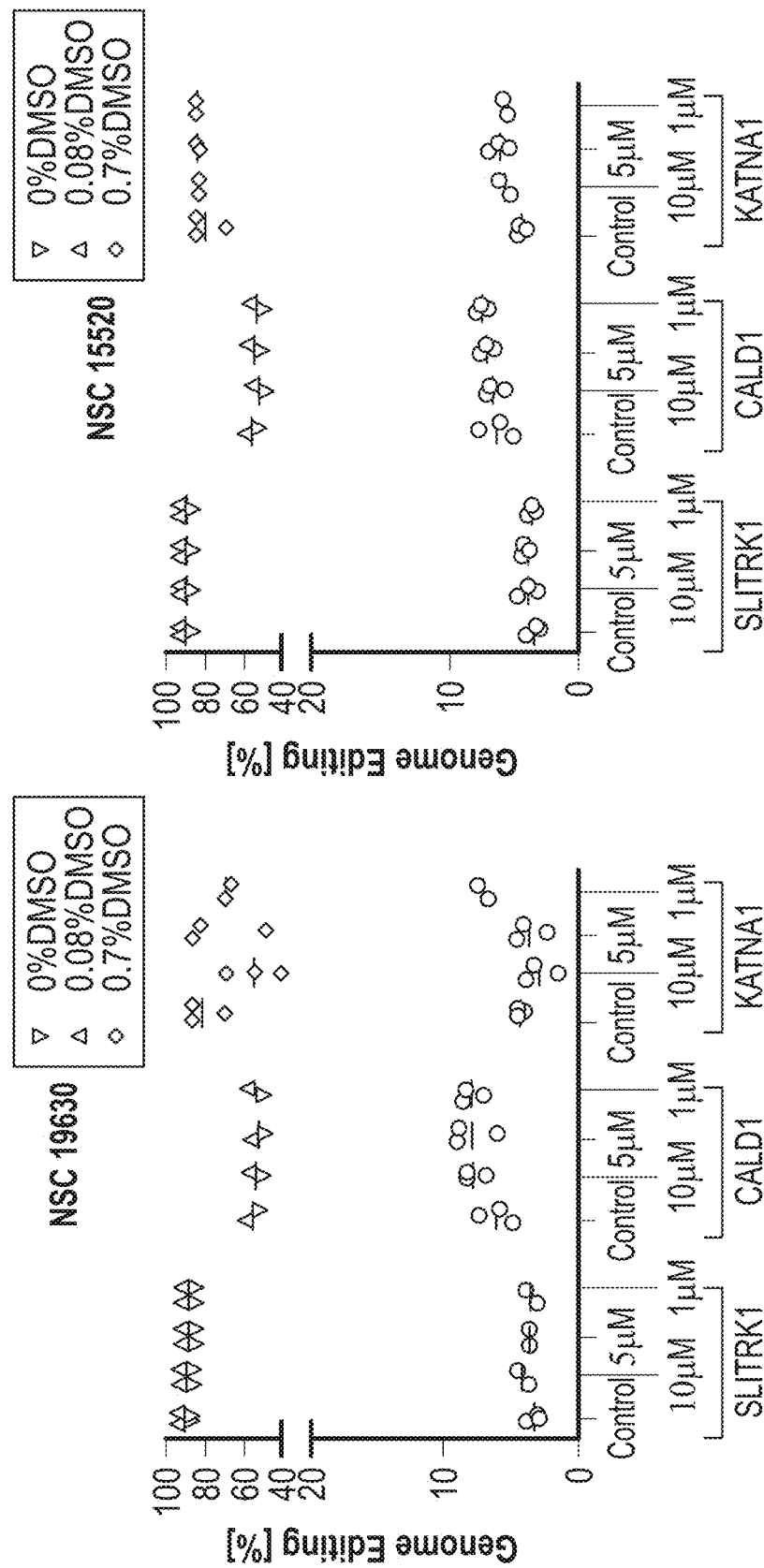
Figures 3I, 3J:
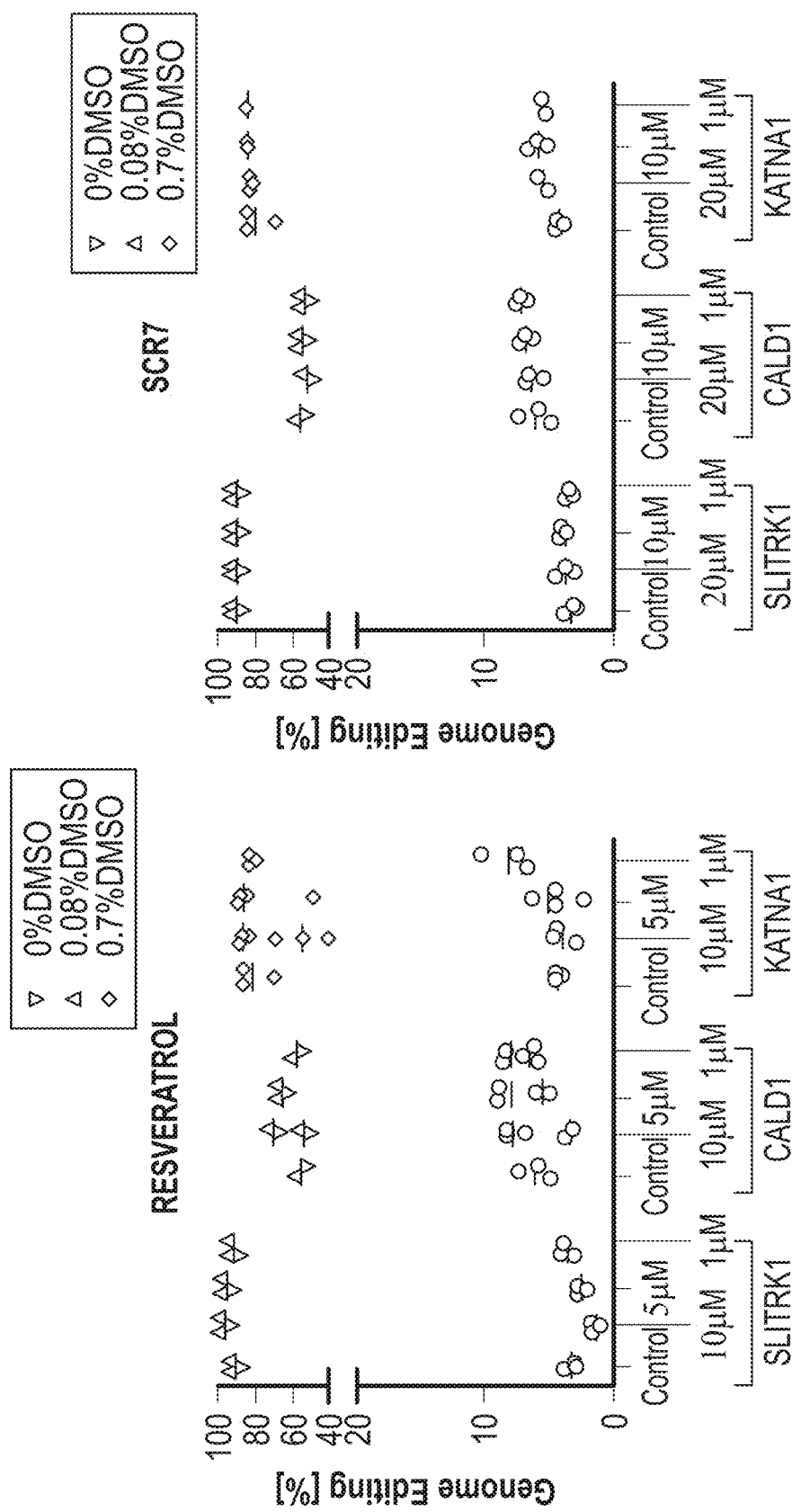
Figures 3K, 3L:
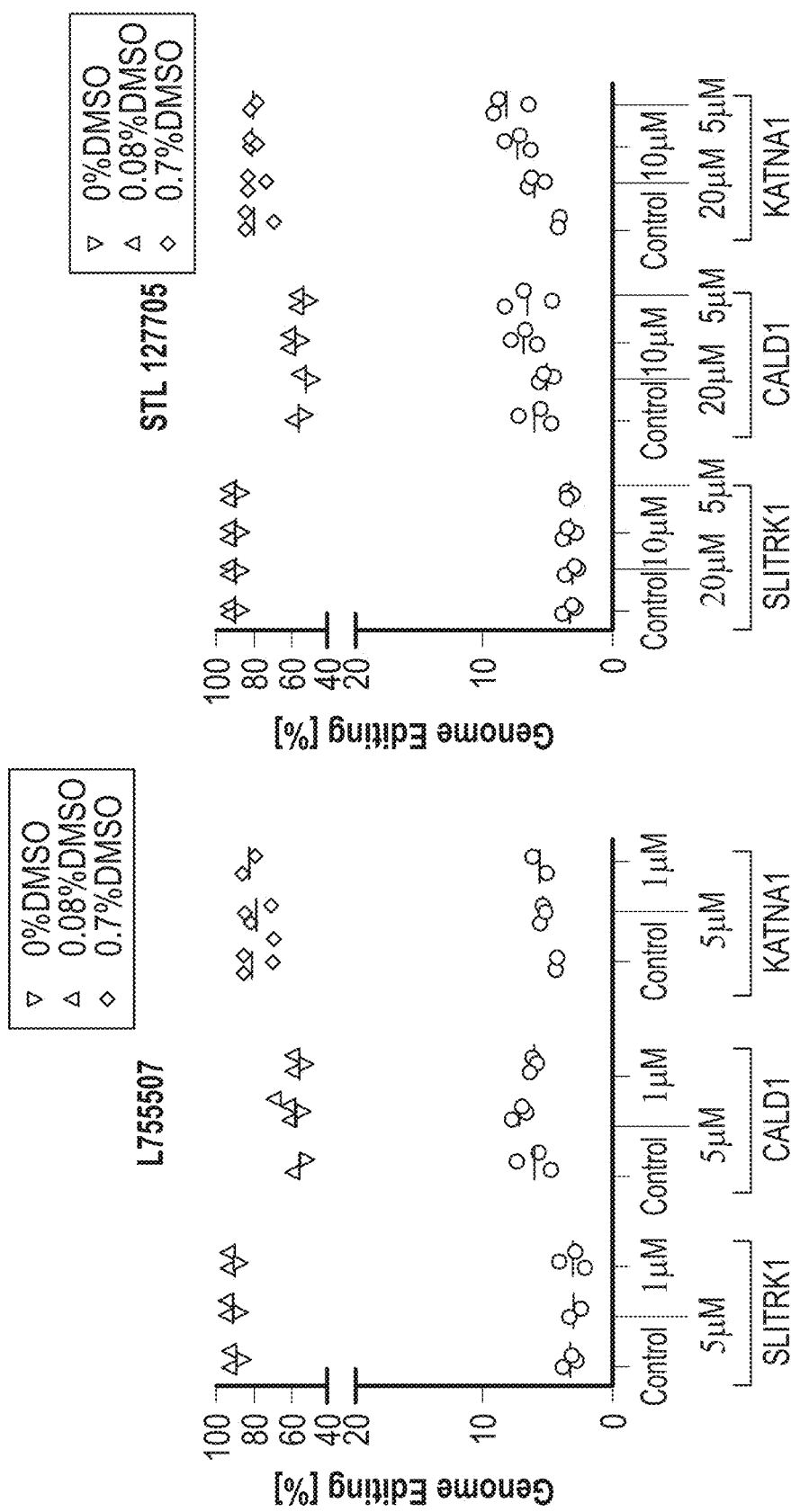
Figure 11B:
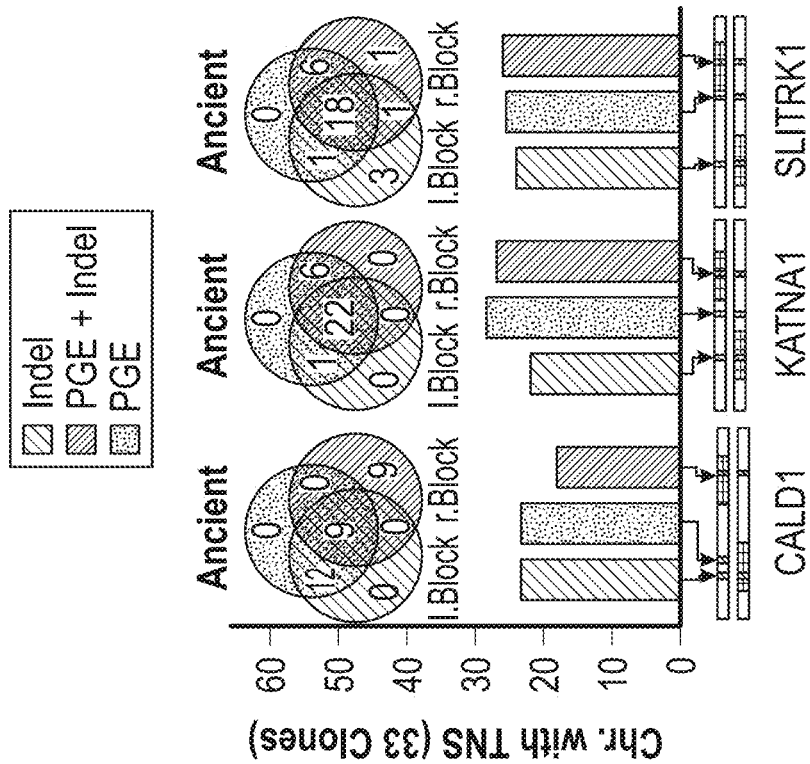
Figure 11A:
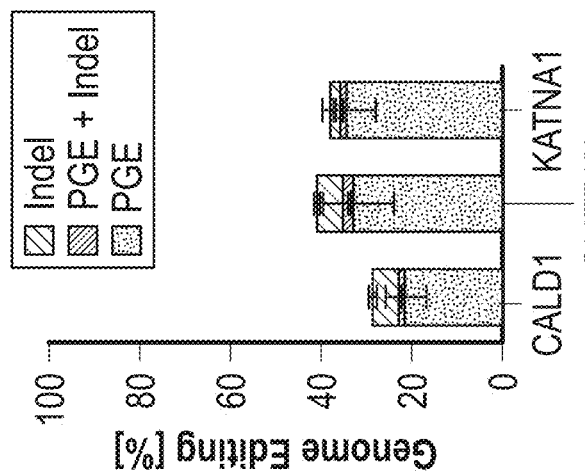

Given these high PGE efficiencies with DNA-PKcs KR, we next tried to multiplex editing of the three genes. We achieved PGE efficiencies of 3-10% for a gene at best, when using multiplexed lipofection of gRNAs and ssDNA donors (data not shown). When electroporating gRNAs and ssODN of the three genes, we achieved PGE efficiencies of 21.3% for CALD1, 32.0% for KATNA1, and 34.0% for SLITRK1 (FIG. 11A). Contrary to lipofection, cells are prepared as single cell suspension for electroporation. While the majority of cells was plated for following bulk DNA isolation, ten percent were plated as single cell dilution that will give rise to colonies descendent from one cell. The analysis of 33 clones showed that the ancient mutations and silent blocking mutations are not always incorporated together in chromosomes where Targeted Nucleotide Substitution (TNS) took place (FIG. 11B). FIG. 11C shows a heatmap of chromosomes with incorporation of indels and incorporation of any TNS, regardless if blocking mutation or ancient mutation (left panel), or of incorporation of at least the ancient mutation (right panel). Most clones either remain wildtype or are precisely edited for all three genes. Strikingly, one third of clones has a TNS without any additional indel on both chromosomes for all three genes. 12.1% of clones have at least the ancient TNS without any additional indel on both chromosomes for all three genes. The drop of 33.3% to 12.1% is mostly due to the design of the CALD1 donor, were the right blocking mutation is far away from the other two mutations, and it is the only incorporated substitution in 30% of CALD1 TNS positive chromosomes (9 out of 30)(FIG. 3A). The incorporation of TNS on both chromosomes of 3 genes is more than 4-fold higher than expected by chance, based on single gene TNS efficiencies (7.1% expected for any TNS and 2.9% expected for at least ancient TNS). The herein presented MPGE is not only efficient but also fast. Using single cell dilution seeding directly after electroporation allows generating clones with desired MPGE in less than two weeks (FIG. 11D). Importantly, DNA-PKcs KR hiPSCs maintained a healthy karyotype with no numerical or large scale chromosomal aberrations after 26 passages (corresponding to 3 months), as shown by trypsin induced giemsa banding (FIG. 13).

The PGE efficiency in the presence of the mutated DNA-PKcs may be further enhanced by the CRISPY mix with Cas9D10A as we show in a further experiment. The DNA-PKcs mutant had a 2.8-fold, 4,3-fold and 12.4-fold increase of PGE for CALD1, KATNA1 and SLITRK1, respectively (see FIG. 12). In addition with the CRISPY mix the efficiency of PGE compared to the DNA-PKcs wildtype without small molecule treatment was increased even further. The PGE efficiency was 48% (3.7-fold increase), 82% (4.7-fold increase) and 57.5% (19.2-fold increase) for CALD1, KATNA1 and SLITRK1, respectively.

Discussion

While the CRISPY mix increases PGE more than any individual component it is comprised of in all four pluripotent stem cell lines tested (three human and one chimpanzee) (FIGS. 5A, C, and D), this is not the case for other cell lines tested (FIG. 6). In fact, our results show that small molecules and their combinations can have opposite effects on PGE in different cell lines. This could be due to that cell lines rely on different repair proteins or repair pathways and suggests that follow-up studies on cell type-specific mechanisms of DNA repair are warranted. In line with this interpretation are studies that show that human ESCs and iPSCs possess very high DNA repair capacity that decreases after differentiation (Blanpain et al. 2011, Rocha et al. 2013). It may also explain some of the inconsistencies between studies, e.g. the DNA ligase IV inhibitor SCR7 and RAD51 enhancer RS-1 increase precise genome editing in some cell types but not in others. Thus, it may be necessary to screen small molecules for their effects on CRISPR editing in each cell type of interest.

Small molecules that increased PGE in pluripotent stem cells with Cas9D10A and ssODN donor both alone (FIG. 4A) and in a mix (FIG. 5A) are NU7026, TSA, MLN4924 and NSC 15520. The mix also shows an additional increasing effect on PGE with Cpf1 but not with Cas9 compared to single treatment with NU7026. NU7026 inhibits DNA-PK, a major complex in NHEJ pathway (Shrivastav et al. 2008) and has been previously shown to increase PGE efficiency in hiPSCs (Suzuki et al. 2016). TSA can activate an ATM-dependent DNA damage signaling pathway (Lee 2007). The Nedd8 activating enzyme (NAE) inhibitor MLN4924 has been shown to inhibit the neddylation of CtIP which is increasing the extent of DNA end resection at strand breaks thereby promoting HDR (Jimeno et al. 2015). DNA resection leaves ssDNA which is coated and stabilized by RPA before undergoing homology search and recombination. NSC15520 prevents the association of RPA to p53 and RAD9 (Glanzer et al. 2011)(Glanzer et al. 2013), possibly increasing the abundance of available RPA for ssDNA which could favor HDR. RS-1, SCR7 and L755507 for which there are conflicting reports on their capacity to increase PGE showed no clear effect in our hands on PGE neither with Cas9 nor with Cas9D10A.

The enhancing effect of TSA and MLN4924 on PGE when used with Cas9D10A double nicking or Cpf1 contrary to no effect visible with Cas9 suggests that blunt and staggered DNA cuts (5' overhangs) are repaired by different repair mechanisms. To date the mechanism of HDR with ssODN is not clear but models have been proposed (Bothmer et al. 2017). Bothmer et al. find that 5' overhang structures yield higher levels of HDR than 3' overhangs and suggest that different overhang polarities engage different repair pathways.

However, the negative effect of MLN4924 with Cas9 editing might be due to shorter ssODN used compared to longer Cas9D10A ssODN. If extensive DNA resection triggered by MLN4924 takes place, there are is no homology left for ssODN annealing if short donors are used. Since long 5' overhangs are present in Cas9D10A editing, homologous DNA is provided, even after extensive resection. Therefore, usage of longer donors might render MLN4924 effective in enhancing precise genome editing also when using Cas9.

While RAD51 is obviously important for classical homologous recombination with dsDNA (Shrivastav et al. 2008) we wanted to examine if RAD52, rather than RAD51, could be the driving force behind HDR of ssODN since RAD52 is needed for annealing of ssDNA (Grimme et al. 2010). Our results of the effect of RAD52 inhibitor AICAR, RAD51 inhibitor B02, and RAD51 enhancer RS-1 on PGE efficiency suggests that RAD51 and not RAD52 is important for precise editing with ssODN, since inhibition of RAD51 by B02 halved and inhibition of RAD52 had no effect on PGE efficiency. Interestingly, stimulation of RAD51 with RS-1 had no beneficial effect on PGE.

To increase PGE efficiency we produced an inducible Cas9D10A iPSC line and optimized the delivery of ssODNs such that sometimes indels in more than 90% of the cells are observed (FIG. 3A). Using the CRISPY small molecule mix we achieve almost 50% PGE in hiPSCs (FIG. 3A), the highest PGE efficiency of human pluripotent stem cells described to date to our knowledge. Furthermore, we are the first to show efficient PGE by using Cpf1 (20%) with help of the CRISPY mix (FIG. 5C). The CRISPY mix provides an easy tool for increasing PGE frequency and could therefore be useful for many researchers or medical professionals using the CRISPR system to perform precise genome editing.

By harnessing efficient DSB induction using iCRISPR and utilizing kinase dead DNA-PKcs KR, as a switch between NHEJ and HDR, highly efficient precise editing of the genome is possible (FIG. 10). High PGE efficiency goes in hand with a high ratio of PGE to indels. We also show that the incorporation of TNS in all the targeted chromosomes is much higher than expected by chance, based on single gene TNS efficiencies, when multiplexing several genes. The HDR inhibiting properties of DNA-PKcs have been shown to be absolutely dependent on its kinase activity (Neal et al. 2011). Similar to our data, HDR in CHOV3 KR cells has been shown to be 4- to 7-fold above cells expressing wildtype DNA-PKcs (Shrivastav et al. 2008 and 2009). Surprisingly, the increase in HDR in CHOV3 KR cells was higher than in CHOV3 DNA-Pkcs knockout cell, suggesting that the protein structure is needed for further enhanced HDR. Phosphorylation of its ABCDE or JK cluster been shown to promote end processing, or inhibit NHEJ, respectively (see FIG. 9B). DNA-PKcs deficiency results in reduced levels of the important repair kinase ATM in cultured cell lines and mice (10). Shrivastav et al. argue that restored ATM-dependent phosphorylation of DNA-PKcs KR, and possibly ATM promoted RAD51 turnover, contributes to the hyperrecombination phenotype (Neal et al., 2016). By using catalytically inactive but structurally intact DNA-PKcs, phosphorylation of downstream c-NHEJ proteins is blocked, as well as phosphorylation induced inhibition of ATM kinase activity (Zhou et al., 2017), while ATM levels are maintained in a kinase independent manner, therefore leading to enhanced HDR. Given the central role of DNA-PKcs in c-NHEJ and the similar findings on HDR increase by Shrivastav et al. in Chinese Hamster Ovary cells, we suspect the KR mutation will have a consistent effect across cell types and species. As DNA-PKcs, and its sequence around K3753, is conserved in vertebrates (FIG. 9C), the KR mutation could be a valuable gene modification tool in several animal models. DNA-PKcs orthologues have also been found in mosquito, honey bee, and the amoeba slime mold suggesting ancient ancestry of this enzyme (Dore et al. 2004, Douglas et al. 2007.

We did not detect any numerical or large scale chromosomal aberrations after 3 months of culturing DNA-PKcs KR hiPSCs (FIG. 13). Besides targeted genome cleavage, endogenous DSBs regularly occur because of reactive oxygen species and physical stress leading to replication fork collapse, as well as during V(D)J recombination. Impairment of error-prone c-NHEJ by inactivating the kinase activity of DNA-PKcs, leaves the cells to repair a DSB with faithful and enhanced HDR utilizing the sister chromatid, with slow error-prone a-NHEJ, or death. Speculatively, genomic stability could therefore by even better in KR cells compared to wildtype because of high fidelity repair by HDR, with the cost of loss in heterozygosity.

We also showed efficient reverse inactivation of DNA-PKcs by mutating R3753 back to lysine (FIG. 10A). Reactivating DNA-PKcs after implementing targeted mutations is desirable before cell differentiation into T cells, as V(D)J recombination depends on c-NHEJ. Back-mutating DNA-PKcs KR before cell differentiation into non-proliferating cells like neurons might be beneficial as well. HDR is restricted to dividing cells and therefore NHEJ is central to DNA repair in post-mitotic cells. However, the c-NHEJ factors Ku70/80, XRCC4, and LIG4 together with XLF are sufficient to repair low levels of damage (Gu et al., 2000), and a-NHEJ is anyway independent of DNA-PKcs.

The use of the CRISPY small molecule mix together with catalytically inactive DNA-PKcs, this finding has the potential to revolutionize CRISPR assisted research and tailored genomes, since editing of multiple loci at once is possible. Not only is the editing efficiency very high (up to 82%)—the limited proportion of indels now allows fast (multiplexed) precise genome editing (FIGS. 10 and 11).

To conclude, the hyperrecombining effect of DNA-PKcs KR in combination with the CRISPR technology leads to unforeseen efficiencies in precise genome editing, which can be further increased by the CRISPY small molecule mix in human pluripotent stem cells. This could substantially reduce time and labor in various areas of genome research. These include exciting applications like high-throughput Genome-Wide-Association-Screen (GWAS) validation of relevant medically important traits, disease modelling and drug screens, species comparative analysis, ex-vivo gene-therapy, simplified production of tailor-made animal models, species de-extinction, and someday possibly implementation of de-novo synthesized large genome fragments.

REFERENCES

1. Aggarwal, M., Sommers, J. A., Shoemaker, R. H. & Brosh, R. M., Jr. Inhibition of helicase activity by a small 1. molecule impairs Werner syndrome helicase (WRN) function in the cellular response to DNA damage or replication stress. *Proc Natl Acad Sci USA* 108, 1525-1530 (2011).
2. Blanpain, C., Mohrin, M., Sotiropoulou, P. A. & Passegue, E. DNA-damage response in tissue-specific and cancer stem cells. *Cell Stem Cell* 8, 16-29 (2011).
3. Chari, R., Mali, P., Moosburner, M. & Church, G. M. Unraveling CRISPR-Cas9 genome engineering parameters via a library-on-library approach. *Nat Methods* 12, 823-826 (2015).
4. Chu, V. T. et al. Increasing the efficiency of homology-directed repair for CRISPR-Cas9-induced precise gene editing in mammalian cells. *Nat Biotechnol* 33, 543-548 (2015).
5. Dore, A. S., Drake, A. C., Brewerton, S. C. & Blundell, T. L. Identification of DNA-PK in the arthropods. Evidence for the ancient ancestry of vertebrate non-homologous end-joining. *DNA Repair (Amst)* 3, 33-41 (2004).
6. Douglas, P. et al. The DNA-dependent protein kinase catalytic subunit is phosphorylated in vivo on threonine 3950, a highly conserved amino acid in the protein kinase domain. *Mol Cell Biol* 27, 1581-1591 (2007).
7. Field, A. Discovering Statistics using SPSS. (Sage Publications, London; 2005).
8. Fu, Y. et al. High-frequency off-target mutagenesis induced by CRISPR-Cas nucleases in human cells. *Nat Biotechnol* 31, 822-826 (2013).
9. G., D. R. I. Alternative pathways of non-homologous end joining (NHEJ) in genomic instability and cancer. *Transl Cancer Res* 2 (2013).
10. Glanzer, J. G. et al. A small molecule directly inhibits the p53 transactivation domain from binding to replication protein A. *Nucleic Acids Res* 41, 2047-2059 (2013).
11. Glanzer, J. G., Liu, S. & Oakley, G. G. Small molecule inhibitor of the RPA70 N-terminal protein interaction domain discovered using in silico and in vitro methods. *Bioorg Med Chem* 19, 2589-2595 (2011).
12. Gonzalez, F. et al. An iCRISPR platform for rapid, multiplexable, and inducible genome editing in human pluripotent stem cells. *Cell Stem Cell* 15, 215-226 (2014).
13. Greco, G. E. et al. SCR7 is neither a selective nor a potent inhibitor of human DNA ligase IV. *DNA Repair (Amst)* 43, 18-23 (2016).
14. Grimme, J. M. et al. Human Rad52 binds and wraps single-stranded DNA and mediates annealing via two hRad52-ssDNA complexes. *Nucleic Acids Res* 38, 2917-2930 (2010).
15. Gu, Y. et al. Defective embryonic neurogenesis in Ku-deficient but not DNA-dependent protein kinase catalytic subunit-deficient mice. *Proc Natl Acad Sci USA* 97, 2668-2673 (2000).
16. Huang, F. et al. Identification of specific inhibitors of human RAD51 recombinase using high-throughput screening. *ACS Chem Biol* 6, 628-635 (2011).
17. Jimeno, S. et al. Neddylation inhibits CtIP-mediated resection and regulates DNA double strand break repair pathway choice. *Nucleic Acids Res* 43, 987-999 (2015).
18. Kent, W. J. et al. The human genome browser at UCSC. *Genome Res* 12, 996-1006 (2002).
19. Kim, D. et al. Genome-wide analysis reveals specificities of Cpf1 endonucleases in human cells. *Nat Biotechnol* 34, 863-868 (2016).
20. Kircher, M., Sawyer, S. & Meyer, M. Double indexing overcomes inaccuracies in multiplex sequencing on the Illumina platform. *Nucleic Acids Res* 40, e3 (2012).
21. Kleinstiver, B. P. et al. Genome-wide specificities of CRISPR-Cas Cpf1 nucleases in human cells. *Nat Biotechnol* 34, 869-874 (2016).
22. Lee, J. H., Guo, Z., Myler, L. R., Zheng, S. & Paull, T. T. Direct activation of ATM by resveratrol under oxidizing conditions. *PLoS One* 9, e97969 (2014).
23. Lee, J. S. Activation of ATM-dependent DNA damage signal pathway by a histone deacetylase inhibitor, trichostatin A. *Cancer Res Treat* 39, 125-130 (2007).
24. Lin, S., Staahl, B. T., Alla, R. K. & Doudna, J. A. Enhanced homology-directed human genome engineering by controlled timing of CRISPR/Cas9 delivery. *Elife* 3, e04766 (2014).
25. Maruyama, T. et al. Increasing the efficiency of precise genome editing with CRISPR-Cas9 by inhibition of non-homologous end joining. *Nat Biotechnol* 33, 538-542 (2015).
26. Meyer, M. & Kircher, M. Illumina sequencing library preparation for highly multiplexed target capture and sequencing. *Cold Spring Harb Protoc* 2010, pdb prot5448 (2010).
27. Milanowska, K. et al. REPAIRtoire—a database of DNA repair pathways. *Nucleic Acids Res* 39, D788-792 (2011).
28. Neal, J. A. et al. Inhibition of homologous recombination by DNA-dependent protein kinase requires kinase activity, is titratable, and is modulated by autophosphorylation. *Mol Cell Biol* 31, 1719-1733 (2011).
29. Neal, J. A. et al. Unraveling the complexities of DNA-dependent protein kinase autophosphorylation. *Mol Cell Biol* 34, 2162-2175 (2014).
30. Neal, J. A., Xu, Y., Abe, M., Hendrickson, E. & Meek, K. Restoration of ATM Expression in DNA-PKcs-Deficient Cells Inhibits Signal End Joining. *J Immunol* 196, 3032-3042 (2016).
31. Nussenzweig, A. & Nussenzweig, M. C. A backup DNA repair pathway moves to the forefront. *Cell* 131, 223-225 (2007).
32. O'Brien, J., Wilson, I., Orton, T. & Pognan, F. Investigation of the Alamar Blue (resazurin) fluorescent dye for the assessment of mammalian cell cytotoxicity. *Eur J Biochem* 267, 5421-5426 (2000).
33. Pinder, J., Salsman, J. & Dellaire, G. Nuclear domain 'knock-in' screen for the evaluation and identification of small molecule enhancers of CRISPR-based genome editing. *Nucleic Acids Res* 43, 9379-9392 (2015).
34. Pinello, L. et al. Analyzing CRISPR genome-editing experiments with CRISPResso. *Nat Biotechnol* 34, 695-697 (2016).
35. Prufer, K. et al. The complete genome sequence of a Neanderthal from the Altai Mountains. *Nature* 505, 43-49 (2014).
36. Quinn, G. P. K., M. J. Experimental Designs and Data Analysis for Biologists. (Cambridge University Press, Cambridge; 2002).
37. Renaud, G., Stenzel, U. & Kelso, J. leeHom: adaptor trimming and merging for Illumina sequencing reads. *Nucleic Acids Res* 42, e141 (2014).
38. Robert, F., Barbeau, M., Ethier, S., Dostie, J. & Pelletier, J. Pharmacological inhibition of DNA-PK stimulates Cas9-mediated genome editing. *Genome Med* 7, 93 (2015).
39. Rocha, C. R., Lerner, L. K., Okamoto, O. K., Marchetto, M. C. & Menck, C. F. The role of DNA repair in the pluripotency and differentiation of human stem cells. *Mutat Res* 752, 25-35 (2013).

40. Shen, B. et al. Efficient genome modification by CRISPR-Cas9 nickase with minimal off-target effects. *Nat Methods* 11, 399-402 (2014).
41. Shrivastav, M., De Haro, L. P. & Nickoloff, J. A. Regulation of DNA double-strand break repair pathway choice. *Cell Res* 18, 134-147 (2008).
42. Shrivastav, M. et al. DNA-PKcs and ATM co-regulate DNA double-strand break repair. *DNA Repair (Amst)* 8, 920-929 (2009).
43. Song, J. et al. RS-1 enhances CRISPR/Cas9- and TALEN-mediated knock-in efficiency. *Nat Commun* 7, 10548 (2016).
44. Subach, O. M., Cranfill, P. J., Davidson, M. W. & Verkhusha, V. V. An enhanced monomeric blue fluorescent protein with the high chemical stability of the chromophore. *PLoS One* 6, e28674 (2011).
45. Sullivan, K. et al. Identification of a Small Molecule Inhibitor of RAD52 by Structure-Based Selection. *PLoS One* 11, e0147230 (2016).
46. Suzuki, K. et al. In vivo genome editing via CRISPR/Cas9 mediated homology-independent targeted integration. *Nature* 540, 144-149 (2016).
47. Wang, K. et al. Efficient Generation of Orthologous Point Mutations in Pigs via CRISPR-assisted ssODN-mediated Homology-directed Repair. *Mol Ther Nucleic Acids* 5, e396 (2016).
48. Weterings, E. et al. A novel small molecule inhibitor of the DNA repair protein Ku70/80. *DNA Repair (Amst)* 43, 98-106 (2016).
49. Yang, D. et al. Enrichment of G2/M cell cycle phase in human pluripotent stem cells enhances HDR-mediated gene repair with customizable endonucleases. *Sci Rep* 6, 21264 (2016).
50. Yu, C. et al. Small molecules enhance CRISPR genome editing in pluripotent stem cells. *Cell Stem Cell* 16, 142-147 (2015).
51. Zar, J. H. Biostatistical Analysis. (Prentice Hall, New Jersey; 1999).
52. Zetsche, B. et al. Cpf1 is a single RNA-guided endonuclease of a class 2 CRISPR-Cas system. *Cell* 163, 759-771 (2015).
53. Zhang, J. P. et al. Efficient precise knockin with a double cut HDR donor after CRISPR/Cas9-mediated double-stranded DNA cleavage. *Genome Biol* 18, 35 (2017).
54. Zhou, Y. et al. Regulation of the DNA Damage Response by DNA-PKcs Inhibitory Phosphorylation of ATM. *Mol Cell* 65, 91-104 (2017).

The invention claimed is:

1. A method of enhancing homology directed repair in genome editing, comprising introducing a staggered cut into a double-stranded genome of a target eukaryotic cell in vitro and using a combination of
   (a) at least one compound (III) which is a DNA-PK inhibitor,
   (b) at least one compound (I) which is an HDAC inhibitor,
   (c) at least one compound (II) which is an NAE inhibitor; and
   (d) at least one compound (IV) which is an RPA inhibitor,
   wherein the genome editing comprises introducing a staggered cut with 5' overhangs into the double-stranded genome of the target cell, and
   wherein the target eukaryotic cell is a human pluripotent stem cell.

2. The method of claim 1,
   wherein the compound (I) is Trichostatin A, and/or
   the compound (II) is MLN4924, and/or
   the compound (III) is NU7026 and/or
   the compound (IV) is NSC15520.

3. The method of claim 1, wherein the staggered cut with 5' overhangs is introduced by a CRISPR/Cas9 nickase enzyme or a CRISPR/Cpf1 enzyme.

4. The method of claim 1, wherein the genome editing comprises (i) the presence of a CRISPR/Cas9D10A enzyme in the target cell, or (ii) the presence of a CRISPR/Cpf1 enzyme in the target cell.

5. The method of claim 1, wherein the human pluripotent stem cell is a human induced or embryonic pluripotent stem cell.

6. The method of claim 1, wherein the target eukaryotic cell comprises a catalytically inactive DNA protein kinase catalytic subunit comprising a K3753R substitution.

7. The method of claim 1, wherein the genome editing comprises introducing a single-stranded or double-stranded donor DNA molecule carrying a desired mutation into the target cell.

8. A method enhancing homology directed repair in editing the genome of an eukaryotic target cell in vitro or ex vivo, wherein the eukaryotic target cell is a human pluripotent stem cell, comprising introducing a combination of (a) at least one compound (III) which is a DNA-PK inhibitor, (b) at least one compound (I) which is an HDAC inhibitor, (c) at least one compound (II) which is an NAE inhibitor, and (d) at least one compound (IV) which is an RPA inhibitor, into the target cell, wherein the genome editing comprises introducing a staggered cut with 5' overhangs into the double-stranded genome of the target cell.

9. A method of enhancing homology directed repair in genome editing of a human induced or embryonic pluripotent stem cell in vitro or ex vivo, comprising:
   a) introducing a staggered cut with 5' overhangs into a double-stranded genome of the human induced or embryonic pluripotent stem cell; and
   b) introducing a combination of at least one compound (I) which is an HDAC inhibitor, at least one compound (II) which is an NAE inhibitor, at least one compound (III) which is a DNA-PK inhibitor, and at least one compound (IV) which is an RPA inhibitor into the human induced or embryonic pluripotent stem cell.

* * * * *

SEQUENCE LISTING

```
<160> NUMBER OF SEQ ID NOS: 66

<210> SEQ ID NO 1
<211> LENGTH: 20
<212> TYPE: DNA
<213> ORGANISM: Artificial Sequence
<220> FEATURE:
<223> OTHER INFORMATION: CALD1 t1

<400> SEQUENCE: 1
tggagactat tgctgcttga                                              20

<210> SEQ ID NO 2
<211> LENGTH: 20
<212> TYPE: DNA
<213> ORGANISM: Artificial Sequence
<220> FEATURE:
<223> OTHER INFORMATION: CALD1 t2

<400> SEQUENCE: 2
gcagtatacc agtgcaattg                                              20

<210> SEQ ID NO 3
<211> LENGTH: 20
<212> TYPE: DNA
<213> ORGANISM: Artificial Sequence
<220> FEATURE:
<223> OTHER INFORMATION: KATNA1 t1

<400> SEQUENCE: 3
aaatgatgac ccttccaaaa                                              20

<210> SEQ ID NO 4
<211> LENGTH: 20
<212> TYPE: DNA
<213> ORGANISM: Artificial Sequence
<220> FEATURE:
<223> OTHER INFORMATION: KATNA1 t2

<400> SEQUENCE: 4
```

```
caacaccutaa aataagggta                                              20

<210> SEQ ID NO 5
<211> LENGTH: 20
<212> TYPE: DNA
<213> ORGANISM: Artificial Sequence
<220> FEATURE:
<223> OTHER INFORMATION: SLITRK1 t1

<400> SEQUENCE: 5
gctaacagtt taccctgccc                                               20

<210> SEQ ID NO 6
<211> LENGTH: 20
<212> TYPE: DNA
<213> ORGANISM: Artificial Sequence
<220> FEATURE:
<223> OTHER INFORMATION: SLITRK1 t1

<400> SEQUENCE: 6
acccgtcgct atcgctgctg                                               20

<210> SEQ ID NO 7
<211> LENGTH: 21
<212> TYPE: DNA
<213> ORGANISM: Artificial Sequence
<220> FEATURE:
<223> OTHER INFORMATION: HPRT t1

<400> SEQUENCE: 7
ggttaaagat ggttaaatga t                                             21

<210> SEQ ID NO 8
<211> LENGTH: 21
<212> TYPE: DNA
<213> ORGANISM: Artificial Sequence
<220> FEATURE:
<223> OTHER INFORMATION: DMNT1 t1

<400> SEQUENCE: 8
ctgatggtcc atgtctgtta c                                             21

<210> SEQ ID NO 9
<211> LENGTH: 20
<212> TYPE: DNA
<213> ORGANISM: Artificial Sequence
<220> FEATURE:
<223> OTHER INFORMATION: iCRISPR BFP insertion t1

<400> SEQUENCE: 9
tgtcggctgc tgggactccg                                               20

<210> SEQ ID NO 10
<211> LENGTH: 20
<212> TYPE: DNA
<213> ORGANISM: Artificial Sequence
<220> FEATURE:
<223> OTHER INFORMATION: iCRISPR BFP insertion t2

<400> SEQUENCE: 10
tacagcatcg gcctggctat                                               20

<210> SEQ ID NO 11
<211> LENGTH: 20
<212> TYPE: DNA
<213> ORGANISM: Artificial Sequence
```

```
<220> FEATURE:
<223> OTHER INFORMATION: PRKDC t1

<400> SEQUENCE: 11
ggtcctcgcc acccttcacc                                              20

<210> SEQ ID NO 12
<211> LENGTH: 20
<212> TYPE: DNA
<213> ORGANISM: Artificial Sequence
<220> FEATURE:
<223> OTHER INFORMATION: PRKDC t2

<400> SEQUENCE: 12
gcgcgtggag cagctcttcc                                              20

<210> SEQ ID NO 13
<211> LENGTH: 20
<212> TYPE: DNA
<213> ORGANISM: Artificial Sequence
<220> FEATURE:
<223> OTHER INFORMATION: PRKDC t1-back

<400> SEQUENCE: 13
ggtcctcgcc acctctcacc                                              20

<210> SEQ ID NO 14
<211> LENGTH: 90
<212> TYPE: DNA
<213> ORGANISM: Artificial Sequence
<220> FEATURE:
<223> OTHER INFORMATION: CALD1 Cas9

<400> SEQUENCE: 14
gtatactgct ccagtctgct gtcaatcttg gagactactg ctgcttgatg ggtcgatttg     60
acaccactgc taaaaagta aacacataca                                      90

<210> SEQ ID NO 15
<211> LENGTH: 153
<212> TYPE: DNA
<213> ORGANISM: Artificial Sequence
<220> FEATURE:
<223> OTHER INFORMATION: CALD1 Cas9D10A

<400> SEQUENCE: 15
ttatatgtat gtgtttactt ttttagcagt ggtgtcaaat cgacccatca agctgcagta     60
gtctccaaga ttgacagcag actggagcag tataccagtg ctattgaggt gagaattgtc    120
ctcagcgtta tggtcctgct gaacagaaat aga                                 153

<210> SEQ ID NO 16
<211> LENGTH: 90
<212> TYPE: DNA
<213> ORGANISM: Artificial Sequence
<220> FEATURE:
<223> OTHER INFORMATION: KATNA1 Cas9

<400> SEQUENCE: 16
gaagggtcat cattttcaga agcacctcca acacctaaaa taagggaaag gggagagtga     60
aaaagatatt aagttggatt ataccaaatg                                     90

<210> SEQ ID NO 17
<211> LENGTH: 147
<212> TYPE: DNA
```

<213> ORGANISM: Artificial Sequence
<220> FEATURE:
<223> OTHER INFORMATION: KATNA1 Cas9D10A

<400> SEQUENCE: 17

| | |
|---|---|
| ctcatctata tcccagggaa aattagtagc tgccagaacc ataaccattt tagaagggtc | 60 |
| atcattttca gaggcgcctc caacacctaa ataacggta aggggagagt gaaaaagata | 120 |
| ttaagttgga ttataccaaa tgaagct | 147 |

<210> SEQ ID NO 18
<211> LENGTH: 147
<212> TYPE: DNA
<213> ORGANISM: Artificial Sequence
<220> FEATURE:
<223> OTHER INFORMATION: KATNA1 Cas9D10A 2

<400> SEQUENCE: 18

| | |
|---|---|
| ctcatctata tcccagggaa aattagtagc tgccagaacc ataaccattt tagaagggtc | 60 |
| atcattttca gaagcacctc caacacctaa ataacggta aggggagagt gaaaaagata | 120 |
| ttaagttgga ttataccaaa tgaagct | 147 |

<210> SEQ ID NO 19
<211> LENGTH: 90
<212> TYPE: DNA
<213> ORGANISM: Artificial Sequence
<220> FEATURE:
<223> OTHER INFORMATION: SLITRK1 Cas9

<400> SEQUENCE: 19

| | |
|---|---|
| tgttagctaa gggtttgttc ctggcgctac ccgtcgctat cgctgcggtg ggtctgattt | 60 |
| tgatctgcca gttgcctggg atctttgtac | 90 |

<210> SEQ ID NO 20
<211> LENGTH: 155
<212> TYPE: DNA
<213> ORGANISM: Artificial Sequence
<220> FEATURE:
<223> OTHER INFORMATION: SLITRK1 Cas9D10A

<400> SEQUENCE: 20

| | |
|---|---|
| tcatctttaa acccgaccct gggatgtggt cgcagctgca gcccccagga cagggtaaac | 60 |
| tgttagctaa gggtttgttc ctggcactgc ccgtcgctat cgctgcggtg ggtctgattt | 120 |
| tgatctgcca gttgcctggg atctttgtac ctccg | 155 |

<210> SEQ ID NO 21
<211> LENGTH: 155
<212> TYPE: DNA
<213> ORGANISM: Artificial Sequence
<220> FEATURE:
<223> OTHER INFORMATION: SLITRK1 Cas9D10A 2

<400> SEQUENCE: 21

| | |
|---|---|
| tcatctttaa acccgaccct gggatgtggt cgcagctgca gcccccaggg catggtaaac | 60 |
| tgttagctaa gggtttgttc ctggcgctac ccgtcgctat cgcagctgtg ggtctgattt | 120 |
| tgatctgcca gttgcctggg atctttgtac ctccg | 155 |

<210> SEQ ID NO 22
<211> LENGTH: 90
<212> TYPE: DNA
<213> ORGANISM: Artificial Sequence

```
<220> FEATURE:
<223> OTHER INFORMATION: HPRT Cpf1

<400> SEQUENCE: 22
gccatttcac ataaaactct tttaggttat agatggttaa atgaatgaca aaaaaagtaa      60
ttcacttaca gtctggctta tatccaacac                                      90

<210> SEQ ID NO 23
<211> LENGTH: 90
<212> TYPE: DNA
<213> ORGANISM: Artificial Sequence
<220> FEATURE:
<223> OTHER INFORMATION: DMNT1 Cpf1

<400> SEQUENCE: 23
ttaacatcag tacgttaatg tttcctgatc gtccatgtct gttagtcgcc tgtcaagtgg      60
cgtgacaccg ggcgtgttcc ccagagtgac                                      90

<210> SEQ ID NO 24
<211> LENGTH: 922
<212> TYPE: DNA
<213> ORGANISM: Artificial Sequence
<220> FEATURE:
<223> OTHER INFORMATION: mtagBFP-iCRISPR-Cas9n

<400> SEQUENCE: 24
aaagacgatg acgataagat ggccccaaag aagaagcgga aggtcggtat ccacggagtc      60
ccagcagccg tgagcaaggg cgaggagctg atcaaggaga acatgcacat gaagctgtac     120
atggagggca ccgtggacaa ccaccacttc aagtgcacca gcgagggcga gggcaagccc     180
tacgagggca cccagaccat gcgcatcaag gtggtggagg gcggcccct gcccttcgcc      240 ttcgacatcc tggccaccag cttcctgtac ggcagcaaga ccttcatcaa ccacacccag     300
ggcatccccg acttcttcaa gcagagcttc cccgagggct tcacctggga gcgcgtgacc     360
acctacgagg acggcggcgt gctgaccgcc acccaggaca ccagcctgca ggacggctgc     420
ctgatctaca acgtgaagat ccgcggcgtg aacttcacca gtaatgggcc tgtgatgcag     480
aagaagactc tgggctggga ggcattcacc gagaccctct atccggctga tggtgggctc     540
gagggtcgca acgatatggc tttgaaactc gtcggaggaa gtcacctcat cgcaaacgct     600
aaaacaacct ataggtctaa gaagcccgcc aagaacttga aaatgccagg ggtctactat     660
gtagattacc gcttggaacg aattaaagag gctaataatg agacttacgt agaacaacac     720
gaggtagcag tcgctcgata ttgcgacttg ccgagtaagc tcggacataa gctgaacggc     780
agtggagaag gtcggggatc actcctgacg tgtggagatg ttgaagagaa ccccggcccc     840
gacaagaagt acagcatcgg cctggccatc ggcaccaact ctgtgggctg ggccgtgatc     900
accgacgagt acaaggtgcc ca                                             922

<210> SEQ ID NO 25
<211> LENGTH: 137
<212> TYPE: DNA
<213> ORGANISM: Artificial Sequence
<220> FEATURE:
<223> OTHER INFORMATION: PRKDC Cas9n

<400> SEQUENCE: 25
gcgaaggccc aagcgcatca tcatccgtgg ccatgacgag agggaacacc ctttcctggt      60
gagaggtggc gaggacctgc ggcaggacca gcgcgtggag cagctcttcc aggtcatgaa     120
```
tgggatcctg gcccaag                                                          137

<210> SEQ ID NO 26
<211> LENGTH: 137
<212> TYPE: DNA
<213> ORGANISM: Artificial Sequence
<220> FEATURE:
<223> OTHER INFORMATION: PRKDC-back Cas9n

<400> SEQUENCE: 26
gcgaaggccc aagcgcatca tcatccgtgg ccatgacgag agggaacacc ctttcctggt      60
gaagggtggc gaggacctgc ggcaggacca gcgcgtggag cagctcttcc aggtcatgaa     120
tgggatcctg gcccaag                                                          137

<210> SEQ ID NO 27
<211> LENGTH: 60
<212> TYPE: DNA
<213> ORGANISM: Artificial Sequence
<220> FEATURE:
<223> OTHER INFORMATION: CALD1 forward

<400> SEQUENCE: 27
acactctttc cctacacgac gctcttccga tctgctaatc agctagcata tgtatgagaa      60

<210> SEQ ID NO 28
<211> LENGTH: 59
<212> TYPE: DNA
<213> ORGANISM: Artificial Sequence
<220> FEATURE:
<223> OTHER INFORMATION: CALD1 reverse

<400> SEQUENCE: 28
gtgactggag ttcagacgtg tgctcttccg atctttggac ttgattattg tcctaagtg       59

<210> SEQ ID NO 29
<211> LENGTH: 54
<212> TYPE: DNA
<213> ORGANISM: Artificial Sequence
<220> FEATURE:
<223> OTHER INFORMATION: KATNA1 forward

<400> SEQUENCE: 29
acactctttc cctacacgac gctcttccga tctcctgacg gcaaaggaat atag            54

<210> SEQ ID NO 30
<211> LENGTH: 57
<212> TYPE: DNA
<213> ORGANISM: Artificial Sequence
<220> FEATURE:
<223> OTHER INFORMATION: KATNA1 reverse

<400> SEQUENCE: 30
gtgactggag ttcagacgtg tgctcttccg atctactgtg cttccttgta ttgttgt         57

<210> SEQ ID NO 31
<211> LENGTH: 52
<212> TYPE: DNA
<213> ORGANISM: Artificial Sequence
<220> FEATURE:
<223> OTHER INFORMATION: SLITRK1 forward

<400> SEQUENCE: 31
acactctttc cctacacgac gctcttccga tctgggcttc aaatcagcca ag              52

```
<210> SEQ ID NO 32
<211> LENGTH: 54
<212> TYPE: DNA
<213> ORGANISM: Artificial Sequence
<220> FEATURE:
<223> OTHER INFORMATION: SLITRK1 reverse

<400> SEQUENCE: 32
gtgactggag ttcagacgtg tgctcttccg atcttttcaa gacaaatggg caag        54

<210> SEQ ID NO 33
<211> LENGTH: 53
<212> TYPE: DNA
<213> ORGANISM: Artificial Sequence
<220> FEATURE:
<223> OTHER INFORMATION: HPRT forward

<400> SEQUENCE: 33
acactctttc cctacacgac gctcttccga tctggtgaaa aggaccccac gaa         53

<210> SEQ ID NO 34
<211> LENGTH: 58
<212> TYPE: DNA
<213> ORGANISM: Artificial Sequence
<220> FEATURE:
<223> OTHER INFORMATION: HPRT reverse

<400> SEQUENCE: 34
gtgactggag ttcagacgtg tgctcttccg atcttggcaa atgtgcctct ctacaaat    58

<210> SEQ ID NO 35
<211> LENGTH: 55
<212> TYPE: DNA
<213> ORGANISM: Artificial Sequence
<220> FEATURE:
<223> OTHER INFORMATION: DMNT1 forward

<400> SEQUENCE: 35
acactctttc cctacacgac gctcttccga tcttgaacgt tcccttagca ctctg       55

<210> SEQ ID NO 36
<211> LENGTH: 54
<212> TYPE: DNA
<213> ORGANISM: Artificial Sequence
<220> FEATURE:
<223> OTHER INFORMATION: DMNT1 reverse

<400> SEQUENCE: 36
gtgactggag ttcagacgtg tgctcttccg atctccttag cagcttcctc ctcc        54

<210> SEQ ID NO 37
<211> LENGTH: 23
<212> TYPE: DNA
<213> ORGANISM: Artificial Sequence
<220> FEATURE:
<223> OTHER INFORMATION: Q5 D10A forward

<400> SEQUENCE: 37
tggtgccgat agccaggccg atg                                           23

<210> SEQ ID NO 38
<211> LENGTH: 18
<212> TYPE: DNA
<213> ORGANISM: Artificial Sequence
<220> FEATURE:
<223> OTHER INFORMATION: Q5 D10A reverse
```

```
<400> SEQUENCE: 38
actctgtggg ctgggccg                                                    18

<210> SEQ ID NO 39
<211> LENGTH: 53
<212> TYPE: DNA
<213> ORGANISM: Artificial Sequence
<220> FEATURE:
<223> OTHER INFORMATION: PRKDC forward

<400> SEQUENCE: 39
acactctttc cctacacgac gctcttccga tctctagcct gtgccctgag atg            53

<210> SEQ ID NO 40
<211> LENGTH: 55
<212> TYPE: DNA
<213> ORGANISM: Artificial Sequence
<220> FEATURE:
<223> OTHER INFORMATION: PRKDC reverse

<400> SEQUENCE: 40
gtgactggag ttcagacgtg tgctcttccg atctgcacaa cgctataggt cctca          55

<210> SEQ ID NO 41
<211> LENGTH: 69
<212> TYPE: DNA
<213> ORGANISM: Artificial Sequence
<220> FEATURE:
<223> OTHER INFORMATION: partial sequence of SEQ ID NO: 15

<400> SEQUENCE: 41
acccatcaag ctgcagtagt ctccaagatt gacagcagac tggagcagta taccagtgct    60
attgaggtg                                                             69

<210> SEQ ID NO 42
<211> LENGTH: 53
<212> TYPE: DNA
<213> ORGANISM: Artificial Sequence
<220> FEATURE:
<223> OTHER INFORMATION: partial sequence of SEQ ID NO: 14

<400> SEQUENCE: 42
gtatactgct ccagtctgct gtcaatcttg gagactactg ctgcttgatg ggt            53

<210> SEQ ID NO 43
<211> LENGTH: 63
<212> TYPE: DNA
<213> ORGANISM: Artificial Sequence
<220> FEATURE:
<223> OTHER INFORMATION: partial sequence of SEQ ID NO: 17

<400> SEQUENCE: 43
aaccatttta gaagggtcat cattttcaga ggcgcctcca cacctaaaa taacggtaag    60 ggg                                                                   63

<210> SEQ ID NO 44
<211> LENGTH: 53
<212> TYPE: DNA
<213> ORGANISM: Artificial Sequence
<220> FEATURE:
<223> OTHER INFORMATION: partial sequence of SEQ ID NO: 16

<400> SEQUENCE: 44
gaagggtcat cattttcaga agcacctcca cacctaaaa taagggaaag ggg            53
```

```
<210> SEQ ID NO 45
<211> LENGTH: 71
<212> TYPE: DNA
<213> ORGANISM: Artificial Sequence
<220> FEATURE:
<223> OTHER INFORMATION: partial sequence of SEQ ID NO: 20

<400> SEQUENCE: 45
ccccaggaca gggtaaactg ttagctaagg gtttgttcct ggcactgccc gtcgctatcg    60
ctgcggtggg t                                                        71

<210> SEQ ID NO 46
<211> LENGTH: 53
<212> TYPE: DNA
<213> ORGANISM: Artificial Sequence
<220> FEATURE:
<223> OTHER INFORMATION: partial sequence of SEQ ID NO: 19

<400> SEQUENCE: 46
tgttagctaa gggtttgttc ctggcgctac ccgtcgctat cgctgcggtg ggt          53

<210> SEQ ID NO 47
<211> LENGTH: 14
<212> TYPE: PRT
<213> ORGANISM: Homo sapiens

<400> SEQUENCE: 47

Glu His Pro Phe Leu Val Lys Gly Gly Glu Asp Leu Arg Gln
1               5                   10

<210> SEQ ID NO 48
<211> LENGTH: 14
<212> TYPE: PRT
<213> ORGANISM: Cricetulus griseus

<400> SEQUENCE: 48

Glu Tyr Pro Phe Leu Val Lys Gly Gly Glu Asp Leu Arg Gln
1               5                   10

<210> SEQ ID NO 49
<211> LENGTH: 14
<212> TYPE: PRT
<213> ORGANISM: Danio rerio

<400> SEQUENCE: 49

Asp Tyr Pro Phe Leu Val Lys Gly Gly Glu Asp Leu Arg Gln
1               5                   10

<210> SEQ ID NO 50
<211> LENGTH: 69
<212> TYPE: DNA
<213> ORGANISM: Homo sapiens

<400> SEQUENCE: 50
acccatcaag cagcaatagt ctccaagatt gacagcagac tggagcagta taccagtgca    60
attgaggtg                                                           69

<210> SEQ ID NO 51
<211> LENGTH: 69
<212> TYPE: DNA
<213> ORGANISM: Homo sapiens

<400> SEQUENCE: 51
```

```
cacctcaatt gcactggtat actgctccag tctgctgtca atcttggaga ctattgctgc    60
ttgatgggt                                                            69

<210> SEQ ID NO 52
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(42)
<223> OTHER INFORMATION: a, c, t, g, unknown or other
<220> FEATURE:
<221> NAME/KEY: modified_base
<222> LOCATION: (112)..(153)
<223> OTHER INFORMATION: a, c, t, g, unknown or other

<400> SEQUENCE: 52
nnnnnnnnnn nnnnnnnnnn nnnnnnnnnn nnnnnnnnnn nnacccatca agctgcagta    60
gtctccaaga ttgacagcag actggagcag tataccagtg ctattgaggt gnnnnnnnnn   120
nnnnnnnnnn nnnnnnnnnn nnnnnnnnnn nnn                                153

<210> SEQ ID NO 53
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (54)..(90)
<223> OTHER INFORMATION: a, c, t, g, unknown or other

<400> SEQUENCE: 53
gtatactgct ccagtctgct gtcaatcttg gagactactg ctgcttgatg ggtnnnnnnn    60
nnnnnnnnnn nnnnnnnnnn nnnnnnnnnn                                     90

<210> SEQ ID NO 54
<211> LENGTH: 63
<212> TYPE: DNA
<213> ORGANISM: Homo sapiens

<400> SEQUENCE: 54
aaccattttg gaagggtcat cattttcaga agtacctcca cacctaaaat aagggtaag    60 ggg                                                                  63

<210> SEQ ID NO 55
<211> LENGTH: 63
<212> TYPE: DNA
<213> ORGANISM: Homo sapiens

<400> SEQUENCE: 55
ccccttaccc ttattttagg tgttggaggt acttctgaaa atgatgaccc ttccaaaatg    60
gtt                                                                  63

<210> SEQ ID NO 56
<211> LENGTH: 147
<212> TYPE: DNA
<213> ORGANISM: Artificial Sequence
<220> FEATURE:
```

```
<223> OTHER INFORMATION: Description of Artificial Sequence: Synthetic
      polynucleotide
<220> FEATURE:
<221> NAME/KEY: modified_base
<222> LOCATION: (1)..(42)
<223> OTHER INFORMATION: a, c, t, g, unknown or other
<220> FEATURE:
<221> NAME/KEY: modified_base
<222> LOCATION: (106)..(147)
<223> OTHER INFORMATION: a, c, t, g, unknown or other

<400> SEQUENCE: 56
nnnnnnnnnn nnnnnnnnnn nnnnnnnnnn nnnnnnnnnn nnaaccattt tagaagggtc        60
atcattttca gaggcgcctc caacacctaa aataacggta aggggnnnnn nnnnnnnnnn       120
nnnnnnnnnn nnnnnnnnnn nnnnnnn                                          147

<210> SEQ ID NO 57
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (54)..(90)
<223> OTHER INFORMATION: a, c, t, g, unknown or other

<400> SEQUENCE: 57
gaagggtcat cattttcaga agcacctcca acacctaaaa taagggaaag gggnnnnnnn        60
nnnnnnnnnn nnnnnnnnnn nnnnnnnnnn                                        90

<210> SEQ ID NO 58
<211> LENGTH: 71
<212> TYPE: DNA
<213> ORGANISM: Homo sapiens

<400> SEQUENCE: 58
ccccagggca gggtaaactg ttagctaagg gtttgttcct ggagctaccc gtcgctatcg        60
ctgctgtggg t                                                            71

<210> SEQ ID NO 59
<211> LENGTH: 71
<212> TYPE: DNA
<213> ORGANISM: Homo sapiens

<400> SEQUENCE: 59
acccacagca gcgatagcga cgggtagctc caggaacaaa cccttagcta acagtttacc        60
ctgccctggg g                                                            71

<210> SEQ ID NO 60
<211> LENGTH: 155
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(42)
<223> OTHER INFORMATION: a, c, t, g, unknown or other
<220> FEATURE:
<221> NAME/KEY: modified_base
<222> LOCATION: (114)..(155)
<223> OTHER INFORMATION: a, c, t, g, unknown or other
```

<400> SEQUENCE: 60
nnnnnnnnnn nnnnnnnnnn nnnnnnnnnn nnnnnnnnnn nncccagga cagggtaaac    60 tgttagctaa gggtttgttc ctggcactgc ccgtcgctat cgctgcggtg ggtnnnnnnn   120
nnnnnnnnnn nnnnnnnnnn nnnnnnnnnn nnnnn                              155

<210> SEQ ID NO 61
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (54)..(90)
<223> OTHER INFORMATION: a, c, t, g, unknown or other

<400> SEQUENCE: 61
tgttagctaa gggtttgttc ctggcgctac ccgtcgctat cgctgcggtg ggtnnnnnnn    60
nnnnnnnnnn nnnnnnnnnn nnnnnnnnnn                                    90

<210> SEQ ID NO 62
<211> LENGTH: 14
<212> TYPE: PRT
<213> ORGANISM: Macaca mulatta

<400> SEQUENCE: 62

Glu His Pro Phe Leu Val Lys Gly Gly Glu Asp Leu Arg Gln
1               5                   10

<210> SEQ ID NO 63
<211> LENGTH: 14
<212> TYPE: PRT
<213> ORGANISM: Mus sp.

<400> SEQUENCE: 63

Glu Tyr Pro Phe Leu Val Lys Gly Gly Glu Asp Leu Arg Gln
1               5                   10

<210> SEQ ID NO 64
<211> LENGTH: 14
<212> TYPE: PRT
<213> ORGANISM: Canis lupus familiaris

<400> SEQUENCE: 64

Glu Tyr Pro Phe Leu Val Lys Gly Gly Glu Asp Leu Arg Gln
1               5                   10

<210> SEQ ID NO 65
<211> LENGTH: 14
<212> TYPE: PRT
<213> ORGANISM: Unknown
<220> FEATURE:
<223> OTHER INFORMATION: Description of Unknown:
      Elephant sequence

<400> SEQUENCE: 65

Glu Tyr Pro Phe Leu Val Lys Gly Gly Glu Asp Leu Arg Gln
1               5                   10

```
<210> SEQ ID NO 66
<211> LENGTH: 14
<212> TYPE: PRT
<213> ORGANISM: Gallus gallus

<400> SEQUENCE: 66

Glu His Pro Phe Leu Val Lys Gly Gly Glu Asp Leu Arg Gln
1               5                   10
```